US008425927B2

(12) United States Patent
Hunter et al.

(10) Patent No.: US 8,425,927 B2
(45) Date of Patent: *Apr. 23, 2013

(54) COMPOSITIONS AND METHODS FOR COATING MEDICAL IMPLANTS

(75) Inventors: William L. Hunter, Vancouver (CA); David M. Gravett, Mountain View, CA (US); Philip M. Toleikis, Vancouver (CA); Richard T. Liggins, Coquitlam (CA); Troy A. E. Loss, North Vancouver (CA)

(73) Assignee: Angiotech International AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/939,565

(22) Filed: Nov. 4, 2010

(65) Prior Publication Data

US 2011/0129513 A1 Jun. 2, 2011

Related U.S. Application Data

(63) Continuation of application No. 11/343,714, filed on Jan. 31, 2006, now abandoned, which is a continuation of application No. 10/477,309, filed on May 27, 2003, now abandoned.

(60) Provisional application No. 60/383,419, filed on May 24, 2002.

(51) Int. Cl.
*A61F 2/00* (2006.01)
*A61F 13/00* (2006.01)
*A61F 13/02* (2006.01)

(52) U.S. Cl.
USPC ........... 424/423; 424/422; 424/426; 604/264; 604/265; 604/891.1

(58) Field of Classification Search .................. 424/401, 424/423, 426, 484, 486, 499; 604/890.1, 604/891.1
See application file for complete search history.

(56) References Cited

U.S. PATENT DOCUMENTS

| | | | |
|---|---|---|---|
| 3,852,450 A | 12/1974 | Silvestri et al. | 424/251 |
| 3,980,650 A | 9/1976 | Nauta | 260/256.4 Q |
| 4,017,626 A | 4/1977 | Gauri | 424/251 |
| 4,033,962 A | 7/1977 | Rosen | 260/256.4 N |
| 4,215,062 A | 7/1980 | Mitscher | 260/365 |
| 4,232,022 A | 11/1980 | Ponsford | 424/251 |
| 4,296,105 A | 10/1981 | Baurain et al. | 424/180 |
| 4,500,676 A | 2/1985 | Balazs et al. | 525/54.2 |
| 4,534,899 A | 8/1985 | Sears | 260/403 |
| 4,582,865 A | 4/1986 | Balazs et al. | 524/29 |
| 4,590,270 A | 5/1986 | Kompis et al. | 544/320 |
| 4,629,623 A | 12/1986 | Balazs et al. | 424/78 |
| 4,636,524 A | 1/1987 | Balazs et al. | 514/781 |
| 4,649,198 A | 3/1987 | Irikura et al. | 544/281 |
| 4,713,371 A | 12/1987 | Aretz et al. | 514/34 |
| 4,713,448 A | 12/1987 | Balazs et al. | 536/55.1 |
| 4,714,703 A | 12/1987 | Burckhalter | 514/274 |
| 4,774,249 A | 9/1988 | Kompis et al. | 514/272 |
| 4,795,741 A | 1/1989 | Leshchiner et al. | 514/21 |
| 4,814,182 A | 3/1989 | Graham et al. | 424/484 |
| 4,882,168 A | 11/1989 | Casey et al. | 424/468 |
| 4,888,176 A | 12/1989 | Langer et al. | 424/426 |
| 4,891,225 A | 1/1990 | Langer et al. | 424/428 |
| 4,913,743 A | 4/1990 | Brode et al. | 106/162 |
| 4,925,668 A | 5/1990 | Khan et al. | 424/422 |
| 4,976,697 A | 12/1990 | Walder et al. | 604/164 |
| 4,999,210 A | 3/1991 | Solomon et al. | 427/2 |
| 5,013,306 A | 5/1991 | Solomon et al. | 604/265 |
| 5,015,238 A | 5/1991 | Solomon et al. | 604/164 |
| 5,059,186 A | 10/1991 | Yamamoto et al. | 604/280 |
| 5,064,415 A | 11/1991 | Walder et al. | 604/164 |
| 5,069,899 A | 12/1991 | Whitbourne et al. | 424/56 |
| 5,091,442 A | 2/1992 | Milner | 523/122 |
| 5,099,013 A | 3/1992 | Balazs et al. | 536/55.1 |
| 5,128,326 A | 7/1992 | Balazs et al. | 514/54 |
| 5,130,126 A | 7/1992 | Koyama et al. | 424/78.18 |
| 5,143,724 A | 9/1992 | Leshchiner et al. | 424/78.08 |
| 5,145,684 A | 9/1992 | Liversidge et al. | 424/489 |
| 5,153,174 A | 10/1992 | Band et al. | 514/12 |
| 5,165,952 A | 11/1992 | Solomon et al. | 427/2 |
| 5,207,648 A | 5/1993 | Gross | 604/164 |
| 5,221,256 A | 6/1993 | Mahurkar | 604/43 |
| 5,238,926 A | 8/1993 | Cooper et al. | 514/50 |
| 5,242,073 A | 9/1993 | Willis et al. | 220/240 |
| 5,246,698 A | 9/1993 | Leshchiner et al. | 424/78.08 |

(Continued)

FOREIGN PATENT DOCUMENTS

| | | |
|---|---|---|
| DE | 19718430 | 1/1999 |
| EP | 0 117 485 | 9/1984 |

(Continued)

OTHER PUBLICATIONS

Basaki et al., "UFT and Its Metabolites Inhibit Cancer-Induced Angiogenesis via a VEGF—Related Pathway," *Oncology*, 14(10): 68-71, 2000.

Wendling et al., "5-Fluorouracil Blocks Transforming Growth Factor-β-Induced $\alpha_2$ Type I Collagen Gene (*COL1A2*) Expression in Human Fibroblasts via c-Jun $NH_2$-Terminal Kinase/Activator Protein-1 Activation," *Molecular Pharmacology*, 64(3):707-713, 2003.

Wyszynski et al., "Sustained Release of 5-Fluorouracil from Ethylene Acetate Copolymer," *Journal of Ocular Pharmacology* 5(2):141-146, 1989.

Alkan-Onyuksel, H. et al., "A Mixed Micellar Formulation Suitable for the Parenteral Administration of Taxol," *Pharmaceutical Research 11*(2): 206-212, Feb. 1994.

(Continued)

*Primary Examiner* — Michael G Hartley
*Assistant Examiner* — Jagadishwar Samala
(74) *Attorney, Agent, or Firm* — SEED IP Law Group PLLC

(57) ABSTRACT

Medical implants are provided which release an anthracycline, fluoropyrimidine, folic acid antagonist, podophylotoxin, camptothecin, hydroxyurea, and/or platinum complex, thereby inhibiting or reducing the incidence of infection associated with the implant.

9 Claims, 1 Drawing Sheet

U.S. PATENT DOCUMENTS

| | | | | |
|---|---|---|---|---|
| 5,266,563 A | 11/1993 | Balazs et al. | | 514/42 |
| 5,301,664 A | 4/1994 | Sievers et al. | | 128/200.23 |
| 5,322,520 A | 6/1994 | Milder | | 604/265 |
| 5,330,756 A | 7/1994 | Steuart et al. | | 424/405 |
| 5,346,898 A | 9/1994 | Cooper et al. | | 514/255 |
| 5,366,505 A | 11/1994 | Farber | | 623/11 |
| 5,378,475 A | 1/1995 | Smith et al. | | 424/473 |
| 5,399,351 A | 3/1995 | Leshchiner et al. | | 424/422 |
| 5,399,363 A | 3/1995 | Liversidge et al. | | 424/490 |
| 5,403,858 A | 4/1995 | Bastard et al. | | 514/449 |
| 5,407,683 A | 4/1995 | Shively | | 424/439 |
| 5,438,072 A | 8/1995 | Bobee et al. | | 514/449 |
| 5,439,686 A | 8/1995 | Desai et al. | | 424/451 |
| 5,451,424 A | 9/1995 | Solomon et al. | | 427/2.1 |
| 5,472,417 A | 12/1995 | Martin et al. | | 604/43 |
| 5,498,248 A | 3/1996 | Milder | | 604/265 |
| 5,512,055 A | 4/1996 | Domb et al. | | 604/265 |
| 5,520,664 A | 5/1996 | Bricault, Jr. et al. | | 604/265 |
| 5,525,348 A | 6/1996 | Whitbourne et al. | | 424/423 |
| 5,534,250 A | 7/1996 | Klaveness et al. | | 424/78.37 |
| 5,554,106 A | 9/1996 | Layman-Spillar et al. | | 602/42 |
| 5,569,207 A | 10/1996 | Gisselberg et al. | | 604/175 |
| 5,574,097 A | 11/1996 | Klaveness et al. | | 525/61 |
| 5,594,158 A | 1/1997 | Wheeler | | 552/201 |
| 5,609,629 A | 3/1997 | Fearnot et al. | | 623/1 |
| 5,616,119 A | 4/1997 | Davis | | 604/19 |
| 5,616,338 A | 4/1997 | Fox, Jr. et al. | | 424/423 |
| 5,620,419 A | 4/1997 | Lui et al. | | 604/116 |
| 5,624,704 A | 4/1997 | Darouiche et al. | | 427/2.24 |
| 5,707,366 A | 1/1998 | Solomon et al. | | 604/265 |
| 5,709,672 A | 1/1998 | Illner | | 604/265 |
| 5,716,981 A | 2/1998 | Hunter et al. | | 514/449 |
| 5,725,553 A | 3/1998 | Moenning | | 606/213 |
| 5,725,817 A | 3/1998 | Milder | | 264/104 |
| 5,741,224 A | 4/1998 | Milder et al. | | 604/20 |
| 5,741,779 A | 4/1998 | White et al. | | 514/12 |
| 5,752,941 A | 5/1998 | Romano et al. | | 604/265 |
| 5,759,564 A | 6/1998 | Milder et al. | | 424/426 |
| 5,783,689 A | 7/1998 | Miller et al. | | 536/28.52 |
| 5,797,869 A | 8/1998 | Martin et al. | | 604/43 |
| 5,798,115 A | 8/1998 | Santerre et al. | | 424/423 |
| 5,800,412 A | 9/1998 | Zhang et al. | | 604/280 |
| 5,817,666 A | 10/1998 | Katz | | 514/274 |
| 5,824,049 A | 10/1998 | Ragheb et al. | | 623/1 |
| 5,837,226 A | 11/1998 | Jungherr et al. | | 424/78.1 |
| 5,843,903 A | 12/1998 | Schally et al. | | 514/16 |
| 5,854,382 A | 12/1998 | Loomis | | 528/354 |
| 5,861,191 A | 1/1999 | Ferralli | | 427/316 |
| 5,873,904 A | 2/1999 | Ragheb et al. | | 623/1 |
| 5,886,026 A | 3/1999 | Hunter et al. | | 514/449 |
| 5,895,419 A | 4/1999 | Tweden et al. | | 623/2 |
| 5,902,283 A | 5/1999 | Darouiche et al. | | 604/265 |
| 5,912,225 A | 6/1999 | Mao et al. | | 514/2 |
| 5,921,954 A | 7/1999 | Mohr, Jr. et al. | | 604/53 |
| 5,921,965 A | 7/1999 | Blei | | 604/204 |
| 5,935,930 A | 8/1999 | White et al. | | 514/12 |
| 5,942,555 A | 8/1999 | Swanson et al. | | 522/35 |
| 5,994,341 A | 11/1999 | Hunter et al. | | 514/210 |
| 5,997,517 A | 12/1999 | Whitbourne | | 604/265 |
| 6,005,020 A | 12/1999 | Loomis | | 523/105 |
| 6,007,833 A | 12/1999 | Chudzik et al. | | 424/425 |
| 6,059,816 A | 5/2000 | Moenning | | 606/213 |
| 6,060,000 A | 5/2000 | Milder et al. | | 252/510 |
| 6,063,396 A | 5/2000 | Kelleher | | 424/428 |
| 6,071,447 A | 6/2000 | Bootman et al. | | 264/54 |
| 6,090,995 A | 7/2000 | Reich et al. | | 623/11 |
| 6,096,070 A | 8/2000 | Ragheb et al. | | 623/1 |
| 6,099,563 A | 8/2000 | Zhong | | 623/1.46 |
| 6,106,473 A | 8/2000 | Violante et al. | | 600/458 |
| 6,107,280 A | 8/2000 | White et al. | | 514/12 |
| 6,110,483 A | 8/2000 | Whitbourne et al. | | 424/423 |
| 6,117,125 A | 9/2000 | Rothbarth et al. | | 604/265 |
| 6,121,027 A | 9/2000 | Clapper et al. | | 435/180 |
| 6,132,765 A | 10/2000 | DiCosmo et al. | | 424/450 |
| 6,143,037 A * | 11/2000 | Goldstein et al. | | 424/422 |
| 6,149,574 A | 11/2000 | Trauthen et al. | | 600/3 |
| 6,153,212 A | 11/2000 | Mao et al. | | 424/426 |
| 6,156,345 A | 12/2000 | Chudzik et al. | | 424/484 |
| 6,166,173 A | 12/2000 | Mao et al. | | 528/398 |
| 6,179,817 B1 | 1/2001 | Zhong | | 604/265 |
| 6,197,051 B1 | 3/2001 | Zhong | | 623/1.46 |
| 6,197,785 B1 | 3/2001 | Jackson et al. | | 514/309 |
| 6,206,849 B1 | 3/2001 | Martin et al. | | 604/43 |
| 6,214,901 B1 | 4/2001 | Chudzik et al. | | 523/113 |
| 6,238,687 B1 | 5/2001 | Mao et al. | | 424/426 |
| 6,261,271 B1 | 7/2001 | Solomon et al. | | 604/265 |
| 6,273,875 B1 | 8/2001 | Siman et al. | | 604/264 |
| 6,287,484 B1 | 9/2001 | Hausslein et al. | | 252/512 |
| RE37,410 E * | 10/2001 | Brem et al. | | 424/484 |
| 6,299,604 B1 | 10/2001 | Ragheb et al. | | 604/265 |
| 6,306,166 B1 * | 10/2001 | Barry et al. | | 623/1.46 |
| 6,309,660 B1 | 10/2001 | Hsu et al. | | 424/425 |
| 6,316,522 B1 | 11/2001 | Loomis et al. | | 523/105 |
| 6,322,797 B1 | 11/2001 | Mao et al. | | 424/271 |
| 6,335,029 B1 | 1/2002 | Kamath et al. | | 424/423 |
| 6,338,904 B1 | 1/2002 | Patnaik et al. | | 428/423.1 |
| 6,340,465 B1 | 1/2002 | Hsu et al. | | 424/400 |
| 6,344,035 B1 | 2/2002 | Chudzik et al. | | 604/265 |
| 6,355,001 B1 | 3/2002 | Quinn et al. | | 600/505 |
| 6,361,526 B1 | 3/2002 | Reisdorf et al. | | 604/265 |
| 6,383,144 B1 | 5/2002 | Mooney et al. | | 600/549 |
| 6,387,052 B1 | 5/2002 | Quinn et al. | | 600/505 |
| 6,403,618 B1 | 6/2002 | Fernandez-Pol | | 514/354 |
| 6,403,758 B1 | 6/2002 | Loomis | | 528/354 |
| 6,409,723 B1 | 6/2002 | Edwards | | 606/41 |
| 6,409,764 B1 | 6/2002 | White et al. | | 623/16.11 |
| 6,419,673 B1 | 7/2002 | Edwards et al. | | 606/41 |
| 6,423,050 B1 | 7/2002 | Twardowski | | 604/500 |
| 6,425,853 B1 | 7/2002 | Edwards | | 600/29 |
| 6,468,649 B1 | 10/2002 | Zhong | | 428/341 |
| 6,475,434 B1 | 11/2002 | Darouiche | | 422/28 |
| 6,485,430 B1 | 11/2002 | Quinn et al. | | 600/505 |
| 6,485,737 B1 | 11/2002 | Mao et al. | | 424/426 |
| 6,497,729 B1 | 12/2002 | Moussy et al. | | 623/23.57 |
| 6,506,411 B2 | 1/2003 | Hunter et al. | | 424/501 |
| 6,518,426 B1 | 2/2003 | Gangjee | | 544/280 |
| 6,530,951 B1 | 3/2003 | Bates et al. | | 623/1.45 |
| 6,541,481 B2 | 4/2003 | Kath et al. | | 514/260.1 |
| 6,544,544 B2 | 4/2003 | Hunter et al. | | 424/424 |
| 6,599,275 B1 | 7/2003 | Fischer, Jr. | | 604/265 |
| 6,599,881 B1 | 7/2003 | White et al. | | 514/12 |
| 6,685,672 B1 | 2/2004 | Forman | | 604/101.03 |
| 6,730,064 B2 | 5/2004 | Ragheb et al. | | 604/265 |
| 6,730,313 B2 | 5/2004 | Helmus et al. | | 424/423 |
| 6,740,333 B2 | 5/2004 | Beckett et al. | | 424/436 |
| 6,753,071 B1 | 6/2004 | Pacetti | | 428/212 |
| 6,756,428 B2 | 6/2004 | Denesuk | | 524/47 |
| 6,774,278 B1 | 8/2004 | Ragheb et al. | | 623/11 |
| 6,786,922 B2 | 9/2004 | Schaeffer | | 623/1.15 |
| 6,918,927 B2 | 7/2005 | Bates et al. | | 623/1.15 |
| 6,926,919 B1 | 8/2005 | Hossainy et al. | | 427/2.25 |
| 6,942,634 B2 | 9/2005 | Odland | | 604/6.09 |
| 6,971,813 B2 | 12/2005 | Shekalim et al. | | 401/208 |
| 6,991,804 B2 | 1/2006 | Helmus et al. | | 424/423 |
| 6,997,894 B2 | 2/2006 | Caresio | | 604/6.16 |
| 6,997,898 B2 | 2/2006 | Forman | | 604/101.03 |
| 7,004,176 B2 | 2/2006 | Lau | | 128/898 |
| 7,011,682 B2 | 3/2006 | Lashinski et al. | | 623/2.37 |
| 7,087,089 B2 | 8/2006 | Patel et al. | | 623/23.72 |
| 7,175,873 B2 | 2/2007 | Roorda et al. | | 427/2.14 |
| 7,201,745 B2 | 4/2007 | DiMatteo et al. | | 604/523 |
| 7,254,946 B1 | 8/2007 | Quinn et al. | | 60/505 |
| 7,255,891 B1 | 8/2007 | Pacetti | | 427/2.24 |
| 7,296,577 B2 | 11/2007 | Lashinski et al. | | 128/898 |
| 7,306,580 B2 | 12/2007 | Paul et al. | | 604/264 |
| 7,311,697 B2 | 12/2007 | Osborne | | 604/524 |
| 7,335,228 B2 | 2/2008 | Schaeffer | | 623/1.15 |
| 7,344,599 B2 | 3/2008 | Shekalim et al. | | 118/264 |
| 2001/0049422 A1 | 12/2001 | Phaneuf et al. | | 525/452 |
| 2002/0016297 A1 | 2/2002 | Linde, II et al. | | 514/19 |
| 2002/0018795 A1 | 2/2002 | Whitbourne et al. | | 424/414 |
| 2002/0049349 A1 | 4/2002 | Kohlstruk et al. | | 560/25 |
| 2002/0055666 A1 | 5/2002 | Hunter et al. | | 600/1 |
| 2002/0065546 A1 | 5/2002 | Machan et al. | | 623/1.13 |
| 2002/0091230 A1 | 7/2002 | Mao et al. | | 528/398 |
| 2002/0133072 A1 | 9/2002 | Wang et al. | | 600/423 |
| 2002/0137814 A1 | 9/2002 | Dang et al. | | 523/122 |

| | | | | |
|---|---|---|---|---|
| 2002/0151617 | A1 | 10/2002 | Mao et al. | 523/115 |
| 2003/0004209 | A1 | 1/2003 | Hunter et al. | 514/449 |
| 2003/0036794 | A1 | 2/2003 | Ragheb et al. | 623/1.15 |
| 2003/0055053 | A1 | 3/2003 | Linde, II et al. | 514/227.8 |
| 2003/0108588 | A1* | 6/2003 | Chen et al. | 424/423 |
| 2003/0144362 | A1 | 7/2003 | Utterberg et al. | 514/724 |
| 2003/0144570 | A1 | 7/2003 | Hunter et al. | 600/1 |
| 2003/0175323 | A1 | 9/2003 | Utterberg et al. | 424/423 |
| 2003/0216758 | A1 | 11/2003 | Signore | 606/151 |
| 2003/0229390 | A1 | 12/2003 | Ashton et al. | 623/1.15 |
| 2004/0043052 | A1 | 3/2004 | Hunter et al. | 424/426 |
| 2004/0063606 | A1 | 4/2004 | Chu et al. | 514/1 |
| 2004/0117007 | A1 | 6/2004 | Whitbourne et al. | 623/1.42 |
| 2005/0042240 | A1 | 2/2005 | Utterberg et al. | 424/400 |
| 2005/0058673 | A1 | 3/2005 | Scholz et al. | 424/401 |
| 2005/0080008 | A1 | 4/2005 | White et al. | 514/12 |
| 2005/0089539 | A1 | 4/2005 | Scholz et al. | 424/401 |
| 2005/0147690 | A1 | 7/2005 | Masters et al. | 424/499 |
| 2005/0165342 | A1 | 7/2005 | Odland | 604/5.01 |
| 2005/0220839 | A1 | 10/2005 | DeWitt et al. | 424/423 |
| 2005/0220840 | A1 | 10/2005 | DeWitt et al. | 424/423 |
| 2005/0220841 | A1 | 10/2005 | DeWitt et al. | 424/423 |
| 2005/0220842 | A1 | 10/2005 | DeWitt et al. | 424/423 |
| 2005/0220843 | A1 | 10/2005 | DeWitt et al. | 424/423 |
| 2005/0232970 | A1 | 10/2005 | Stucke et al. | 424/426 |
| 2005/0244453 | A1 | 11/2005 | Stucke et al. | 424/423 |
| 2005/0244459 | A1 | 11/2005 | DeWitt et al. | 424/426 |
| 2005/0255142 | A1 | 11/2005 | Chudzik et al. | 424/426 |
| 2005/0256502 | A1 | 11/2005 | DiMatteo et al. | 604/523 |
| 2005/0281857 | A1 | 12/2005 | Heyer et al. | 424/423 |
| 2006/0024372 | A1 | 2/2006 | Utterberg et al. | 424/488 |
| 2006/0030669 | A1 | 2/2006 | Taton et al. | 525/242 |
| 2006/0051384 | A1 | 3/2006 | Scholz et al. | 424/405 |
| 2006/0051385 | A1 | 3/2006 | Scholz | 424/405 |
| 2006/0052452 | A1 | 3/2006 | Scholz | 514/557 |
| 2006/0073207 | A1 | 4/2006 | Masters et al. | 424/488 |
| 2006/0083772 | A1 | 4/2006 | DeWitt et al. | 424/426 |
| 2006/0147491 | A1 | 7/2006 | DeWitt et al. | 424/426 |
| 2006/0167531 | A1 | 7/2006 | Gertner et al. | 607/86 |
| 2006/0195165 | A1 | 8/2006 | Gertner et al. | 607/86 |
| 2006/0198868 | A1 | 9/2006 | DeWitt et al. | 424/426 |
| 2006/0210816 | A1 | 9/2006 | Finley | 428/457 |
| 2006/0216324 | A1 | 9/2006 | Stucke et al. | 424/422 |
| 2006/0259013 | A1 | 11/2006 | Ranalletta et al. | 604/539 |
| 2006/0271000 | A1 | 11/2006 | Ranalletta et al. | 604/263 |
| 2006/0271024 | A1 | 11/2006 | Gertner et al. | 606/2 |
| 2006/0276894 | A1 | 12/2006 | Finley | 623/11.11 |
| 2007/0059434 | A1 | 3/2007 | Roorda et al. | 427/2.1 |
| 2007/0065481 | A1 | 3/2007 | Chudzik et al. | 424/426 |
| 2007/0065482 | A1 | 3/2007 | Chudzik et al. | 424/426 |
| 2007/0065483 | A1 | 3/2007 | Chudzik et al. | 424/426 |
| 2007/0106261 | A1 | 5/2007 | DiMatteo et al. | 604/523 |
| 2007/0249986 | A1 | 10/2007 | Smego | 604/8 |
| 2007/0255140 | A1 | 11/2007 | Violante et al. | 600/458 |
| 2007/0259913 | A1 | 11/2007 | Deitchman et al. | 514/303 |
| 2008/0045894 | A1 | 2/2008 | Perchik et al. | 604/96.01 |
| 2008/0063627 | A1 | 3/2008 | Stucke et al. | 424/93.7 |

FOREIGN PATENT DOCUMENTS

| | | |
|---|---|---|
| EP | 0 134 928 | 3/1985 |
| EP | 0 171 739 | 2/1986 |
| EP | 0 774 258 | 5/1997 |
| EP | 0 778 258 | 6/1997 |
| EP | 0 882 461 | 12/1998 |
| EP | 0 955 056 | 11/1999 |
| EP | 1 065 202 | 1/2001 |
| EP | 0 633 032 | 2/2001 |
| EP | 1 113 008 | 7/2001 |
| EP | 1 155 689 | 11/2001 |
| JP | 52-89680 | 7/1977 |
| JP | 53-149985 | 12/1978 |
| JP | 55-59173 | 5/1980 |
| JP | 63-112530 | 5/1988 |
| WO | WO 91/07400 | 5/1991 |
| WO | WO 93/18751 | 9/1993 |
| WO | WO 94/26254 | 11/1994 |
| WO | WO 95/03036 | 2/1995 |
| WO | WO 96/13286 | 5/1996 |
| WO | WO 96/30060 | 10/1996 |
| WO | WO 97/28156 | 8/1997 |
| WO | WO 98/12243 | 3/1998 |
| WO | WO 98/19713 | 5/1998 |
| WO | WO 98/24483 | 6/1998 |
| WO | WO 98/41154 | 9/1998 |
| WO | WO 99/07417 | 2/1999 |
| WO | WO 99/55396 | 11/1999 |
| WO | WO 99/65538 | 12/1999 |
| WO | WO 00/09087 | 2/2000 |
| WO | WO 00/09088 | 2/2000 |
| WO | WO 00/09190 | 2/2000 |
| WO | WO 00/21584 | 4/2000 |
| WO | WO 00/21842 | 4/2000 |
| WO | WO 00/33764 | 6/2000 |
| WO | WO 01/15526 | 3/2001 |
| WO | WO 01/17575 | 3/2001 |
| WO | WO 02/09768 | 2/2002 |
| WO | WO 02/069949 | 9/2002 |
| WO | WO 02/087586 | 11/2002 |
| WO | WO 03/059408 | 7/2003 |
| WO | WO 2005/096990 | 10/2005 |

OTHER PUBLICATIONS

Allison, David G., et al., "Biofilms: problems of control," *SGM Symposium 59*: 309-327, 2000.

Anai, H. et al., "Sensitivity test for 5-Fluorouracil and Its Analogues, 1-(2-Tetrahydrofuryl)-5-Fluorouracil, Uracil/1-(2-Tetrahydrofuryl)-5-Fluorouracil (4:1) and 1-Hexylcarbamoyl-5-Fluorouracil, Using the Subrenal Capsule Assay," *Oncology 45*: 144-147, 1988.

Andoh et al., "Formation and Fate of Abnormal Ribosomes of *E. coli* Cells Treated with 5-Fluorouracil," *Proc. Nat. Acad. Sci.*, 54:1181-1189, 1965.

Arcamone, F. et al., "Doxorubicin Disaccharide Analogue: Apoptosis-Related Improvement of Efficasy In Vivo," *Journal of the National Cancer Institute* 89(16): 1217-1223, Aug. 20, 1997.

Arshady, R., "Preparation of Biodegradable Microspheres and Microcapsules: 2. Polylactides and related polyesters," *Journal of Controlled Release* 17: 1-22, 1991.

Badawey et al., "Potential anti-microbials. I. Synthesis and structure-activity studies of some new thiazolo[4,5-*d*]pyrimidine derivatives," *Eur J Med Chem.*, 28:91-96, 1993.

Bartoli et al., "In vitro and in vivo antitumoral activity of free, and encapsulated taxol," *J. Microencapsulation* 7(2): 191-197, 1990.

Bassetti, Stefano, et al., "Prolonged Antimicrobial Activity of a Catheter Containing Chlorhexidine-Silver Sulfadiazine Extends Protection against Catheter Infections In Vivo," *Antimicrobial Agents and Chemotherapy* 45(5):1535-1538, May 2001.

Bawa et al., "An Explanation for the Controlled Release of Macromolecules from Polymers," *Journal of Controlled Release* 1:259-267, 1985.

Bazile, D. et al., "Stealth Me.PEG-PLA Nanoparticles Avoid Uptake by the Mononuclear Phagocytes System," *Journal of Pharmaceutical Sciences* 84(4):493-498, Apr. 1995.

Bean et al., "Inhibitory Effects and Metabolism of 5-Fluoropyrimidine Derivatives in Pneumococcus," *Journal of Bacteriology*, 106(2):412-420, May 1971.

Bérubé and Lepage, "Unexpected Transesterification of N-(trifluoroacetyl) Doxorubicin with Acetylsalicylic Acid: Formation of 4'-O-Acetyl-N-(Trifluoroacetyl) Doxorubicin," *Synthetic Communications* 28(6): 1109-1116, 1998.

Block et al., "Experimental Therapy of Cladosporiosis and Sporotrichosis with 5-Fluorocytosine," *Antimicrobial Agents and Chemotherapy*, 3(1):95-98, Jan. 1973.

Bodet, C. A. et al., "Antibacterial Activities of Antineoplastic Agents," *Antimicrobial Agents and Chemotherapy*, 28(3):437-439, Sep. 1985.

Bollag and Harmann, "Tumor Inhibitory Effects of a New Fluorouracil Derivative: 5'-Deoxy-5-Fluorouridine," *European Journal of Cancer 16*: 427-432, 1980.

Brown et al., "In Vivo and In Vitro Release of Macromolecules from Polymeric Drug Delivery Systems," *Journal of Pharmaceutical Sciences* 72(10): 1181-1185, 1983.

Brun-Buisson, Christian, et al., "Prevention of intravascular catheter-related infection with newer chlorhexidine-silver sulfadiazine-coated catheters: a randomized controlled trial," *Intensive Care Med.* 30:837-843, 2004.

Burke, Kathryn, "Combating phlebitis: a peripheral cannula grading scale," *Nursing Times* 96(29):38-39, Jul. 20, 2000.

Cascone et al., "Collagen and hyaluronic acid based polymeric blends as drug delivery systems for the release of physiological concentrations of growth hormone," *Journal of Materials Science: Materials in Medicine* 5: 770-774, 1994.

Cassinelli, G. et al., "13-Deoxycarminomycin, a New Biosynthetic Anthracycline," *Journal of Natural Products* 48(3): 435-439, May-Jun. 1985.

Castelli, M., et al., "Bactericidal and Cytotoxic Effect of Combination of Norfloxacin and 5-Fluorouracil," *Anticancer Research* 9:49-52, 1989.

Cohen et al., "The Mode of Action of 5-Fluorouracil and its Derivatives," *Proc. Nat. Acad. Sci.*, 44:1004-1012, 1958.

Cohen, Seymour S., et al., "Studies on Unbalanced Growth in *Escherichia coli*," *Biochemistry* 40:885-893, 1954.

Cohen, Seymour S., et al., "The Mode of Action of 5-Fluorouracil and its Derivatives," *Biochemistry* 44:1004-1012, 1958.

Costerton, J.W., et al, "Bacterial Biofilms: A Common Cause of Persistent Infections," *Science* 284:1318-1322, May 21, 1999.

Cragg, Andrew H., et al., "Effect of Antineoplastic Agents on Smooth Muscle Cell Proliferation in Vitro: Implications for Prevention of Restenosis after Transluminal Angioplasty," *Journal of Vascular and Interventional Radiology* 3(2):273-277, May 1992.

Cserháti and Holló, "Interaction of taxol and other anticancer drugs with hydroxypropyl-β-cyclodextrin," *International Journal of Pharmaceutics* 108: 69-75, 1994.

Darouiche, Rabih O., et al., "A Comparison of Two Antimicrobial-Impregnated Central Venous Catheters," *The New England Journal of Medicine* 340(1):1-8, Jan. 7, 1999.

Dias, A.A., "Materials: The Evolving Functionalities of Coatings," *Medical Device Link*, downloaded on Feb. 15, 2008, available at http://www.devicelink.com.

Dickinson, Gordon M., et al., "Minireviews: Infections Associated with Indwelling Devices: Concepts of Pathogenesis; Infections Associated with Intravascular Devices," *Antimicrobial Agents and Chemotherapy* 33(5):597-601, May 1989.

Dimick, Justin B., et al., "Increased Resource Use Associated with Catheter-Related Bloodstream Infection in the Surgical Intensive Care Unit," *Arch Surg.* 136:229-234, Feb. 2001.

Donlan, Rodney M., "Biofilms and Device-Associated Infections," *Emerging Infectious Diseases* 7(2):277-281, Mar.-Apr. 2001.

Dunn, E.J. et al., "Synthesis of N-(aminoalkyl)chitosan for Microcapsules," *Journal of Applied Polymer Science* 50(2): 353-365, Oct. 10, 1993.

El-Sherbeny et al., "Synthesis of Some New Thiazolo[4,5-d]Pyrimidine Derivatives and Evaluation of Their Antifungal, Antiviral and Cytotoxic Activities," *Medicinal Chemistry Research*, 6:28-39, 1996.

Falchi, M. et al., "Antibacterial and Cytotoxic Effect of Ceftazidime-Mitoxantrone Association," *Anticancer Research* 9(2):291-292, 1989.

Fan, Barry M., "Preventing Vascular Catheter-Related Infections: Current Controversies," *Healthcare Epidemiology CID* 33:1733-1738, Nov. 15, 2001.

Galliani, S. et al., "Chemiluminescence Response of Human Neutrophils to *S. epidermidis* Adherent to i.v. Catheters: Influence of Strain Polymer, Proteins and Chemotherapy," *Abstracts of the 94th General Meeting of the American Society for Microbiology*, p. 70, Abstract No. B-231, 1994.

Galliani, S. et al., "Influence of strain, biomaterial, proteins, and oncostatic chemotherapy on *Staphylococcus epidermidis* adhesion to intravascular catheters in vitro," *The Journal of Laboratory and Clinical Medicine* 127(1): 71-80, Jan. 1996.

Ghosh et al., "2,4-Bis(arylamino)-5-methylpyrimidines as Antimicrobial Agents," *J Med. Chem.*, 10:974-975, Sep. 1967.

Gieringer, J.H. et al., "Effect of 5-Fluorouracil, Mitoxantrone, Methotrexate, and Vincristine on the Antibacterial Activity of Ceftriaxone, Ceftazidime, Cefotiam, Piperacillin, and Netilmicin," *Chemotherapy* 32(5): 418-424, 1986.

Goldschmidt et al., "Effect of chemotherapeutic agents upon microorganisms isolated from cancer patients," *Antimicrobial Agents and Chemotherapy* 1(4): 348-353, Apr. 1972.

Gómez, J.A. et al., "Synthesis of Novel-5-Fluorouracil Derivatives with 1,4-Oxaheteroepane Moieties," *Tetrahedron* 54(43):13295-13312, 1998.

Goodell, J.A. et al., "Preparation and release characteristics of tobramycin-impregnated polymethylmethacrylate," *American Journal of Hospital Pharmacy* 43(6): 1454-1461, Jun. 1986.

Goodman and Gilman, Editors. "The Pharmacological Basis of Therapeutics," Eighth Edition, New York, Pergamon Press, 1227-1230, 1990.

Gref, R. et al., "Biodegradably Long-Circulating Polymeric Nanospheres," *Science* 263:1600-1603, Mar. 18, 1994.

Hagen et al., "PLA-PEG Micelles—A Novel Drug Delivery System," *Proceed. Intern. Symp. Control. Rel. Bioact. Mater.* 22, Controlled Release Society, 1995, pp. 194-195.

Hamilton-Miller, "Antimicrobial activity of 21 anti-neoplastic agents," *The British Journal of Cancer* 49:367-369, 1984.

Heard, Stephen O., et al., Influence of Triple-Lumen Central Venous Catheters Coated with Chlorhexidine and Silver Sulfadiazine on the Incidence of Catheter-Related Bacteremia, *Arch Intern Med* 158:81-87, Jan. 12, 1998.

Hentzer, Morten et al., "Inhibition of quorum sensing in *Pseudomonas aeruginosa* biofilm bacteria by a halogenated furanone compound," *Microbiology* 148:87-102, 2002.

Herrmann, Mathias, et al., "Fibronectin, Fibrinogen, and Laminin Act as Mediators of Adherence of Clinical Staphylococcal Isolates to Foreign Material," *The Journal of Infectious Diseases* 158(4):693-701, Oct. 1988.

Herrmann, Mathias, et al., "Interaction of von Willebrand Factor with *Staphylococcus aureus*," *The Journal of Infectious Diseases* 176:984-991, 1997.

Holland et al., "Polymers for Biodegradably Medical Devices. 1. The Potential of Polyesters as Controlled Macromolecular Release Systems," *Journal of Controlled Release* 4: 155-180, 1986.

Holmes et al., "Viability of microorganisms in fluorouracil and cisplatin small-volume injections," *American Journal of Hospital Pharmacy*, 45:1089-91, May 1988.

Holt et al., "The antimycotic activity of 5-fluorocytosine," *J. Clin. Path.*, 26: 167-74, 1973.

Hoshi, A. et al., "Antitumor Activity of Metabolites of 1-Hexylcarbamoyl-5-fluorouracil and Related Compounds Against L 1210 Leukemia In Vivo and L5178Y Lymphoma Cells In Vitro," *Journal of Pharmacobio-Dynamics* 3(9): 478-481, Sep. 1980.

Hronowski and Szarek, "Synthesis of cyclopentane analogs of 5-fluorouracil nucleosides," *Canadian Journal of Chemistry* 70(4): 1162-1169, Apr. 1992.

Hugonnet, Stéphane, et al., "Nosocomial Bloodstream Infection and Clinical Sepsis," *Emerging Infectious Diseases* 10(1):76-81, Jan. 2004.

Hunt, Dale E., et al., "Killing of Cells in Bacterial Colonies," *Applied Microbiology* 15(2):334-339, Mar. 1967.

Hunter et al., "Anti-Angiogenic Compositions and Methods of Use," U.S. Appl. No. 10/389,261, filed Mar. 13, 2003.

Hunter et al., "Anti-Angiogenic Compositions and Methods of Use," U.S. Appl. No. 10/390,534, filed Mar. 14, 2003.

Hussain, M. et al., "Radiochemical assay to measure the biofilm produced by coagulase-negative staphylococci on solid surfaces and its use to quantitate the effects of various antibacterial compounds on the formation of the biofilm" *J. Med. Microbiol.* 37:62-69, 1992.

Ingrams, Duncan R., et al., "Does slow-release 5-fluorouracil and triamcinolone reduce subglottic stenosis?" *Archives of Otolaryngology Head & Neck Surgery* 118(2): 174-177, Feb. 1998.

Jaeger, K., et al., "Reduction of catheter-related infections in neutropenic patients: a prospective controlled randomized trial using a chlorhexidine and silver sulfadiazine-impregnated central venous catheter," *Ann Hematol* 84:258-262, 2005.

Jampel et al., "Glaucoma Filtration Surgery in Nonhuman Primates Using Taxol and Etoposide in Polyanhydride Carriers," *Investigative Ophthalmology & Visual Science* 34(11): 3076-3083, 1993.

Kesavan et al., "5-Fluorouracil Altered Morphology and Inhibited Growth of *Candida albicans*," *Journal of Clinical Microbiology*, 43(12):6215-6216, Dec. 2005.

Kim, B.S. et al., "Structure Elucidation and Antifungal Activity of an Anthracycline, Antibiotic, Daunomycin, Isolated from *Actinomadura roseola*," *Journal of Agricultural and Food Chemistry* 48(5): 1875-1881, 2000.

Kozai, S. et al., "A new method for the synthesis of $N^3$-alkylated analogs of 5-fluorouracil," *J. Chem. Soc., Perkin Transactions 1*(19): 3145-3146, Oct. 7, 1998.

Kwon et al., "Biodistribution of Micelle-Forming Polymer-Drug Conjugates," *Pharmaceutical Research* 10(7): 970-974, 1993.

Kwon et al., "Physical Entrapment of Adriamycin in AB Block Copolymer Micelles," *Pharmaceutical Research* 12(2): 192-195, 1995.

Langer and Folkman, "Controlled Release of Macromolecules from Polymers," in *Biomedical Polymers. Polymeric Materials and Pharmaceuticals for Biomedical Use*, Goldberg and Nakajime (eds), Academic Press, New York, 1980, pp. 113-137.

Levowitz, B.S. et al., "Biologic Compatibility and Applications of Hydron," *Transactions. American Society for Artificial Internal Organs* 14:82-88, 1968.

Li, Y-X. et al., "Cytotoxic Interactions of 5-Fluoroouracil and Nucleoside Analogues in Vitro," *Anticancer Research* 17(1A): 21-28, Jan.-Feb. 1997.

Linguist et al., "5-Fluorocytosine in the Treatment of Experimental Candidiasis in Immunosuppressed Mice," *Antimicrobial Agents and Chemotherapy*, 4(1):58-61, Jul. 1973.

Louie et al., "Efficacies of High-Dose Fluconazole plus Amphotericin B and High-Dose Fluconazole plus 5-Fluorocytosine versus Amphotericin B, Fluconazole, and 5-Fluorocytosine Monotherapies in Treatment of Experimental Endocarditis, Endophthalmitis, and Pyelonephritis Due to *Candida albicans*," *Antimicrobial Agents and Chemotherapy*, 43(12):2831-2840, Dec. 1999.

Machan et al., "Stent Grafts with Bioactive Coatings," U.S. Appl. No. 09/476,490, filed Dec. 30, 1999.

Maddox, Ray R., et al., "Double-blind study to investigate methods to prevent cephalothin-induced phlebitis," *Am J Hosp Pharm* 34:29-34, Jan. 1977.

Maehara, Y. et al., "UFT Is More Antineoplastic against Gastric Carcinoma than 5-Fluorouracil, 1-(2-Tetrahydrofuryl)-5-fluorouracil and 1-Hexylcarbamoyl-5-Fluorouracil," *Chemotherapy* 34(6): 484-489, Nov.-Dec. 1988.

Maki, D. G., et al., "A Semiquantitative Culture Method for Identifying Intravenous-Catheter-Related Infection," *The New England Journal of Medicine* 296(23):1305-1309, Jun. 9, 1977.

Maki, D. G., et al., "An Attachable Silver-Impregnated Cuff for Prevention of Infection with Central Venous Catheters: A Prospective Randomized Multicenter Trial," *The American Journal of Medicine* 85:307-314, Sep. 1988.

Maki, D.G., et al., "Clinical Trial of a Novel Antiseptic Central Venous Catheter," *American Society for Microbiology* 57(8):176, Oct. 1, 1991 (abstract).

Maki, D. G., et al., "Prevention of Central Venous Catheter-Related Bloodstream Infection by Use of an Antiseptic-Impregnated Catheter," *Annals of Internal Medicine* 127(4):257-266, Aug. 15, 1997.

Marshall, John L., et al., "An Alternate Method to Overcoming Central Venous Catheter Blockage in Patients Receiving High-Dose Fluorouracil and Leucovorin," *J Clin Oncol.* 11(7):1433-1434, Jul. 1993.

Martin et al., "In vitro Susceptibility of 245 Yeast Isolates to Amphotericin B, 5-Fluorocytosine, Ketoconazole, Fluconazole and Itraconazole," *Chemotherapy*, 38:335-339, 1992.

Matsuura, A. et al., "General Pharmacological Properties of Doxifluridine, A New Fluorouracil Derivative," *Oyo Yakuri* 29(5): 803-831, 1985.

McCaffery J., "Studies in the Toxicity and Clinical Application of 5-Fluorouracil," *The Medical Journal of Australia*, (2):582-585, Oct. 10, 1964.

Mermel, Leonard A., et al., "Guidelines for the Management of Intravascular Catheter-Related Infections," *Management Guidelines for Catheter Infections* 32:1249-1272, May 1, 2001.

Miwa, M. et al., "Comparative Studies on the Antitumor and Immunosuppressive Effects of the New Fluorouracil Derivative N4-Trimethoxybenzoyl-5'-deoxy-5-fluorocytidine and Its Paretn Drug 5'-Deoxy-5-fluorouridine," *Chemical & Pharmaceutical Bulletin* 38(4): 998-1003, Apr. 1990.

Miyazaki, S. et al., "Drug release from oral mucosal adhesive tablets of chitosan and sodium alginate," *International Journal of Pharmaceutics* 118(2): 257-263, May 1995.

Monteagudo, E. et al., "Conformational analysis of 4-demethoxy-7-O-[2,6-dideoxy-4-O-(2,3,6-trideoxy-3-amino-α-L-*lyxo*-hexapyranosyl)-α-L-*lyxo*-hexopyranosyl]adriamicinone, the first doxorubicin disaccharide analogue to be reported," *Carbohydrate Research* 300:11-16, 1997.

Morales, Manuel, et al., "Biofilm: the microbial "bunker" for intravascular catheter-related infection," *Support Care Cancer* 12:701-707, 2004.

Nagy, A. et al., "Synthesis and biological evaluation of cytotoxic analogs of somatostatin containing doxorubicin or its intensely potent derivative, 2-pyrrolinodoxorubicin," *Proc. Natl. Acad. Sci. USA* 95: 1794-1799, Feb. 1998.

Nsanzumuhire et al., "Chromomycosis Due to *Cladosporium trichoides* Treated with 5-Fluorocytosine," *Am J. Clinical Pathology*, 61:257 -263, Feb. 1974.

Okada, T., "Anti-Tumor Activities of 1-Acetyl-3-o-Toluyl-5-Fu," *Hiroshima Journal of Medical Sciences* 28(1-4): 49-66, 1979.

Patent Abstracts of Japan, JP 52-089680, Jul. 27, 1977.

Patent Abstracts of Japan, JP 53-149985, Dec. 27, 1978.

Patent Abstracts of Japan, JP-55-059173, May 2, 1980.

Perez-Blanco et al., "Ajoene and 5-fluorouracil in the topical treatment of *Cladophialophora carrionii* chromoblastomycosis in humans: a comparative open study," *Medical Mycology*, 41:517-520, 2003.

*Physician's Desk Reference (PDR) Electronic Library*, Carac Cream, 0.5% (Dermik), 59th Edition, 2005.

*Physician's Desk Reference (PDR)*, Thomson PDR, 52nd edition, Nov. 1997, pp. 2463-2464.

Pitt, C., "The controlled parenteral delivery of polypeptides and proteins," *International Journal of Pharmaceutics* 59: 173-196, 1990.

Pittillo et al., "Chemotherapeutic Activity of 5-Fluorocytosine Against a Lethal *Candida albicans* Infection in Mice," *Applied Microbiology*, 17(5):773-774, May 1969.

Polak, A., "Mode of Action of 5-Fluorocytosine and 5-Fluorouracil in Dematiaceous Fungi," *Sabouraudia*, 21:15-25, 1983.

Prajda, N. et al., "Comparison of Tumor Growth Inhibitory and Toxic Effects of a New Fluorouracil—Nitrosourea Derivative (B-3839)," in vivo 2:151-154, 1988.

Pratesi, G. et al., "Improved Efficacy and Enlarged Spectrum of Activity of a Novel Anthracycline Disaccharide Analogue of Doxorubicin against Human Tumor Xenografts," *Clinical Cancer Research* 4: 2833-2839, Nov. 1998.

Quaglia, M.G. et al., "Analysis of a New Doxorubicin Derivative (FCE 23762) and Related Compounds by High Performance Capillary Electrophoresis," *Journal of Liquid Chromatography* 17(18): 3911-3923, 1994.

Raad, Issam, et al., "Ultrastructural Analysis of Indwelling Vascular Catheters: A Quantitative Relationship between Luminal Colonization and Duration of Placement," *The Journal of Infectious Diseases* 168:400-407, Aug. 1993.

Raad, Issam, et al., "The Broad-Spectrum Activity and Efficacy of Catheters Coated with Minocycline and Rifampin," *The Journal of Infectious Diseases* 173:418-424, Feb. 1996.

Raad, Issam, et al., "Differential Time to Positivity: A Useful Method for Diagnosing Catheter-Related Bloodstream Infections," *Annals of Internal Medicine* 140(1):18-26, Jan. 6, 2004.

Rapoport, N.Y. et al., "Micellar delivery of doxorubicin and its paramagnetic analog, ruboxyl, to HL-60 cells: effect of micelle structure and ultrasound on the intracellular drug uptake," *Journal of Controlled Release* 58: 153-162, 1999.

Rauckman et al., "2,4-Diamino-5-benzylpyrimidines and Analogues as Antibacterial Agents, 10. 2,4-Diamino-5-(6-quinolylmethyl)- and —[(tetrahydro-6-quinolyl)methyl]pyrimidine Derivatives. Further Specificity Studies." *J. Med. Chemotherapy*, 32(8):1927-1935, 1989.

Rello, Jordi, et al., "Evaluation of Outcome of Intravenous Catheter-related Infections in Critically Ill Patients," *Am J Respir Crit Care Med 162*:1027-1030, 2000.

Ren, Dacheng et al., "Brief report. Inhibition of biofilm formation and swarming of *Escherichia coli* by (5Z)-4-bromo-5-(bromomethylene)-3-butyl-2(*5H*)-furanone," *Environmental Microbiology 3*(11):731-736, 2001.

Rhine et al., "Polymers for Sustained Macromolecule Release: Procedures to Fabricate Reproducible Delivery Systems and Control Release Kinetics," *Journal of Pharmaceutical Sciences 69*(3): 265-270, 1980.

Rijnders, Bart J.A., et al., "Catheter-Tip Colonization as a Surrogate End Point in Clinical Studies on Catheter-Related Bloodstream Infection: How Strong is the Evidence?" *Clinical Infectious Diseases 35*:1053-1058, Nov. 1, 2002.

Rival et al., "Antifungal activity in vitro of some imidazo[1,2-α]pyrimidine derivatives," *Eur J. Med. Chem.*, 26(1):13-18, 1991.

Shadomy et al., "In Vitro Activity of 5-Fluorocytosine Against *Candida* and *Torulopsis* Species," *Antimicrobial Agents and Chemotherapy*, 3(1):9-14, Jan. 1973.

Sharma and Straubinger, "Novel taxol formulations: preparation and characterization of taxol-containing liposomes," *Pharm. Res. 11*(6): 889-896, 1994.

Sharma, A. et al., "Antitumor Effect of Taxol-containing Liposomes in a Taxol-resistant Murine Tumor Model," *Cancer Research 53*: 5877-5881, Dec. 15, 1993.

Sheep, Robert E., et al., "Fatal Cardiac Tamponade: Occurrence With Other Complications After Left Internal Jugular Vein Catheterization," *JAMA 248*(13):1632-1635, Oct. 1, 1982.

Sherertz, Robert J., et al., "Efficacy of Antibiotic-Coated Catheters in Preventing Subcutaneous *Staphylococcus aureus* Infection in Rabbits," *The Journal of Infectious Diseases 167*:98-106, Jan. 1993.

Sherertz, Robert J., et al., "Three-Year Experience with Sonicated Vascular Catheter Cultures in a Clinical Microbiology Laboratory," *Journal of Clinical Microbiology 28*(1):76-82, Jan. 1990.

Shiraishi, S. et al., "Controlled-release preparation of indomethacin using calcium alginate gel," *Biol. Pharm. Bull. 16*(11): 1164-1168, Nov. 1993.

Sigma-Aldrich, Inc., Product Information, 5-Fluorouracil, Dec. 2002.

Stavorovsky et al., "*Candida* Sepsis Successfully Treated by Parental Administration of 5-Fluorocytosine," *International Surgery*, 61(8):426-429, Aug. 1976.

Suzuki, S. et al., "A Proposed Mechanism for the Selective Inhibition of Human Cytopmegalovirus Replication by 1-(2'-Deoxy-2'-fluoro-β-D-arabinofuranosyl)-5-fluorouracil," *Molecular Pharmacology 31*(3): 301-306, Mar. 1987.

Tarr, B.D. et al., "A New Parenteral Emulision for the Administration of Taxol," *Pharmaceutical Research 4*(2): 162-165, Apr. 1987.

Tennenberg, Steven, et al., "A Prospective Randomized Trial of an Antibiotic-and Antiseptic-Coated Central Venous Catheter in the Prevention of Catheter-Related Infections," *Arch Surg 132*:1348-1351, Dec. 1997.

Thacharodi and Rao, "Collogen-chitosan composite membranes for controlled release of propranolol hydrochloride," *Intern. Journal of Pharmaceuticals 120*(1): 115-118, Jun. 1995.

Tomasz et al., "The Mechanism of Bacterial Fragility Produced by 5-Flouroacil: The Accumulation of Cell Wall Precursors," *Proc. Nat. Acad. Sci.*, vol. 46:324-327, 1960.

Van der Wilt, C.L. et al., "In vitro antitumour activity of *cis-* and *trans-*5-fluoro-5,6-dihydro-6-alkoxy-uracils; effects on thymidylate synthesis," *British Journal of Cancer 68*: 702-707, 1993.

Veenstra, David L., et al., "Cost-Effectiveness of Antiseptic-Impregnated Central Venous Catheters for the Prevention of Catheter-Related Bloodstream Infection," *JAMA 282*(6):554-560, Aug. 11, 1999.

Veenstra, David L., et al., "Efficacy of Antiseptic-Impregnated Central Venous Catheters in Preventing Catheter-Related Bloodstream Infection," *JAMA 281*(3):261-267, Jan. 20, 1999.

von Eiff, Christof, et al., "Infections Associated with Medical Devices: Pathogenesis, Management and Prophylaxis," *Drugs 65*(2):179-214, 2005.

Wagner et al., "Effects of Purines and Pyrimidines on the Fungistatic Activity of 5-Fluorocytosine in *Aspergillus* Species," *Antimicrobial Agents and Chemotherapy*, 11(2):229-233, Feb. 1977.

Waldorf et al., "Mechanisms of Action of 5-Fluorocytosine," *Antimicrobial Agents and Chemotherapy*, 23(1):79-85, Jan. 1983.

Walter et al., "Interstitial Taxol Delivered from a Biodegradable Polymer Implant against Experimental Malignant Glioma," *Cancer Research 54*: 2207-2212, 1994.

Wang et al., "Expression of Human Mitochondrial Thymidine Kinase in *Escherichia coli*: Correlation between the Enzymatic Activity of Pyrimidine Nucleoside Analogues and Their Inhibitory Effect on Bacterial Growth," *Biochemical Pharmacology*, 59:1583-1588, 2000.

Yokoyama et al., "Improved synthesis of adriamycin-conjugated poly(ethylene oxide)-poly(aspartic acid) block copolymer and formation of unimodal micellar structure with controlled amount of physically entrapped adriamycin," *Journal of Controlled Release 32*: 269-277, 1994.

Zhang, J-R. et al., "Detection of Metabolites of a Fluorouracil Derivative A-OT-Fu," *Chinese Journal of Pharmaceuticals 20*(11): 513-515, 1989.

Zou, Y. et al., "Quantitative Analysis of the Lipophilic Doxorubicin Analogue Annamycin in Plasma and Tissue Samples by Reversed-Phase Chromatography," *Journal of Pharmaceutical Sciences 82*(11): 1151-1154, Nov. 1993.

* cited by examiner

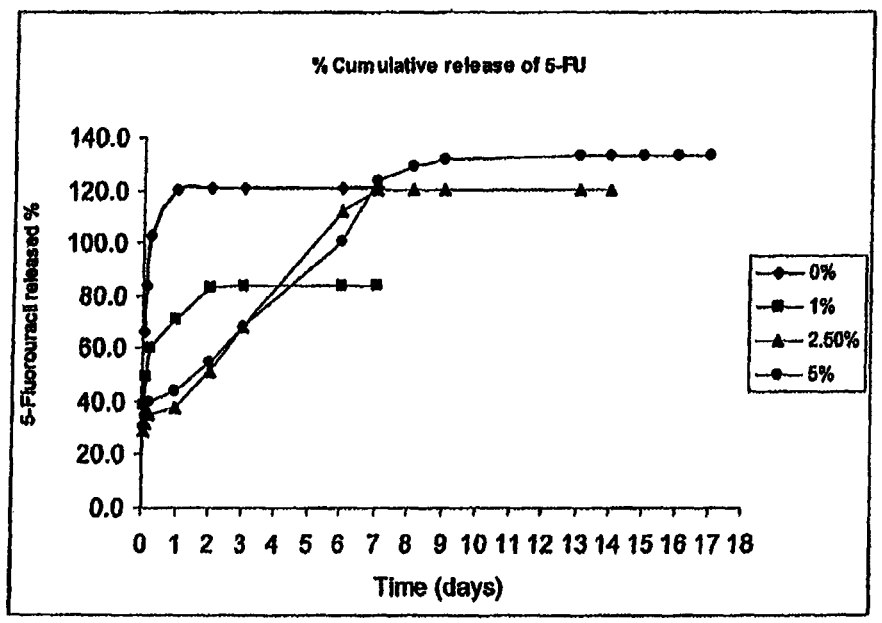
Effect of palmitic acid on the release profile of 5-fluorouracil from a polyurethane sample

COMPOSITIONS AND METHODS FOR COATING MEDICAL IMPLANTS

CROSS-REFERENCE TO RELATED APPLICATIONS

This application is a continuation of U.S. patent application Ser. No. 11/343,714, filed Jan. 31, 2006, which is a continuation of U.S. patent application Ser. No. 10/447,309, filed May 27, 2003, now abandoned, which claims benefit under 35 U.S.C. §119(e) of U.S. Provisional Application Ser. No. 60/383,419, filed May 24, 2002, which applications are incorporated herein by reference in their entirety.

BACKGROUND OF THE INVENTION

1. Technical Field

The present invention relates generally to pharmaceutical compositions, methods, and devices, and more specifically, to compositions and methods which reduce the likelihood of an infection associated with a medical implant.

2. Description of the Related Art

Infections associated with medical implants represent a major healthcare problem. For example, 5% of patients admitted to an acute care facility develop a hospital acquired infection. Hospital acquired infections (nosocomial infections) are the 11$^{th}$ leading cause of death in the US and cost over $2 billion annually. Nosocomial infections directly cause 19,000 deaths per year in the US and contribute to over 58,000 others.

The four most common causes of nosocomial infections are: urinary tract infection (28%); surgical site infection (19%); respiratory tract infection (17%); and bloodstream infection (16% and rising). A significant percentage of these infections are related to bacterial colonization of implanted medical implants such as Foley catheters (urinary tract infections); surgical drains, meshes, sutures, artificial joints, vascular grafts (wound infections); endotracheal and tracheostomy tubes (respiratory tract infection); and vascular infusion catheters (bloodstream infections). Although any infectious agent can infect medical implant, Staphylococci (*S. aureus, S. epidermidis, S. pyogenes*), Enterococci (*E. coli*), Gram Negative Aerobic Bacilli, and *Pseudomonas aeruginosa* are common causes. Once a medical implant becomes colonized by bacteria, it must frequently be replaced resulting in increased morbidity for the patient and increased cost to the healthcare system. Often the infected device serves as a source for a disseminated infection which can lead to significant morbidity or even death.

In an attempt to combat this important clinical problem, devices have been coated with antimicrobial drugs. Representative examples include U.S. Pat. No. 5,520,664 ("Catheter Having a Long-Lasting Antimicrobial Surface Treatment"), U.S. Pat. No. 5,709,672 ("Silastic and Polymer-Based Catheters with Improved Antimicrobial/Antifungal Properties"), U.S. Pat. No. 6,361,526 ("Antimicrobial Tympanostomy Tubes"), U.S. Pat. No. 6,261,271 ("Anti-infective and antithrombogenic medical articles and method for their preparation"), U.S. Pat. No. 5,902,283 ("Antimicrobial impregnated catheters and other medical implants") U.S. Pat. No. 5,624,704 ("Antimicrobial impregnated catheters and other medical implants and method for impregnating catheters and other medical implants with an antimicrobial agent") and U.S. Pat. No. 5,709,672 ("Silastic and Polymer-Based Catheters with Improved Antimicrobial/Antifungal Properties").

One difficulty with these devices, however, is that they can become colonized by bacteria resistant to the antibiotic coating. This can result in at least two distinct clinical problems. First, the device serves as a source of infection in the body with the resulting development of a local or disseminated infection. Secondly, if an infection develops, it cannot be treated with the antibiotic(s) used in the device coating. The development of antibiotic-resistant strains of microbes remains a significant healthcare problem, not just for the infected patient, but also for the healthcare institution in which it develops.

Thus, there is a need in the art for medical implants which have a reduced likelihood of an associated infection. The present invention discloses such devices (as well as compositions and methods for making such devices) which reduce the likelihood of infections in medical implants, and further, provides other, related advantages.

BRIEF DESCRIPTION OF THE DRAWING

FIG. 1 shows the effect of palmitic acid on the release profile of 5-fluorouracil from a polyurethane sample.

BRIEF SUMMARY OF THE INVENTION

Briefly stated, the present invention provides compositions and methods for preventing, reducing or inhibiting the likelihood of infections associated with medical implants. More specifically, within one aspect of the invention medical implants or devices are provided which release a chemotherapeutic agent, wherein the chemotherapeutic agent reduces, inhibits, or prevents the growth or transmission of foreign organisms (e.g., bacteria, fungi, or viruses) which are on or are associated with the medical device or implant. For example, within one aspect of the invention medical implant or devices are provided which release an anthracycline, fluoropyrimidine, folic acid antagonist, podophylotoxin, camptothecin, hydroxyurea, or platinum complex. Within various embodiments, the implant is coated in whole or in part with a composition comprising an anthracycline, fluoropyrimidine, folic acid antagonist, podophylotoxin, camptothecin, hydroxyurea, or platinum complex.

Other aspects of the present invention provide methods for making medical implants, comprising adapting a medical implant (e.g., coating the implant) with an anthracycline, fluoropyrimidine, folic acid antagonist, podophylotoxin, camptothecin, hydroxyurea, or platinum complex. Within certain embodiments, the desired therapeutic agent is coated on and/or released from the medical implant at a dosage and/or concentration which is less than the typical dosage and/or concentration of the agent when used in the treatment of cancer.

A wide variety of medical implants can be generated using the methods provided herein, including for example, catheters (e.g., vascular and dialysis catheters), heart valves, cardiac pacemakers, implantable cardioverter defibrillators, grafts (e.g., vascular grafts), ear, nose, or throat implants, urological implants, endotracheal or tracheostomy tubes, CNS shunts, orthopedic implants, and ocular implants. Within certain embodiments, the catheter (e.g., vascular and dialysis catheters), heart valve, cardiac pacemaker, implantable cardioverter defibrillator, graft (e.g., vascular grafts), ear, nose, or throat implant, urological implant, endotracheal or tracheostomy tube, CNS shunt, orthopedic implant, or ocular implant releases a fluoropyrimide (e.g., 5-FU) at a dosage and/or concentration which is less than a typical dosage and/or concentration which is used for the treatment of cancer.

Within further aspects of the invention, there is provided a catheter which releases an agent selected from the group consisting of an anthracycline, fluoropyrimidine, folic acid antagonist, podophylotoxin, camptothecin, hydroxyurea, or platinum complex. In one embodiment, the catheter releases a fluoropyrimidine and in still another embodiment the fluoropyrimidine is 5-FU. In other embodiments, the catheter further comprises a polymer wherein the agent is released from a polymer on the catheter. In certain embodiments, the catheter has a polymer that is polyurethane or poly(lactide-co-glycolide) (PLG). In related embodiments, the catheter is a vascular catheter or a dialysis catheter. In still other embodiments, the catheter releases an agent that is present on the catheter at a concentration which is less than the typical dosage and/or concentration that is used in the treatment of cancer.

Within further aspects of the invention, there is provided a heart valve which releases an agent selected from the group consisting of an anthracycline, fluoropyrimidine, folic acid antagonist, podophylotoxin, camptothecin, hydroxyurea, or platinum complex. In one embodiment, the heart valve releases a fluoropyrimidine and in still another embodiment the fluoropyrimidine is 5-FU. In other embodiments, the heart valve further comprises a polymer wherein the agent is released from a polymer on the heart valve. In certain embodiments, the heart valve has a polymer that is polyurethane or PLG. In related embodiments, the heart valve is a prosthetic heart valve. In still other embodiments, the heart valve releases an agent that is present on the heart valve at a concentration which is less than the typical dosage and/or concentration that is used in the treatment of cancer.

Within further aspects of the invention, there is provided a cardiac pacemaker which releases an agent selected from the group consisting of an anthracycline, fluoropyrimidine, folic acid antagonist, podophylotoxin, camptothecin, hydroxyurea, or platinum complex. In one embodiment, the cardiac pacemaker releases a fluoropyrimidine and in still another embodiment the fluoropyrimidine is 5-FU. In other embodiments, the cardiac pacemaker further comprises a polymer wherein the agent is released from a polymer on the cardiac pacemaker. In certain embodiments, the cardiac pacemaker has a polymer that is polyurethane or PLG. In still other embodiments, the cardiac pacemaker releases an agent that is present on the cardiac pacemaker at a concentration which is less than the typical dosage and/or concentration that is used in the treatment of cancer.

Within further aspects of the invention, there is provided a implantable cardioverter defibrillator which releases an agent selected from the group consisting of an anthracycline, fluoropyrimidine, folic acid antagonist, podophylotoxin, camptothecin, hydroxyurea, or platinum complex. In one embodiment, the implantable cardioverter defibrillator releases a fluoropyrimidine and in still another embodiment the fluoropyrimidine is 5-FU. In other embodiments, the implantable cardioverter defibrillator further comprises a polymer wherein the agent is released from a polymer on the implantable cardioverter defibrillator. In certain embodiments, the implantable cardioverter defibrillator has a polymer that is polyurethane or PLG. In still other embodiments, the implantable cardioverter defibrillator releases an agent that is present on the implantable cardioverter defibrillator at a concentration which is less than the typical dosage and/or concentration that is used in the treatment of cancer.

Within further aspects of the invention, there is provided a graft which releases an agent selected from the group consisting of an anthracycline, fluoropyrimidine, folic acid antagonist, podophylotoxin, camptothecin, hydroxyurea, or platinum complex. In one embodiment, the graft releases a fluoropyrimidine and in still another embodiment the fluoropyrimidine is 5-FU. In other embodiments, the graft further comprises a polymer wherein the agent is released from a polymer on the graft. In certain embodiments, the graft has a polymer that is polyurethane or PLG. In related embodiments, the graft is a vascular graft or a hemodialysis access graft. In still other embodiments, the graft releases an agent that is present on the graft at a concentration which is less than the typical dosage and/or concentration that is used in the treatment of cancer.

Within further aspects of the invention, there is provided a ear, nose, or throat implant which releases an agent selected from the group consisting of an anthracycline, fluoropyrimidine, folic acid antagonist, podophylotoxin, camptothecin, hydroxyurea, or platinum complex. In one embodiment, the ear, nose, or throat implant releases a fluoropyrimidine and in still another embodiment the fluoropyrimidine is 5-FU. In other embodiments, the ear, nose, or throat implant further comprises a polymer wherein the agent is released from a polymer on the ear, nose, or throat implant. In certain embodiments, the ear, nose, or throat implant has a polymer that is polyurethane or PLG. In related embodiments, the ear, nose, or throat implant is a tympanostomy tube or a sinus stent. In still other embodiments, the ear, nose, or throat implant releases an agent that is present on the ear, nose, or throat implant at a concentration which is less than the typical dosage and/or concentration that is used in the treatment of cancer.

Within further aspects of the invention, there is provided a urological implant which releases an agent selected from the group consisting of an anthracycline, fluoropyrimidine, folic acid antagonist, podophylotoxin, camptothecin, hydroxyurea, or platinum complex. In one embodiment, the urological implant releases a fluoropyrimidine and in still another embodiment the fluoropyrimidine is 5-FU. In other embodiments, the urological implant further comprises a polymer wherein the agent is released from a polymer on the urological implant. In certain embodiments, the urological implant has a polymer that is polyurethane or PLG. In related embodiments, the urological implant is a urinary catheter, ureteral stent, urethral stent, bladder sphincter, or penile implant. In still other embodiments, the urological implant releases an agent that is present on the urological implant at a concentration which is less than the typical dosage and/or concentration that is used in the treatment of cancer.

Within further aspects of the invention, there is provided a endotracheal or tracheostomy tube which releases an agent selected from the group consisting of an anthracycline, fluoropyrimidine, folic acid antagonist, podophylotoxin, camptothecin, hydroxyurea, or platinum complex. In one embodiment, the endotracheal or tracheostomy tube releases a fluoropyrimidine and in still another embodiment the fluoropyrimidine is 5-FU. In other embodiments, the endotracheal or tracheostomy tube further comprises a polymer wherein the agent is released from a polymer on the endotracheal or tracheostomy tube. In certain embodiments, the endotracheal or tracheostomy tube has a polymer that is polyurethane or PLG. In still other embodiments, the endotracheal or tracheostomy tube releases an agent that is present on the endotracheal or tracheostomy tube at a concentration which is less than the typical dosage and/or concentration that is used in the treatment of cancer.

Within further aspects of the invention, there is provided a CNS shunt which releases an agent selected from the group consisting of an anthracycline, fluoropyrimidine, folic acid antagonist, podophylotoxin, camptothecin, hydroxyurea, or platinum complex. In one embodiment, the CNS shunt releases a fluoropyrimidine and in still another embodiment the fluoropyrimidine is 5-FU. In other embodiments, the CNS shunt further comprises a polymer wherein the agent is released from a polymer on the CNS shunt. In certain embodiments, the CNS shunt has a polymer that is polyurethane or PLG. In related embodiments, the CNS shunt is a ventriculopleural shunt, a VA shunt, or a VP shunt. In still other embodiments, the CNS shunt releases an agent that is present on the CNS shunt at a concentration which is less than the typical dosage and/or concentration that is used in the treatment of cancer.

Within further aspects of the invention, there is provided a orthopedic implant which releases an agent selected from the group consisting of an anthracycline, fluoropyrimidine, folic acid antagonist, podophylotoxin, camptothecin, hydroxyurea, or platinum complex. In one embodiment, the orthopedic implant releases a fluoropyrimidine and in still another embodiment the fluoropyrimidine is 5-FU. In other embodiments, the orthopedic implant further comprises a polymer wherein the agent is released from a polymer on the orthopedic implant. In certain embodiments, the orthopedic implant has a polymer that is polyurethane or PLG. In related embodiments, the orthopedic implant is a prosthetic joint or fixation device. In still other embodiments, the orthopedic implant releases an agent that is present on the orthopedic implant at a concentration which is less than the typical dosage and/or concentration that is used in the treatment of cancer.

Within further aspects of the invention, there is provided a ocular implant which releases an agent selected from the group consisting of an anthracycline, fluoropyrimidine, folic acid antagonist, podophylotoxin, camptothecin, hydroxyurea, or platinum complex. In one embodiment, the ocular implant releases a fluoropyrimidine and in still another embodiment the fluoropyrimidine is 5-FU. In other embodiments, the ocular implant further comprises a polymer wherein the agent is released from a polymer on the ocular implant. In certain embodiments, the ocular implant has a polymer that is polyurethane or PLG. In related embodiments, the ocular implant is an intraocular lens or a contact lens. In still other embodiments, the ocular implant releases an agent that is present on the ocular implant at a concentration which is less than the typical dosage and/or concentration that is used in the treatment of cancer.

Within other aspects of the invention, compositions are provided comprising a polymer and an anthracycline, fluoropyrimidine, folic acid antagonist, podophylotoxin, camptothecin, hydroxyurea, or platinum complex, wherein said anthracycline, fluoropyrimidine, folic acid antagonist, podophylotoxin, camptothecin, hydroxyurea, or platinum complex is present in said composition at a concentration of less than any one of $10^{-4}$ M, $10^{-5}$ M, $10^{-6}$ M, or, $10^{-7}$ M.

Also provided methods for reducing or inhibiting infection associated with a medical implant, comprising the step of introducing a medical implant into a patient which has been coated with an anthracycline, fluoropyrimidine, folic acid antagonist, podophylotoxin, camptothecin, hydroxyurea, or platinum complex.

Within various embodiments of the above, the anthracycline is doxorubicin or mitoxantrone, the fluoropyrimidine is 5-fluorouracil, the folic acid antagonist is methotrexate, and the podophylotoxin is etoposide. Within further embodiments the composition further comprises a polymer.

These and other aspects of the present invention will become evident upon reference to the following detailed description and attached drawings. In addition, various references are set forth herein which describe in more detail certain procedures or compositions (e.g., compounds or agents and methods for making such compounds or agents, etc.), and are therefore incorporated by reference in their entirety. When PCT applications are referred to it is also understood that the underlying or cited U.S. applications are also incorporated by reference herein in their entirety.

DETAILED DESCRIPTION OF THE INVENTION

Prior to setting forth the invention, it may be helpful to an understanding thereof to set forth definitions of certain terms that will be used hereinafter.

"Medical implant" refers to devices or objects that are implanted or inserted into a body. Representative examples include vascular catheters, prosthetic heart valves, cardiac pacemakers, implantable cardioverter defibrillators, vascular grafts, ear, nose, or throat implants, urological implants, endotracheal or tracheostomy tubes, dialysis catheters, CNS shunts, orthopedic implants, and ocular implants.

As used herein, the term "about" or "consists essentially of" refers to ±15% of any indicated structure, value, or range. Any numerical ranges recited herein are to be understood to include any integer within the range and, where applicable (e.g., concentrations), fractions thereof, such as one tenth and one hundredth of an integer (unless otherwise indicated).

Briefly, as noted above, the present invention discloses medical implants (as well as compositions and methods for making medical implants) which reduce the likelihood of infections in medical implants. More specifically, as noted above, infection is a common complication of the implantation of foreign bodies such as medical devices. Foreign materials provide an ideal site for micro-organisms to attach and colonize. It is also hypothesized that there is an impairment of host defenses to infection in the microenvironment surrounding a foreign material. These factors make medical implants particularly susceptible to infection and make eradication of such an infection difficult, if not impossible, in most cases.

Medical implant failure as a result of infection, with or without the need to replace the implant, results in significant morbidity, mortality and cost to the healthcare system. Since there is a wide array of infectious agents capable of causing medical implant infections, there exists a significant unmet need for therapies capable of inhibiting the growth of a diverse spectrum of bacteria and fungi on implantable devices. The present invention meets this need by providing drugs that can be released from an implantable device, and which have potent antimicrobial activity at extremely low doses. Further, these agents have the added advantage that should resistance develop to the chemotherapeutic agent, the drug utilized in the coating would not be one which would be used to combat the subsequent infection (i.e., if bacterial resistance developed it would be to an agent that is not used as an antibiotic).

Discussed in more detail below are (I) Agents; (II) Compositions and Formulations; (III) Devices, and (IV) Clinical Applications.

I. Agents

Briefly, a wide variety of agents (also referred to herein as 'therapeutic agents' or 'drugs') can be utilized within the context of the present invention, either with or without a carrier (e.g., a polymer; see section II below). Discussed in more detail below are (A) Anthracyclines (e.g., doxorubicin and mitoxantrone), (B) Fluoropyrimidines (e.g., 5-FU), (C) Folic acid antagonists (e.g., methotrexate), (D) Podophylotoxins (e.g., etoposide), (E) Camptothecins, (F) Hydroxyureas, and (G) Platinum complexes (e.g., cisplatin).

A. Anthracyclines

Anthracyclines have the following general structure, where the R groups may be a variety of organic groups:

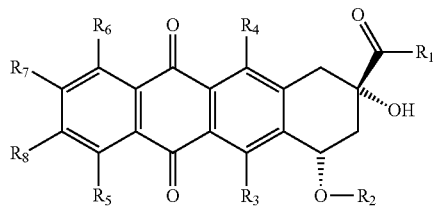

According to U.S. Pat. No. 5,594,158, suitable R groups are as follows: $R_1$ is $CH_3$ or $CH_2OH$; $R_2$ is daunosamine or H; $R_3$ and $R_4$ are independently one of OH, $NO_2$, $NH_2$, F, Cl, Br, I, CN, H or groups derived from these; $R_5$ is hydrogen, hydroxy, or methoxy; and $R_{6-8}$ are all hydrogen. Alternatively, $R_5$ and $R_6$ are hydrogen and $R_7$ and $R_8$ are alkyl or halogen, or vice versa.

According to U.S. Pat. No. 5,843,903, $R_1$ may be a conjugated peptide. According to U.S. Pat. No. 4,296,105, $R_5$ may be an ether linked alkyl group. According to U.S. Pat. No. 4,215,062, $R_5$ may be OH or an ether linked alkyl group. $R_1$ may also be linked to the anthracycline ring by a group other than C(O), such as an alkyl or branched alkyl group having the C(O) linking moiety at its end, such as —$CH_2CH(CH_2$—X)C(O)—$R_1$, wherein X is H or an alkyl group (see, e.g., U.S. Pat. No. 4,215,062). $R_2$ may alternately be a group linked by the functional group =N—NHC(O)—Y, where Y is a group such as a phenyl or substituted phenyl ring. Alternately $R_3$ may have the following structure:

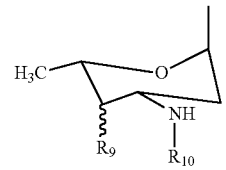

in which $R_9$ is OH either in or out of the plane of the ring, or is a second sugar moiety such as $R_3$. $R_{10}$ may be H or form a secondary amine with a group such as an aromatic group, saturated or partially saturated 5 or 6 membered heterocyclic having at least one ring nitrogen (see U.S. Pat. No. 5,843,903). Alternately, $R_{10}$ may be derived from an amino acid, having the structure —C(O)CH(NHR$_{11}$)(R$_{12}$), in which $R_{11}$ is H, or forms a $C_{3-4}$ membered alkylene with $R_{12}$. $R_{12}$ may be H, alkyl, aminoalkyl, amino, hydroxy, mercapto, phenyl, benzyl or methylthio (see U.S. Pat. No. 4,296,105).

Exemplary anthracyclines are Doxorubicin, Daunorubicin, Idarubicin, Epirubicin, Pirarubicin, Zorubicin, and Carubicin. Suitable compounds have the structures:

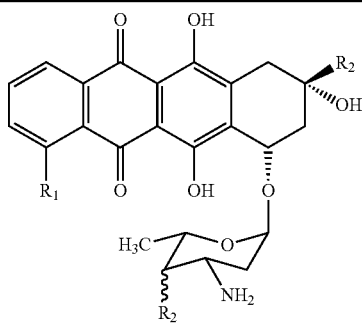

| | $R_1$ | $R_2$ | $R_3$ |
|---|---|---|---|
| Doxorubicin: | $OCH_3$ | $C(O)CH_2OH$ | OH out of ring plane |
| Epirubicin: (4' epimer of doxorubicin) | $OCH_3$ | $C(O)CH_2OH$ | OH in ring plane |
| Daunorubicin: | $OCH_3$ | $C(O)CH_3$ | OH out of ring plane |
| Idarubicin: | H | $C(O)CH_3$ | OH out of ring plane |
| Pirarubicin: | $OCH_3$ | $C(O)CH_2OH$ | 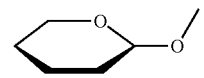 |
| Zorubicin: | $OCH_3$ | $C(CH_3)(=N)NHC(O)C_6H_5$ | OH |
| Carubicin: | OH | $C(O)CH_3$ | OH out of ring plane |

Other suitable anthracyclines are Anthramycin, Mitoxantrone, Menogaril, Nogalamycin, Aclacinomycin A, Olivomycin A, Chromomycin $A_3$, and Plicamycin having the structures:

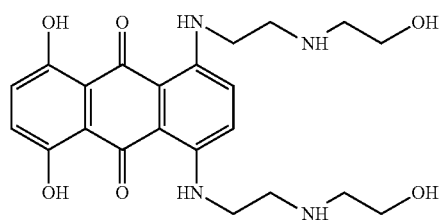
Mitoxantrone
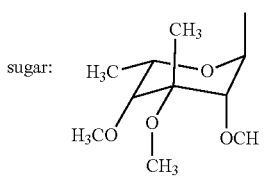
|  | R₁ | R₂ | R₃ |
|---|---|---|---|
| Menogaril | H | OCH₃ | H |
| Nogalamycin | O-sugar | H | COOCH₃ |
sugar:
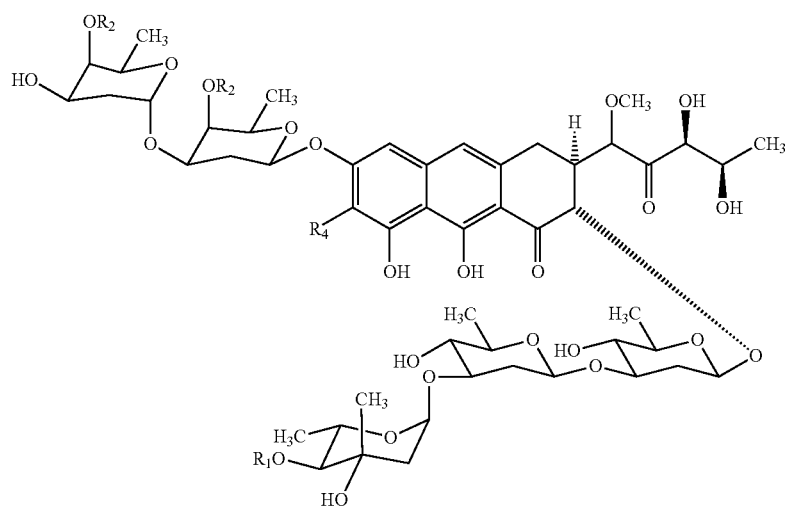
|  | R₁ | R₂ | R₃ | R₄ |
|---|---|---|---|---|
| Olivomycin A | COCH(CH₃)₂ | CH₃ | COCH₃ | H |
| Chromomycin A₃ | COCH₃ | CH₃ | COCH₃ | CH₃ |
| Plicamycin | H | H | H | CH₃ |

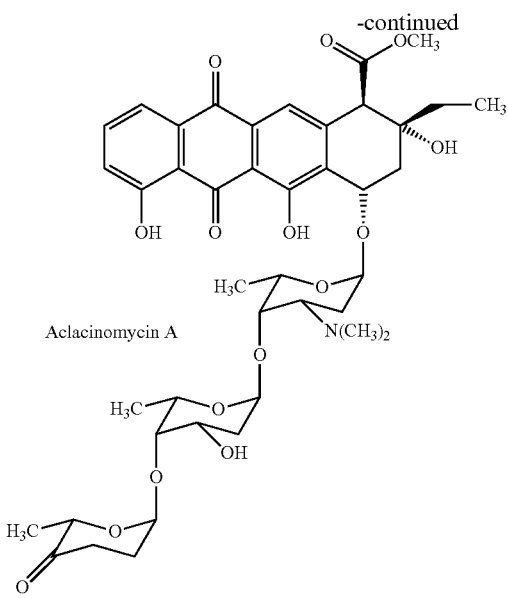

Aclacinomycin A

Other representative anthracyclines include, FCE 23762 doxorubicin derivative (Quaglia et al., *J. Liq. Chromatogr.* 17(18):3911-3923, 1994), annamycin (Zou et al., *J. Pharm. Sci.* 82(11):1151-1154, 1993), ruboxyl (Rapoport et al., *J. Controlled Release* 58(2):153-162, 1999), anthracycline disaccharide doxorubicin analogue (Pratesi et al., *Clin. Cancer Res.* 4(11):2833-2839, 1998), N-(trifluoroacetyl)doxorubicin and 4'-O-acetyl-N-(trifluoroacetyl)doxorubicin (Berube & Lepage, *Synth. Commun.* 28(6):1109-1116, 1998), 2-pyrrolinodoxorubicin (Nagy et al., *Proc. Nat'l Acad. Sci. U.S.A.* 95(4):1794-1799, 1998), disaccharide doxorubicin analogues (Arcamone et al., *J. Nat'l Cancer Inst.* 89(16):1217-1223, 1997), 4-demethoxy-7-O-[2,6-dideoxy-4-O-(2,3,6-trideoxy-3-amino-α-L-lyxo-hexopyranosyl)-α-L-lyxo-hexopyranosyl]adriamicinone doxorubicin disaccharide analog (Monteagudo et al., *Carbohydr. Res.* 300(1):11-16, 1997), 2-pyrrolinodoxorubicin (Nagy et al., *Proc. Nat'l Acad. Sci. U.S.A.* 94(2):652-656, 1997), morpholinyl doxorubicin analogues (Duran et al., *Cancer Chemother. Pharmacol.* 38(3):210-216, 1996), enaminomalonyl-β-alanine doxorubicin derivatives (Seitz et al., *Tetrahedron Lett.* 36(9):1413-16, 1995), cephalosporin doxorubicin derivatives (Vrudhula et al., *J. Med. Chem.* 38(8):1380-5, 1995), hydroxyrubicin (Solary et al., *Int. J. Cancer* 58(1):85-94, 1994), methoxymorpholino doxorubicin derivative (Kuhl et al., *Cancer Chemother. Pharmacol.* 33(1):10-16, 1993), (6-maleimidocaproyl)hydrazone doxorubicin derivative (Willner et al., *Bioconjugate Chem.* 4(6):521-7, 1993), N-(5,5-diacetoxypent-1-yl) doxorubicin (Cherif & Farquhar, *J. Med. Chem.* 35(17):3208-14, 1992), FCE 23762 methoxymorpholinyl doxorubicin derivative (Ripamonti et al., *Br. J. Cancer* 65(5):703-7, 1992), N-hydroxysuccinimide ester doxorubicin derivatives (Demant et al., *Biochim. Biophys. Acta* 1118(1):83-90, 1991), polydeoxynucleotide doxorubicin derivatives (Ruggiero et al., *Biochim. Biophys. Acta* 1129(3):294-302, 1991), morpholinyl doxorubicin derivatives (EPA 434960), mitoxantrone doxorubicin analogue (Krapcho et al., *J. Med. Chem.* 34(8):2373-80. 1991), AD198 doxorubicin analogue (Traganos et al., *Cancer Res.* 51(14):3682-9, 1991), 4-demethoxy-3'-N-trifluoroacetyldoxorubicin (Horton et al., *Drug Des. Delivery* 6(2):123-9, 1990), 4'-epidoxorubicin (Drzewoski et al., *Pol. J. Pharmacol. Pharm.* 40(2):159-65, 1988; Weenen et al., *Eur. J. Cancer Clin. Oncol.* 20(7):919-26, 1984), alkylating cyanomorpholino doxorubicin derivative (Scudder et al., *J. Nat'l Cancer Inst.* 80(16):1294-8, 1988), deoxydihydroiodooxorubicin (EPA 275966), adriblastin (Kalishevskaya et al., *Vestn. Mosk. Univ.,* 16(Biol. 1):21-7, 1988), 4'-deoxydoxorubicin (Schoelzel et al., *Leuk. Res.* 10(12):1455-9, 1986), 4-demethyoxy-4'-o-methyldoxorubicin (Giuliani et al., *Proc. Int. Congr. Chemother.* 16:285-70-285-77, 1983), 3'-deamino-3'-hydroxydoxorubicin (Horton et al., *J. Antibiot.* 37(8):853-8, 1984), 4-demethyoxy doxorubicin analogues (Barbieri et al., *Drugs Exp. Clin. Res.* 10(2):85-90, 1984), N-L-leucyl doxorubicin derivatives (Trouet et al., Anthracyclines (*Proc. Int. Symp. Tumor Pharmacother.*), 179-81, 1983), 3'-deamino-3'-(4-methoxy-1-piperidinyl) doxorubicin derivatives (U.S. Pat. No. 4,314,054), 3'-deamino-3'-(4-mortholinyl) doxorubicin derivatives (U.S. Pat. No. 4,301,277), 4'-deoxydoxorubicin and 4'-o-methyldoxorubicin (Giuliani et al., *Int. J. Cancer* 27(1):5-13, 1981), aglycone doxorubicin derivatives (Chan & Watson, *J. Pharm. Sci.* 67(12):1748-52, 1978), SM 5887 (*Pharma Japan* 1468:20, 1995), MX-2 (*Pharma Japan* 1420:19, 1994), 4'-deoxy-13(S)-dihydro-4'-iododoxorubicin (EP 275966), morpholinyl doxorubicin derivatives (EPA 434960), 3'-deamino-3'-(4-methoxy-1-piperidinyl) doxorubicin derivatives (U.S. Pat. No. 4,314,054), doxorubicin-14-valerate, morpholinodoxorubicin (U.S. Pat. No. 5,004,606), 3'-deamino-3'-(3"-cyano-4"-morpholinyl doxorubicin; 3'-deamino-3'-(3"-cyano-4"-morpholinyl)-13-dihydroxorubicin; (3'-deamino-3'-(3"-cyano-4"-morpholinyl) daunorubicin; 3'-deamino-3'-(3"-cyano-4"-morpholinyl)-3-dihydrodaunorubicin; and 3'-deamino-3'-(4"-morpholinyl-5-iminodoxorubicin and derivatives (U.S. Pat. No. 4,585,859), 3'-deamino-3'-(4-methoxy-1-piperidinyl) doxorubicin derivatives (U.S. Pat. No. 4,314,054) and 3-deamino-3-(4-morpholinyl) doxorubicin derivatives (U.S. Pat. No. 4,301,277).

B. Fluoropyrimidine Analogs

In another aspect, the therapeutic agent is a fluoropyrimidine analog, such as 5-fluorouracil, or an analog or derivative thereof, including Carmofur, Doxifluridine, Emitefur, Tegafur, and Floxuridine. Exemplary compounds have the structures:

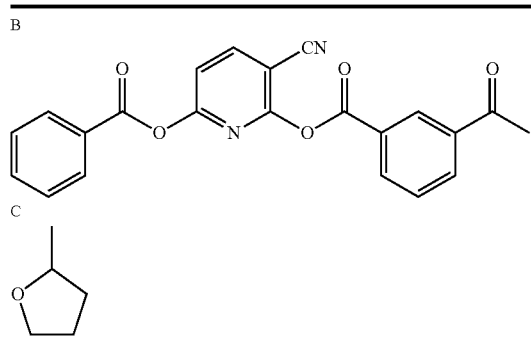

| | R₁ | R₂ |
|---|---|---|
| 5-Fluorouracil | H | H |
| Carmofur | C(O)NH(CH₂)₅CH₃ | H |
| Doxifluridine | A₁ | H |
| Floxuridine | A₂ | H |
| Emitefur | CH₂OCH₂CH₃ | B |
| Tegafur | C | H |

B

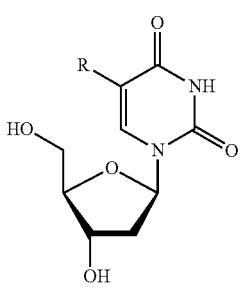

C

Other suitable fluoropyrimidine analogs include 5-FudR (5-fluoro-deoxyuridine), or an analog or derivative thereof, including 5-iododeoxyuridine (5-IudR), 5-bromodeoxyuridine (5-BudR), Fluorouridine triphosphate (5-FUTP), and Fluorodeoxyuridine monophosphate (5-dFUMP). Exemplary compounds have the structures:

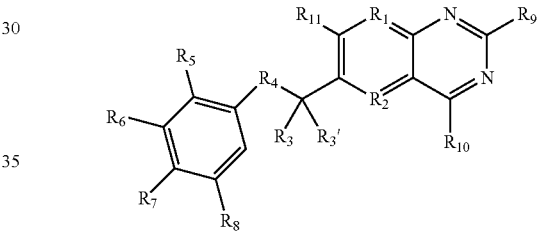

5-Fluoro-2'-deoxyuridine: R=F
5-Bromo-2'-deoxyuridine: R=Br
5-Iodo-2'-deoxyuridine: R=I Other representative examples of fluoropyrimidine analogs include N3-alkylated analogues of 5-fluorouracil (Kozai et al., *J. Chem. Soc., Perkin Trans.* 1(19):3145-3146, 1998), 5-fluorouracil derivatives with 1,4-oxaheteroepane moieties (Gomez et al., *Tetrahedron* 54(43):13295-13312, 1998), 5-fluorouracil and nucleoside analogues (Li, *Anticancer Res.* 17(1A):21-27, 1997), cis- and trans-5-fluoro-5,6-dihydro-6-alkoxyuracil (Van der Wilt et al., *Br. J. Cancer* 68(4):702-7, 1993), cyclopentane 5-fluorouracil analogues (Hronowski & Szarek, *Can. J. Chem.* 70(4):1162-9, 1992), A-OT-fluorouracil (Zhang et al., *Zongguo Yiyao Gongye Zazhi* 20(11):513-15, 1989), N4-trimethoxybenzoyl-5'-deoxy-5-fluorocytidine and 5'-deoxy-5-fluorouridine (Miwa et al., *Chem. Pharm. Bull.* 38(4):998-1003, 1990), 1-hexylcarbamoyl-5-fluorouracil (Hoshi et al., *J. Pharmacobio-Dun.* 3(9):478-81, 1980; Maehara et al., *Chemotherapy* (Basel) 34(6):484-9, 1988), B-3839 (Prajda et al., *In Vivo* 2(2):151-4, 1988), uracil-1-(2-tetrahydrofuryl)-5-fluorouracil (Anai et al., *Oncology* 45(3): 144-7, 1988), 1-(2'-deoxy-2'-fluoro-β-D-arabinofuranosyl)-5-fluorouracil (Suzuko et al., *Mol. Pharmacol.* 31(3):301-6, 1987), doxifluridine (Matuura et al., *Oyo Yakuri* 29(5):803-31, 1985), 5'-deoxy-5-fluorouridine (Bollag & Hartmann, *Eur. J. Cancer* 16(4):427-32, 1980), 1-acetyl-3-O-toluoyl-5-fluorouracil (Okada, *Hiroshima J. Med. Sci.* 28(1):49-66, 1979), 5-fluorouracil-m-formylbenzene-sulfonate (JP 55059173), N'-(2-furanidyl)-5-fluorouracil (JP 53149985) and 1-(2-tetrahydrofuryl)-5-fluorouracil (JP 52089680).

These compounds are believed to function as therapeutic agents by serving as antimetabolites of pyrimidine.

C. Folic Acid Antagonists

In another aspect, the therapeutic agent is a folic acid antagonist, such as Methotrexate or derivatives or analogs thereof, including Edatrexate, Trimetrexate, Raltitrexed, Piritrexim, Denopterin, Tomudex, and Pteropterin. Methotrexate analogs have the following general structure:

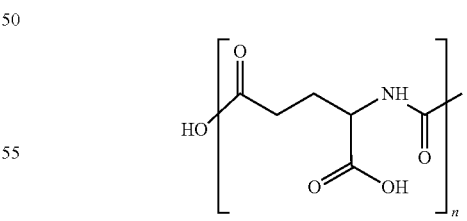

The identity of the R group may be selected from organic groups, particularly those groups set forth in U.S. Pat. Nos. 5,166,149 and 5,382,582. For example, $R_1$ may be N, $R_2$ may be N or $C(CH_3)$, $R_3$ and $R_3'$ may H or alkyl, e.g., $CH_3$, $R_4$ may be a single bond or NR, where R is H or alkyl group. $R_{5,6,8}$ may be H, $OCH_3$, or alternately they can be halogens or hydro groups. $R_7$ is a side chain of the general structure:

wherein n=1 for methotrexate, n=3 for pteropterin. The carboxyl groups in the side chain may be esterified or form a salt such as a $Zn^{2+}$ salt. $R_9$ and $R_{10}$ can be $NH_2$ or may be alkyl substituted.

Exemplary folic acid antagonist compounds have the structures:

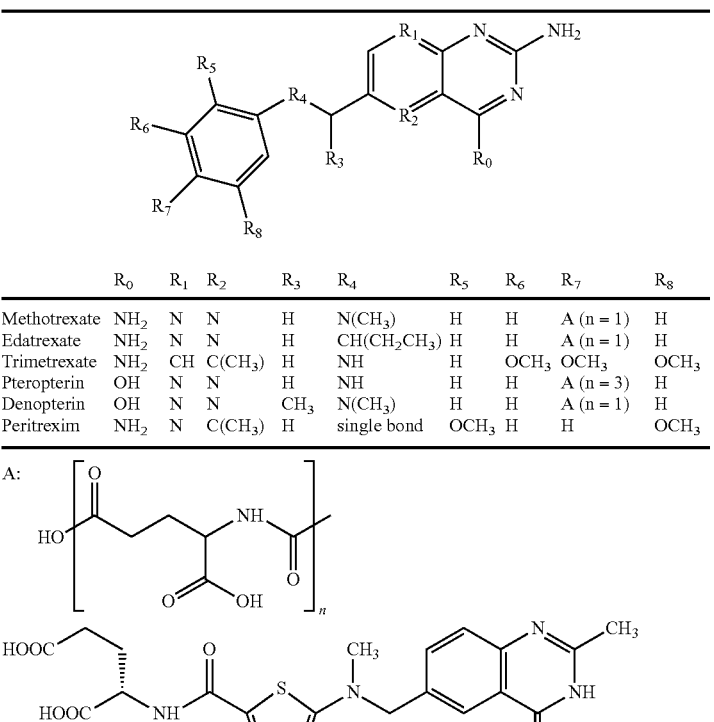

| | $R_0$ | $R_1$ | $R_2$ | $R_3$ | $R_4$ | $R_5$ | $R_6$ | $R_7$ | $R_8$ |
|---|---|---|---|---|---|---|---|---|---|
| Methotrexate | $NH_2$ | N | N | H | $N(CH_3)$ | H | H | A (n = 1) | H |
| Edatrexate | $NH_2$ | N | N | H | $CH(CH_2CH_3)$ | H | H | A (n = 1) | H |
| Trimetrexate | $NH_2$ | CH | $C(CH_3)$ | H | NH | H | $OCH_3$ | $OCH_3$ | $OCH_3$ |
| Pteropterin | OH | N | N | H | NH | H | H | A (n = 3) | H |
| Denopterin | OH | N | N | $CH_3$ | $N(CH_3)$ | H | H | A (n = 1) | H |
| Peritrexim | $NH_2$ | N | $C(CH_3)$ | H | single bond | $OCH_3$ | H | H | $OCH_3$ |

Tomudex

Other representative examples include 6-S-aminoacyloxymethyl mercaptopurine derivatives (Harada et al., Chem. Pharm. Bull. 43(10):793-6, 1995), 6-mercaptopurine (6-MP) (Kashida et al., Biol. Pharm. Bull. 18(11):1492-7, 1995), 7,8-polymethyleneimidazo-1,3,2-diazaphosphorines (Nilov et al., Mendeleev Commun. 2:67, 1995), azathioprine (Chifotides et al., J. Inorg. Biochem. 56(4):249-64, 1994), methyl-D-glucopyranoside mercaptopurine derivatives (Da Silva et al., Eur. J. Med. Chem. 29(2):149-52, 1994) and s-alkynyl mercaptopurine derivatives (Ratsino et al., Khim.-Farm. Zh. 15(8):65-7, 1981); indoline ring and a modified ornithine or glutamic acid-bearing methotrexate derivatives (Matsuoka et al., Chem. Pharm. Bull. 45(7):1146-1150, 1997), alkyl-substituted benzene ring C bearing methotrexate derivatives (Matsuoka et al., Chem. Pharm. Bull. 44(12):2287-2293, 1996), benzoxazine or benzothiazine moiety-bearing methotrexate derivatives (Matsuoka et al., J. Med. Chem. 40(1): 105-111, 1997), 10-deazaminopterin analogues (DeGraw et al., J. Med. Chem. 40(3):370-376, 1997), 5-deazaminopterin and 5,10-dideazaminopterin methotrexate analogues (Piper et al., J. Med. Chem. 40(3):377-384, 1997), indoline moiety-bearing methotrexate derivatives (Matsuoka et al., Chem. Pharm. Bull. 44(7):1332-1337, 1996), lipophilic amide methotrexate derivatives (Pignatello et al., World Meet. Pharm., Biopharm. Pharm. Technol., 563-4, 1995), L-threo-(2S,4S)-4-fluoroglutamic acid and DL-3,3-difluoroglutamic acid-containing methotrexate analogues (Hart et al., J. Med. Chem. 39(1):56-65, 1996), methotrexate tetrahydroquinazoline analogue (Gangjee, et al., J. Heterocycl. Chem. 32(1): 243-8, 1995), N-(α-aminoacyl)methotrexate derivatives (Cheung et al., Pteridines 3(1-2):101-2, 1992), biotin methotrexate derivatives (Fan et al., Pteridines 3(1-2):131-2, 1992), D-glutamic acid or D-erythrou, threo-4-fluoroglutamic acid methotrexate analogues (McGuire et al., Biochem. Pharmacol. 42(12):2400-3, 1991), β,γ-methano methotrexate analogues (Rosowsky et al., Pteridines 2(3):133-9, 1991), 10-deazaminopterin (10-EDAM) analogue (Braakhuis et al., Chem. Biol. Pteridines, Proc. Int. Symp. Pteridines Folic Acid Deriv., 1027-30, 1989), γ-tetrazole methotrexate analogue (Kalman et al., Chem. Biol. Pteridines, Proc. Int. Symp. Pteridines Folic Acid Deriv., 1154-7, 1989), N-(L-α-aminoacyl)methotrexate derivatives (Cheung et al., Heterocycles 28(2):751-8, 1989), meta and ortho isomers of aminopterin (Rosowsky et al., J. Med. Chem. 32(12):2582, 1989), hydroxymethylmethotrexate (DE 267495), γ-fluoromethotrexate (McGuire et al., Cancer Res. 49(16):4517-25, 1989), polyglutamyl methotrexate derivatives (Kumar et al., Cancer Res. 46(10):5020-3, 1986), gem-diphosphonate methotrexate analogues (WO 88/06158), α- and γ-substituted methotrexate analogues (Tsushima et al., Tetrahedron 44(17):5375-87, 1988), 5-methyl-5-deaza methotrexate analogues (U.S. Pat. No. 4,725,687), Nδ-acyl-Nα-(4-amino-4-deoxypteroyl)-L-ornithine derivatives (Rosowsky et al., J. Med. Chem. 31(7):1332-7, 1988), 8-deaza methotrexate analogues (Kuehl et al., Cancer Res. 48(6):1481-8, 1988), acivicin methotrexate analogue (Rosowsky et al., J. Med. Chem. 30(8):1463-9, 1987), polymeric platinol methotrexate derivative (Carraher et al., Polym. Sci. Technol. (Plenum), 35(Adv. Biomed. Polym.):311-24, 1987), methotrexate-γ-dimyristoylphophatidylethanolamine (Kinsky et al., Biochim. Biophys. Acta 917(2):211-18, 1987), methotrexate polyglutamate analogues (Rosowsky et al., Chem. Biol. Pteridines, Pteridines Folid Acid Deriv., Proc. Int. Symp. Pteridines Folid Acid Deriv.: Chem., Biol. Clin. Aspects: 985-8, 1986), poly-γ-glutamyl methotrexate derivatives (Kisliuk et al., Chem. Biol. Pteridines, Pteridines Folid Acid Deriv., Proc. Int. Symp. Pteridines Folid Acid Deriv.: Chem., Biol. Clin. Aspects: 989-92, 1986), deoxyuridylate methotrexate derivatives (Webber et al., Chem. Biol. Pteridines, Pteridines Folid Acid Deriv., Proc. Int. Symp. Pteridines Folid Acid Deriv.: Chem., Biol. Clin. Aspects: 659-62, 1986), iodoacetyl lysine methotrexate analogue (Delcamp et al., Chem. Biol. Pteridines, Pteridines Folid Acid Deriv., Proc. Int. Symp. Pteridines Folid Acid Deriv.: Chem., Biol. Clin. Aspects: 807-9, 1986), 2,.omega.-diaminoalkanoid acid-containing methotrexate analogues (McGuire et al., *Biochem. Pharmacol.* 35(15):2607-13, 1986), polyglutamate methotrexate derivatives (Kamen & Winick, *Methods Enzymol.* 122 (Vitam. Coenzymes, Pt. G):339-46, 1986), 5-methyl-5-deaza analogues (Piper et al., *J. Med. Chem.* 29(6):1080-7, 1986), quinazoline methotrexate analogue (Mastropaolo et al., *J. Med. Chem.* 29(1):155-8, 1986), pyrazine methotrexate analogue (Lever & Vestal, *J. Heterocycl. Chem.* 22(1):5-6, 1985), cysteic acid and homocysteic acid methotrexate analogues (U.S. Pat. No. 4,490,529), γ-tert-butyl methotrexate esters (Rosowsky et al., *J. Med. Chem.* 28(5):660-7, 1985), fluorinated methotrexate analogues (Tsushima et al., *Heterocycles* 23(1):45-9, 1985), folate methotrexate analogue (Trombe, *J. Bacteriol.* 160(3):849-53, 1984), phosphonoglutamic acid analogues (Sturtz & Guillamot, *Eur. J. Med. Chem.—Chim. Ther.* 19(3):267-73, 1984), poly (L-lysine) methotrexate conjugates (Rosowsky et al., *J. Med. Chem.* 27(7):888-93, 1984), dilysine and trilysine methotrexate derivates (Forsch & Rosowsky, *J. Org. Chem.* 49(7):1305-9, 1984), 7-hydroxymethotrexate (Fabre et al., *Cancer Res.* 43(10):4648-52, 1983), poly-γ-glutamyl methotrexate analogues (Piper & Montgomery, *Adv. Exp. Med. Biol., 163 (Folyl Antifolyl Polyglutamates)*:95-100, 1983), 3',5'-dichloromethotrexate (Rosowsky & Yu, *J. Med. Chem.* 26(10):1448-52, 1983), diazoketone and chloromethylketone methotrexate analogues (Gangjee et al., *J. Pharm. Sci.* 71(6):717-19, 1982), 10-propargylaminopterin and alkyl methotrexate homologs (Piper et al., *J. Med. Chem.* 25(7):877-80, 1982), lectin derivatives of methotrexate (Lin et al., *JNCI* 66(3):523-8, 1981), polyglutamate methotrexate derivatives (Galivan, *Mol. Pharmacol.* 17(1):105-10, 1980), halogentated methotrexate derivatives (Fox, *JNCI* 58(4):J955-8, 1977), 8-alkyl-7, 8-dihydro analogues (Chaykovsky et al., *J. Med. Chem.* 20(10):J1323-7, 1977), 7-methyl methotrexate derivatives and dichloromethotrexate (Rosowsky & Chen, *J. Med. Chem.* 17(12):J1308-11, 1974), lipophilic methotrexate derivatives and 3',5'-dichloromethotrexate (Rosowsky, *J. Med. Chem.* 16(10):J 1190-3, 1973), deaza amethopterin analogues (Montgomery et al., *Ann. N.Y. Acad. Sci.* 186:J227-34, 1971), MX068 (Pharma Japan, 1658:18, 1999) and cysteic acid and homocysteic acid methotrexate analogues (EPA0142220);

These compounds are believed to act as antimetabolites of folic acid.

D. Podophyllotoxins

In another aspect, the therapeutic agent is a Podophyllotoxin, or a derivative or an analog thereof. Exemplary compounds of this type are Etoposide or Teniposide, which have the following structures:

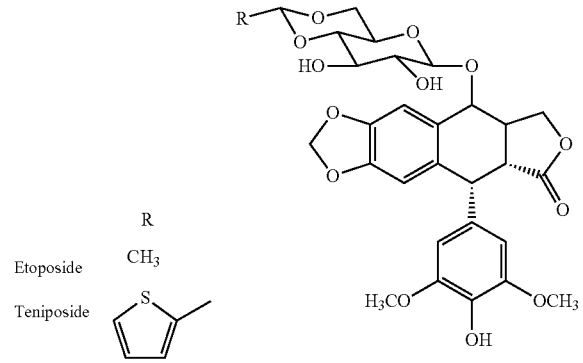

Other representative examples of podophyllotoxins include Cu(II)-VP-16 (etoposide) complex (Tawa et al., *Bioorg. Med. Chem.* 6(7):1003-1008, 1998), pyrrolecarboxamidino-bearing etoposide analogues (Ji et al., *Bioorg. Med. Chem. Lett.* 7(5):607-612, 1997), 4β-amino etoposide analogues (Hu, University of North Carolina Dissertation, 1992), γ-lactone ring-modified arylamino etoposide analogues (Zhou et al., *J. Med. Chem.* 37(2):287-92, 1994), N-glucosyl etoposide analogue (Allevi et al., *Tetrahedron Lett.* 34(45): 7313-16, 1993), etoposide A-ring analogues (Kadow et al., *Bioorg. Med. Chem. Lett.* 2(1):17-22, 1992), 4'-deshydroxy-4'-methyl etoposide (Saulnier et al., *Bioorg. Med. Chem. Lett.* 2(10):1213-18, 1992), pendulum ring etoposide analogues (Sinha et al., *Eur. J. Cancer* 26(5):590-3, 1990) and E-ring desoxy etoposide analogues (Saulnier et al., *J. Med. Chem.* 32(7):1418-20, 1989).

These compounds are believed to act as Topoisomerase II Inhibitors and/or DNA cleaving agents.

E. Camptothecins

In another aspect, the therapeutic agent is Camptothecin, or an analog or derivative thereof. Camptothecins have the following general structure.

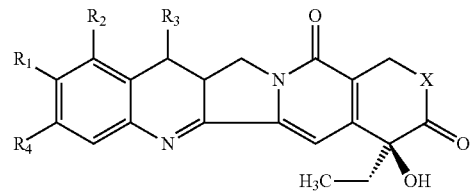

In this structure, X is typically O, but can be other groups, e.g., NH in the case of 21-lactam derivatives. $R_1$ is typically H or OH, but may be other groups, e.g., a terminally hydroxylated $C_{1-3}$ alkane. $R_2$ is typically H or an amino containing group such as $(CH_3)_2NHCH_2$, but may be other groups e.g., $NO_2$, $NH_2$, halogen (as disclosed in, e.g., U.S. Pat. No. 5,552, 156) or a short alkane containing these groups. $R_3$ is typically H or a short alkyl such as $C_2H_5$. $R_4$ is typically H but may be other groups, e.g., a methylenedioxy group with $R_1$.

Exemplary camptothecin compounds include topotecan, irinotecan (CPT-11), 9-aminocamptothecin, 21-lactam-20 (S)-camptothecin, 10,11-methylenedioxycamptothecin, SN-38, 9-nitrocamptothecin, 10-hydroxycamptothecin. Exemplary compounds have the structures:

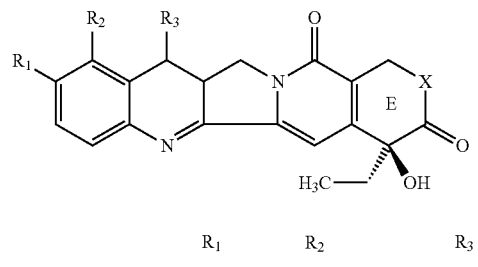

| | $R_1$ | $R_2$ | $R_3$ |
|---|---|---|---|
| Camptothecin: | H | H | H |
| Topotecan: | OH | $(CH_3)_2NHCH_2$ | H |
| SN-38: | OH | H | $C_2H_5$ |

X: O for most analogs, NH for 21-lactam analogs

Camptothecins have the five rings shown here. The ring labeled E must be intact (the lactone rather than carboxylate form) for maximum activity and minimum toxicity.

Camptothecins are believed to function as Topoisomerase I Inhibitors and/or DNA cleavage agents.

F. Hydroxyureas

The therapeutic agent of the present invention may be a hydroxyurea. Hydroxyureas have the following general structure:

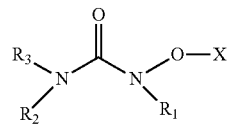

Suitable hydroxyureas are disclosed in, for example, U.S. Pat. No. 6,080,874, wherein $R_1$ is:

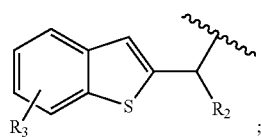

and $R_2$ is an alkyl group having 1-4 carbons and $R_3$ is one of H, acyl, methyl, ethyl, and mixtures thereof, such as a methylether.

Other suitable hydroxyureas are disclosed in, e.g., U.S. Pat. No. 5,665,768, wherein $R_1$ is a cycloalkenyl group, for example N-[3-[5-(4-fluorophenylthio)-furyl]-2-cyclopenten-1-yl]N-hydroxyurea; $R_2$ is H or an alkyl group having 1 to 4 carbons and $R_3$ is H; X is H or a cation.

Other suitable hydroxyureas are disclosed in, e.g., U.S. Pat. No. 4,299,778, wherein $R_1$ is a phenyl group substituted with one or more fluorine atoms; $R_2$ is a cyclopropyl group; and $R_3$ and X is H.

Other suitable hydroxyureas are disclosed in, e.g., U.S. Pat. No. 5,066,658, wherein $R_2$ and $R_3$ together with the adjacent nitrogen form:

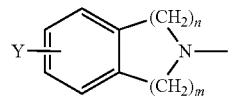

wherein m is 1 or 2, n is 0-2 and Y is an alkyl group.

In one aspect, the hydroxyurea has the structure:

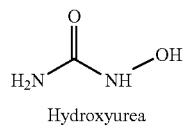

Hydroxyurea

These compounds are thought to function by inhibiting DNA synthesis.

G. Platinum Complexes

In another aspect, the therapeutic agent is a platinum compound. In general, suitable platinum complexes may be of Pt(II) or Pt(IV) and have this basic structure:

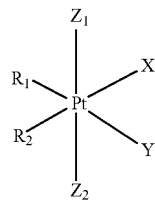

wherein X and Y are anionic leaving groups such as sulfate, phosphate, carboxylate, and halogen; $R_1$ and $R_2$ are alkyl, amine, amino alkyl any may be further substituted, and are basically inert or bridging groups. For Pt(II) complexes $Z_1$ and $Z_2$ are non-existent. For Pt(IV) $Z_1$ and $Z_2$ may be anionic groups such as halogen, hydroxy, carboxylate, ester, sulfate or phosphate. See, e.g., U.S. Pat. Nos. 4,588,831 and 4,250,189.

Suitable platinum complexes may contain multiple Pt atoms. See, e.g., U.S. Pat. Nos. 5,409,915 and 5,380,897. For example bisplatinum and triplatinum complexes of the type:

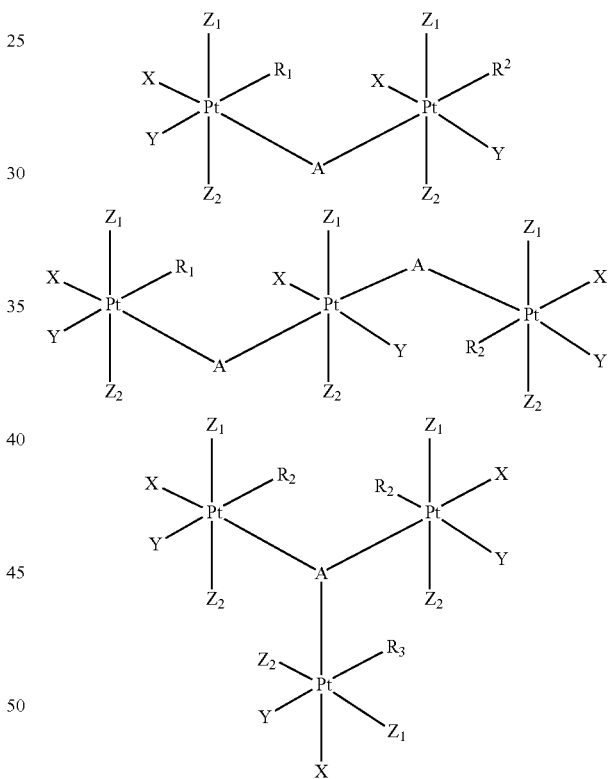

Exemplary platinum compounds are Cisplatin, Carboplatin, Oxaliplatin, and Miboplatin having the structures:

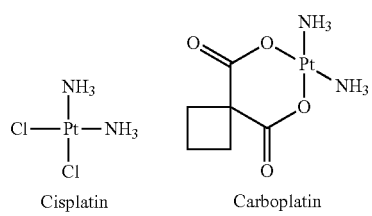

Cisplatin          Carboplatin

-continued

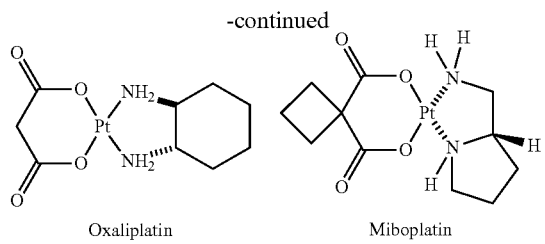

Oxaliplatin    Miboplatin

Other representative platinum compounds include (CPA)$_2$ Pt[DOLYM] and (DACH)Pt[DOLYM] cisplatin (Choi et al., *Arch. Pharmacal Res.* 22(2):151-156, 1999), Cis-[PtCl$_2$(4,7-H-5-methyl-7-oxo]1,2,4-[triazolo[1,5-a]pyrimidine)$_2$] (Navarro et al., *J. Med. Chem.* 41(3):332-338, 1998), [Pt(cis-1,4-DACH)(trans-Cl$_2$)(CBDCA)].½MeOH cisplatin (Shamsuddin et al., *Inorg. Chem.* 36(25):5969-5971, 1997), 4-pyridoxate diammine hydroxy platinum (Tokunaga et al., *Pharm. Sci.* 3(7):353-356, 1997), Pt(II) . . . Pt(II) (Pt$_2$[NHCHN(C(CH$_2$)(CH$_3$))]$_4$) (Navarro et al., *Inorg. Chem.* 35(26):7829-7835, 1996), 254-S cisplatin analogue (Koga et al., *Neurol. Res.* 18(3):244-247, 1996), o-phenylenediamine ligand bearing cisplatin analogues (Koeckerbauer & Bednarski, *J. Inorg. Biochem.* 62(4):281-298, 1996), trans, cis-[Pt(OAc)$_2$I$_2$(en)] (Kratochwil et al., *J. Med. Chem.* 39(13):2499-2507, 1996), estrogenic 1,2-diarylethylenediamine ligand (with sulfur-containing amino acids and glutathione) bearing cisplatin analogues (Bednarski, *J. Inorg. Biochem.* 62(1):75, 1996), cis-1,4-diaminocyclohexane cisplatin analogues (Shamsuddin et al., *J. Inorg. Biochem.* 61(4):291-301, 1996), 5' orientational isomer of cis-[Pt(NH$_3$)(4-aminoTEMP-O){d(GpG)}] (Dunham & Lippard, *J. Am. Chem. Soc.* 117(43): 10702-12, 1995), chelating diamine-bearing cisplatin analogues (Koeckerbauer & Bednarski, *J. Pharm. Sci.* 84(7): 819-23, 1995), 1,2-diarylethyleneamine ligand-bearing cisplatin analogues (Otto et al., *J. Cancer Res. Clin. Oncol.* 121(1):31-8, 1995), (ethylenediamine)platinum(II) complexes (Pasini et al., *J. Chem. Soc., Dalton Trans.* 4:579-85, 1995), CI-973 cisplatin analogue (Yang et al., *Int. J. Oncol.* 5(3):597-602, 1994), cis-diaminedichloroplatinum(II) and its analogues cis-1,1-cyclobutanedicarbosylato(2R)-2-methyl-1,4-butanediamineplatinum(II) and cis-diammine(glycolato) platinum (Claycamp & Zimbrick, *J. Inorg. Biochem.* 26(4): 257-67, 1986; Fan et al., *Cancer Res.* 48(11):3135-9, 1988; Heiger-Bernays et al., *Biochemistry* 29(36):8461-6, 1990; Kikkawa et al., *J. Exp. Clin. Cancer Res.* 12(4):233-40, 1993; Murray et al., *Biochemistry* 31(47):11812-17, 1992; Takahashi et al., *Cancer Chemother. Pharmacol.* 33(1):31-5, 1993), cis-amine-cyclohexylamine-dichloroplatinum(II) (Yoshida et al., *Biochem. Pharmacol.* 48(4):793-9, 1994), gem-diphosphonate cisplatin analogues (FR 2683529), (meso-1,2-bis(2,6-dichloro-4-hydroxyplenyl)ethylenediamine) dichloroplatinum(II) (Bednarski et al., *J. Med. Chem.* 35(23):4479-85, 1992), cisplatin analogues containing a tethered dansyl group (Hartwig et al., *J. Am. Chem. Soc.* 114(21): 8292-3, 1992), platinum(II) polyamines (Siegmann et al., *Inorg. Met.-Containing Polym. Mater.*, (*Proc. Am. Chem. Soc. Int. Symp.*), 335-61, 1990), cis-(3H)dichloro(ethylenediamine)platinum(II) (Eastman, *Anal. Biochem.* 197(2):311-15, 1991), trans-diamminedichloroplatinum(II) and cis-(Pt (NH$_3$)$_2$(N$_3$-cytosine)Cl) (Bellon & Lippard, *Biophys. Chem.* 35(2-3):179-88, 1990), 3H-cis-1,2-diaminocyclohexanedichloroplatinum(II) and 3H-cis-1,2-diaminocyclohexane-malonatoplatinum (II) (Oswald et al., *Res. Commun. Chem. Pathol. Pharmacol.* 64(1):41-58, 1989), diaminocarboxylatoplatinum (EPA 296321), trans-(D,1)-1,2-diaminocyclohexane carrier ligand-bearing platinum analogues (Wyrick & Chaney, *J. Labelled Compd. Radiopharm.* 25(4): 349-57, 1988), aminoalkylaminoanthraquinone-derived cisplatin analogues (Kitov et al., *Eur. J. Med. Chem.* 23(4):381-3, 1988), spiroplatin, carboplatin, iproplatin and JM40 platinum analogues (Schroyen et al., *Eur. J. Cancer Clin. Oncol.* 24(8):1309-12, 1988), bidentate tertiary diamine-containing cisplatinum derivatives (Orbell et al., *Inorg. Chim. Acta* 152(2):125-34, 1988), platinum(II), platinum(IV) (Liu & Wang, *Shandong Yike Daxue Xuebao* 24(1):35-41, 1986), cis-diammine(1,1-cyclobutanedicarboxylato-)platinum(II) (carboplatin, JM8) and ethylenediamine-malonatoplatinum(II) (JM40) (Begg et al., *Radiother. Oncol.* 9(2):157-65, 1987), JM8 and JM9 cisplatin analogues (Harstrick et al., *Int. J. Androl.* 10(1); 139-45, 1987), (NPr4)2((PtCL4).cis-(PtCl2-(NH2Me)2)) (Brammer et al., *J. Chem. Soc., Chem. Commun.* 6:443-5, 1987), aliphatic tricarboxylic acid platinum complexes (EPA 185225), and cis-dichloro(amino acid) (tert-butylamine)platinum(II) complexes (Pasini & Bersanetti, *Inorg. Chim. Acta* 107(4):259-67, 1985). These compounds are thought to function by binding to DNA, i.e., acting as alkylating agents of DNA.

II. Compositions and Formulations

As noted above, therapeutic agents described herein may be formulated in a variety of manners, and thus may additionally comprise a carrier. In this regard, a wide variety of carriers may be selected of either polymeric or non-polymeric origin. The polymers and non-polymer based carriers and formulations which are discussed in more detail below are provided merely by way of example, not by way of limitation.

Within one embodiment of the invention a wide variety of polymers can be utilized to contain and/or deliver one or more of the agents discussed above, including for example both biodegradable and non-biodegradable compositions. Representative examples of biodegradable compositions include albumin, collagen, gelatin, chitosan, hyaluronic acid, starch, cellulose and derivatives thereof (e.g., methylcellulose, hydroxypropylcellulose, hydroxypropylmethylcellulose, carboxymethylcellulose, cellulose acetate phthalate, cellulose acetate succinate, hydroxypropylmethylcellulose phthalate), alginates, casein, dextrans, polysaccharides, fibrinogen, poly(L-lactide), poly(D,L lactide), poly(L-lactide-co-glycolide), poly(D,L-lactide-co-glycolide), poly(glycolide), poly(trimethylene carbonate), poly(hydroxyvalerate), poly (hydroxybutyrate), poly(caprolactone), poly(alkylcarbonate) and poly(orthoesters), polyesters, poly(hydroxyvaleric acid), polydioxanone, poly(malic acid), poly(tartronic acid), polyanhydrides, polyphosphazenes, poly(amino acids), copolymers of such polymers and blends of such polymers (see generally, Illum, L., Davids, S. S. (eds.) "Polymers in Controlled Drug Delivery" Wright, Bristol, 1987; Arshady, *J. Controlled Release* 17:1-22, 1991; Pitt, *Int. J. Phar.* 59:173-196, 1990; Holland et al., *J. Controlled Release* 4:155-0180, 1986). Representative examples of nondegradable polymers include poly(ethylene-co-vinyl acetate) ("EVA") copolymers, silicone rubber, acrylic polymers (e.g., polyacrylic acid, polymethylacrylic acid, poly(hydroxyethylmethacrylate), polymethylmethacrylate, polyalkylcyanoacrylate), polyethylene, polyproplene, polyamides (e.g., nylon 6,6), polyurethane (e.g., poly(ester urethanes), poly(ether urethanes), poly(ester-urea), poly(carbonate urethanes)), polyethers (e.g., poly(ethylene oxide), poly(propylene oxide), Pluronics and poly(tetramethylene glycol)) and vinyl polymers [e.g., polyvinylpyrrolidone, poly(vinyl alcohol), poly (vinyl acetate phthalate)]. Polymers may also be developed which are either anionic (e.g., alginate, carrageenin, carboxymethyl cellulose and poly(acrylic acid), or cationic (e.g., chitosan, poly-L-lysine, polyethylenimine, and poly (allyl amine)) (see generally, Dunn et al., *J. Applied Polymer Sci.* 50:353-365, 1993; Cascone et al., *J. Materials Sci.: Materials in Medicine* 5:770-774, 1994; Shiraishi et al., *Biol. Pharm. Bull.* 16(11):1164-1168, 1993; Thacharodi and Rao, *Int'l J. Pharm.* 120:115-118, 1995; Miyazaki et al., *Int'l J. Pharm.* 118:257-263, 1995). Particularly preferred polymeric carriers include poly(ethylene-co-vinyl acetate), polyurethane, acid, poly(caprolactone), poly(valerolactone), polyanhydrides, copolymers of poly(caprolactone) or poly(lactic acid) with a polyethylene glycol (e.g., MePEG), and blends thereof.

Other representative polymers include carboxylic polymers, polyacetates, polyacrylamides, polycarbonates, polyethers, polyesters, polyethylenes, polyvinylbutyrals, polysilanes, polyureas, polyurethanes, polyoxides, polystyrenes, polysulfides, polysulfones, polysulfonides, polyvinylhalides, pyrrolidones, rubbers, thermal-setting polymers, cross-linkable acrylic and methacrylic polymers, ethylene acrylic acid copolymers, styrene acrylic copolymers, vinyl acetate polymers and copolymers, vinyl acetal polymers and copolymers, epoxy, melamine, other amino resins, phenolic polymers, and copolymers thereof, water-insoluble cellulose ester polymers (including cellulose acetate propionate, cellulose acetate, cellulose acetate butyrate, cellulose nitrate, cellulose acetate phthalate, and mixtures thereof), polyvinylpyrrolidone, polyethylene glycols, polyethylene oxide, polyvinyl alcohol, polyethers, polysaccharides, hydrophilic polyurethane, polyhydroxyacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof; cellulose esters and ethers, ethyl cellulose, hydroxyethyl cellulose, cellulose nitrate, cellulose acetate, cellulose acetate butyrate, cellulose acetate propionate, polyurethane, polyacrylate, natural and synthetic elastomers, rubber, acetal, nylon, polyester, styrene polybutadiene, acrylic resin, polyvinylidene chloride, polycarbonate, homopolymers and copolymers of vinyl compounds, polyvinylchloride, polyvinylchloride acetate.

Representative examples of patents relating to polymers and their preparation include PCT Publication Nos. WO72827, 98/12243, 98/19713, 98/41154, 99/07417, 00/33764, 00/21842, 00/09190, 00/09088, 00/09087, 2001/17575 and 2001/15526 (as well as their corresponding U.S. applications), and U.S. Pat. Nos. 4,500,676, 4,582,865, 4,629,623, 4,636,524, 4,713,448, 4,795,741, 4,913,743, 5,069,899, 5,099,013, 5,128,326, 5,143,724, 5,153,174, 5,246,698, 5,266,563, 5,399,351, 5,525,348, 5,800,412, 5,837,226, 5,942,555, 5,997,517, 6,007,833, 6,071,447, 6,090,995, 6,099,563, 6,106,473, 6,110,483, 6,121,027, 6,156,345, 6,179,817, 6,197,051, 6,214,901, 6,335,029, 6,344,035, which, as noted above, are all incorporated by reference in their entirety.

Polymers can be fashioned in a variety of forms, with desired release characteristics and/or with specific desired properties. For example, polymers can be fashioned to release a therapeutic agent upon exposure to a specific triggering event such as pH (see, e.g., Heller et al., "Chemically Self-Regulated Drug Delivery Systems," in *Polymers in Medicine III*, Elsevier Science Publishers B.V., Amsterdam, 1988, pp. 175-188; Kang et al., *J. Applied Polymer Sci.* 48:343-354, 1993; Dong et al., *J. Controlled Release* 19:171-178, 1992; Dong and Hoffman, *J. Controlled Release* 15:141-152, 1991; Kim et al., *J. Controlled Release* 28:143-152, 1994; Cornejo-Bravo et al., *J. Controlled Release* 33:223-229, 1995; Wu and Lee, *Pharm. Res.* 10(10):1544-1547, 1993; Serres et al., *Pharm. Res.* 13(2):196-201, 1996; Peppas, "Fundamentals of pH- and Temperature-Sensitive Delivery Systems," in Gurny et al. (eds.), *Pulsatile Drug Delivery*, Wissenschaftliche Verlagsgesellschaft mbH, Stuttgart, 1993, pp. 41-55; Doelker, "Cellulose Derivatives," 1993, in Peppas and Langer (eds.), *Biopolymers I*, Springer-Verlag, Berlin). Representative examples of pH-sensitive polymers include poly(acrylic acid)-based polymers and derivatives (including, for example, homopolymers such as poly(aminocarboxylic acid), poly(acrylic acid), poly(methyl acrylic acid), copolymers of such homopolymers, and copolymers of poly(acrylic acid) and acrylmonomers such as those discussed above). Other pH sensitive polymers include polysaccharides such as carboxymethyl cellulose, hydroxypropylmethylcellulose phthalate, hydroxypropyl-methylcellulose acetate succinate, cellulose acetate trimellilate, chitosan and alginates. Yet other pH sensitive polymers include any mixture of a pH sensitive polymer and a water soluble polymer.

Likewise, polymers can be fashioned which are temperature sensitive (see, e.g., Chen et al., "Novel Hydrogels of a Temperature-Sensitive Pluronic Grafted to a Bioadhesive Polyacrylic Acid Backbone for Vaginal Drug Delivery," in *Proceed. Intern. Symp. Control. Rel. Bioact. Mater.* 22:167-168, Controlled Release Society, Inc., 1995; Okano, "Molecular Design of Stimuli-Responsive Hydrogels for Temporal Controlled Drug Delivery," in *Proceed. Intern. Symp. Control. Rel. Bioact. Mater.* 22:111-112, Controlled Release Society, Inc., 1995; Johnston et al., *Pharm. Res.* 9(3):425-433, 1992; Tung, *Int'l J. Pharm.* 107:85-90, 1994; Harsh and Gehrke, *J. Controlled Release* 17:175-186, 1991; Bae et al., *Pharm. Res.* 8(4):531-537, 1991; Dinarvand and D'Emanuele, *J. Controlled Release* 36:221-227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820-821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822-823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829-830; Kim et al., *Pharm. Res.* 9(3):283-290, 1992; Bae et al., *Pharm. Res.* 8(5):624-628, 1991; Kono et al., *J. Controlled Release* 30:69-75, 1994; Yoshida et al., *J. Controlled Release* 32:97-102, 1994; Okano et al., *J. Controlled Release* 36:125-133, 1995; Chun and Kim, *J. Controlled Release* 38:39-47, 1996; D'Emanuele and Dinarvand, *Int'l J. Pharm.* 118:237-242, 1995; Katono et al., *J. Controlled Release* 16:215-228, 1991; Hoffman, "Thermally Reversible Hydrogels Containing Biologically Active Species," in Migliaresi et al. (eds.), *Polymers in Medicine III*, Elsevier Science Publishers B.V., Amsterdam, 1988, pp. 161-167; Hoffman, "Applications of Thermally Reversible Polymers and Hydrogels in Therapeutics and Diagnostics," in *Third International Symposium on Recent Advances in Drug Delivery Systems*, Salt Lake City, Utah, Feb. 24-27, 1987, pp. 297-305; Gutowska et al., *J.*

*Controlled Release* 22:95-104, 1992; Palasis and Gehrke, *J. Controlled Release* 18:1-12, 1992; Paavola et al., *Pharm. Res.* 12(12):1997-2002, 1995).

Representative examples of thermogelling polymers include homopolymers such as poly(N-methyl-N-n-propylacrylamide), poly(N-n-propylacrylamide), poly(N-methyl-N-isopropylacrylamide), poly(N-n-propylmethacrylamide), poly(N-isopropylacrylamide), poly(N, n-diethylacrylamide), poly(N-isopropylmethacrylamide), poly(N-cyclopropylacrylamide), poly(N-ethylmethyacrylamide), poly(N-methyl-N-ethylacrylamide), poly(N-cyclopropylmethacrylamide) and poly(N-ethylacrylamide). Moreover thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide).

Other representative examples of thermogelling cellulose ether derivatives such as hydroxypropyl cellulose, methyl cellulose, hydroxypropylmethyl cellulose, ethylhydroxyethyl cellulose, and Pluronics, such as F-127.

A wide variety of forms may be fashioned by the polymers of the present invention, including for example, rod-shaped devices, pellets, slabs, particulates, micelles, films, molds, sutures, threads, gels, creams, ointments, sprays or capsules (see, e.g., Goodell et al., *Am. J. Hosp. Pharm.* 43:1454-1461, 1986; Langer et al., "Controlled release of macromolecules from polymers", in *Biomedical Polymers, Polymeric Materials and Pharmaceuticals for Biomedical Use*, Goldberg, E. P., Nakagim, A. (eds.) Academic Press, pp. 113-137, 1980; Rhine et al., *J. Pharm. Sci.* 69:265-270, 1980; Brown et al., *J. Pharm. Sci.* 72:1181-1185, 1983; and Bawa et al., *J. Controlled Release* 1:259-267, 1985). Agents may be incorporated by dissolution in the polymer, occlusion in the matrices of the polymer, bound by covalent linkages, or encapsulated in microcapsules. Within certain preferred embodiments of the invention, therapeutic compositions are provided in non-capsular formulations, such as coatings microspheres (ranging from nanometers to micrometers in size), pastes, threads or sutures of various size, films and sprays.

Other compounds which can be utilized to carry and/or deliver the agents provided herein include vitamin-based compositions (e.g., based on vitamins A, D, E and/or K, see, e.g., PCT publication Nos. WO 98/30205 and WO 00/71163) and liposomes (see, U.S. Pat. Nos. 5,534,499, 5,683,715, 5,776,485, 5,882,679, 6,143,321, 6,146,659, 6,200,598, and PCT Publication Nos. WO 98/34597, WO 99/65466, WO 00/01366, WO 00/53231, WO 99/35162, WO 00/117508, WO 00/125223, WO 00/149,268, WO 00/1565438, and WO 00/158455).

Preferably, therapeutic compositions of the present invention are fashioned in a manner appropriate to the intended use. Within certain aspects of the present invention, the therapeutic composition should be biocompatible, and release one or more agents over a period of several days to months. Further, therapeutic compositions of the present invention should preferably be stable for several months and capable of being produced, and maintained under sterile conditions.

Within certain aspects of the present invention, therapeutic compositions may be fashioned in any size ranging from 50 nm to 500 μm, depending upon the particular use. Alternatively, such compositions may also be readily applied as a "spray" which solidifies into a film or coating. Such sprays may be prepared from microspheres of a wide array of sizes, including for example, from 0.1 μm to 9 μm, from 10 μm to 30 μm and from 30 μm to 100 μm.

Therapeutic compositions of the present invention may also be prepared in a variety of "paste" or gel forms. For example, within one embodiment of the invention, therapeutic compositions are provided which are liquid at one temperature (e.g., temperature greater than 37° C.) and solid or semi-solid at another temperature (e.g., ambient body temperature, or any temperature lower than 37° C.). Also included are polymers, such as Pluronic F-127, which are liquid at a low temperature (e.g., 4° C.) and a gel at body temperature. Such "thermopastes" may be readily made given the disclosure provided herein.

Within yet other aspects of the invention, the therapeutic compositions of the present invention may be formed as a film. Preferably, such films are generally less than 5, 4, 3, 2 or 1 mm thick, more preferably less than 0.75 mm or 0.5 mm thick, and most preferably less than 500 μm. Such films are preferably flexible with a good tensile strength (e.g., greater than 50, preferably greater than 100, and more preferably greater than 150 or 200 N/cm$^2$), good adhesive properties (i.e., readily adheres to moist or wet surfaces), and have controlled permeability.

Within certain embodiments of the invention, the therapeutic compositions can also comprise additional ingredients such as surfactants (e.g., Pluronics such as F-127, L-122, L-92, L-81, and L-61).

Within further aspects of the present invention, polymers are provided which are adapted to contain and release a hydrophobic compound, the carrier containing the hydrophobic compound in combination with a carbohydrate, protein or polypeptide. Within certain embodiments, the polymeric carrier contains or comprises regions, pockets or granules of one or more hydrophobic compounds. For example, within one embodiment of the invention, hydrophobic compounds may be incorporated within a matrix which contains the hydrophobic compound, followed by incorporation of the matrix within the polymeric carrier. A variety of matrices can be utilized in this regard, including for example, carbohydrates and polysaccharides, such as starch, cellulose, dextran, methylcellulose, and hyaluronic acid, proteins or polypeptides such as albumin, collagen and gelatin. Within alternative embodiments, hydrophobic compounds may be contained within a hydrophobic core, and this core contained within a hydrophilic shell.

Other carriers that may likewise be utilized to contain and deliver the agents described herein include: hydroxypropyl β-cyclodextrin (Cserhati and Hollo, *Int J. Pharm.* 108:69-75, 1994), liposomes (see, e.g., Sharma et al., *Cancer Res.* 53:5877-5881, 1993; Sharma and Straubinger, *Pharm. Res.* 11(60):889-896, 1994; WO 93/18751; U.S. Pat. No. 5,242,073), liposome/gel (WO 94/26254), nanocapsules (Bartoli et al., *J. Microencapsulation* 7(2):191-197, 1990), micelles (Alkan-Onyuksel et al., *Pharm. Res.* 11(2):206-212, 1994), implants (Jampel et al., *Invest. Ophthalm. Vis. Science* 34(11): 3076-3083, 1993; Walter et al., *Cancer Res.* 54:22017-2212, 1994), nanoparticles (Violante and Lanzafame PAACR), nanoparticles—modified (U.S. Pat. No. 5,145,684), nanoparticles (surface modified) (U.S. Pat. No. 5,399,363), taxol emulsion/solution (U.S. Pat. No. 5,407,683), micelle (surfactant) (U.S. Pat. No. 5,403,858), synthetic phospholipid compounds (U.S. Pat. No. 4,534,899), gas borne dispersion (U.S. Pat. No. 5,301,664), foam, spray, gel, lotion, cream, ointment, dispersed vesicles, particles or droplets solid- or liquid-aerosols, microemulsions (U.S. Pat. No. 5,330,756), polymeric shell (nano- and micro-capsule) (U.S. Pat. No. 5,439,686), taxoid-based compositions in a surface-active agent (U.S. Pat. No. 5,438,072), liquid emulsions (Tarr et al., *Pharm Res.* 4:62-165, 1987), nanospheres (Hagan et al., *Proc. Intern. Symp. Control Rel. Bioact. Mater.* 22, 1995; Kwon et al., *Pharm Res.* 12(2):192-195; Kwon et al., *Pharm Res.* 10(7):970-974; Yokoyama et al., *J. Contr. Rel.* 32:269-277, 1994; Gref et al., *Science* 263:1600-1603, 1994; Bazile et al., *J. Pharm. Sci.* 84:493-498, 1994) and implants (U.S. Pat. No. 4,882,168).

The agents provided herein can also be formulated as a sterile composition (e.g., by treating the composition with ethylene oxide or by irradiation), packaged with preservatives or other suitable excipients suitable for administration to humans. Similarly, the devices provided herein (e.g., coated catheter) may be sterilized and prepared suitable for implantation into humans.

III. Medical Implants

A. Representative Medical Implants

A wide variety of implants or devices can be coated with or otherwise constructed to contain and/or release the therapeutic agents provided herein. Representative examples include cardiovascular devices (e.g., implantable venous catheters, venous ports, tunneled venous catheters, chronic infusion lines or ports, including hepatic artery infusion catheters, pacemakers and pacemaker leads (see, e.g., U.S. Pat. Nos. 4,662,382, 4,782,836, 4,856,521, 4,860,751, 5,101,824, 5,261,419, 5,284,491, 6,055,454, 6,370,434, and 6,370,434), implantable defibrillators (see, e.g., U.S. Pat. Nos. 3,614,954, 3,614,955, 4,375,817, 5,314,430, 5,405,363, 5,607,385, 5,697,953, 5,776,165, 6,067,471, 6,169,923, and 6,152,955)); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, portosystemic shunts, shunts for ascites, peritoneal implants for drug delivery, peritoneal dialysis catheters, and suspensions or solid implants to prevent surgical adhesions); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy, central venous catheters (see, e.g., U.S. Pat. Nos. 3,995,623, 4,072,146 4,096,860, 4,099,528, 4,134,402, 4,180,068, 4,385,631, 4,406,656, 4,568,329, 4,960,409, 5,176,661, 5,916,208), urinary catheters (see, e.g. U.S. Pat. Nos. 2,819,718, 4,227,533, 4,284,459, 4,335,723, 4,701,162, 4,571,241, 4,710,169, and 5,300,022,)); prosthetic heart valves (see, e.g., U.S. Pat. Nos. 3,656,185, 4,106, 129, 4,892,540, 5,528,023, 5,772,694, 6,096,075, 6,176,877, 6,358,278, and 6,371,983), vascular grafts (see, e.g. 3,096, 560, 3,805,301, 3,945,052, 4,140,126, 4,323,525, 4,355,426, 4,475,972, 4,530,113, 4,550,447, 4,562,596, 4,601,718, 4,647,416, 4,878,908, 5,024,671, 5,104,399, 5,116,360, 5,151,105, 5,197,977, 5,282,824, 5,405,379, 5,609,624, 5,693,088, and 5,910,168), opthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to transtempanic drains); plastic surgery implants (e.g., breast implants or chin implants), catheter cuffs and orthopedic implants (e.g., cemented orthopedic prostheses).

B. Methods of Making Medical Implants Having Therapeutic Agents

Implants and other surgical or medical devices may be covered, coated, contacted, combined, loaded, filled, associated with, or otherwise adapted to release therapeutic agents compositions of the present invention in a variety of manners, including for example: (a) by directly affixing to the implant or device a therapeutic agent or composition (e.g., by either spraying the implant or device with a polymer/drug film, or by dipping the implant or device into a polymer/drug solution, or by other covalent or noncovalent means); (b) by coating the implant or device with a substance, such as a hydrogel, which will in turn absorb the therapeutic composition (or therapeutic factor above); (c) by interweaving therapeutic composition coated thread (or the polymer itself formed into a thread) into the implant or device; (d) by inserting the implant or device into a sleeve or mesh which is comprised of or coated with a therapeutic composition; (e) constructing the implant or device itself with a therapeutic agent or composition; or (f) by otherwise adapting the implant or device to release the therapeutic agent. Within preferred embodiments of the invention, the composition should firmly adhere to the implant or device during storage and at the time of insertion. The therapeutic agent or composition should also preferably not degrade during storage, prior to insertion, or when warmed to body temperature after insertion inside the body (if this is required). In addition, it should preferably coat or cover the desired areas of the implant or device smoothly and evenly, with a uniform distribution of therapeutic agent. Within preferred embodiments of the invention, the therapeutic agent or composition should provide a uniform, predictable, prolonged release of the therapeutic factor into the tissue surrounding the implant or device once it has been deployed. For vascular stents, in addition to the above properties, the composition should not render the stent thrombogenic (causing blood clots to form), or cause significant turbulence in blood flow (more than the stent itself would be expected to cause if it was uncoated).

Within certain embodiments of the invention, a therapeutic agent can be deposited directly onto all or a portion of the device (see, e.g., U.S. Pat. Nos. 6,096,070 and 6,299,604), or admixed with a delivery system or carrier (e.g., a polymer, liposome, or vitamin as discussed above) which is applied to all or a portion of the device (see the patents, patent applications, and references listed above under "Compositions and Formulations."

Within certain aspects of the invention, therapeutic agents can be attached to a medical implant using non-covalent attachments. For example, for compounds that are relatively sparingly water soluble or water insoluble, the compound can be dissolved in an organic solvent a specified concentration. The solvent chosen for this application would not result in dissolution or swelling of the polymeric device surface. The medical implant can then be dipped into the solution, withdrawn and then dried (air dry and/or vacuum dry). Alternatively, this drug solution can be sprayed onto the surface of the implant. This can be accomplished using current spray coating technology. The release duration for this method of coating would be relatively short and would be a function of the solubility of the drug in the body fluid in which it was placed.

In another aspect, a therapeutic agent can be dissolved in a solvent that has the ability to swell or partially dissolve the surface of a polymeric implant. Depending on the solvent/implant polymer combination, the implant could be dipped into the drug solution for a period of time such that the drug can diffuse into the surface layer of the polymeric device. Alternatively the drug solution can be sprayed onto all or a part of the surface of the implant. The release profile of the drug depends upon the solubility of the drug in the surface polymeric layer. Using this approach, one would ensure that the solvent does not result in a significant distortion or dimensional change of the medical implant.

If the implant is composed of materials that do not allow incorporation of a therapeutic agent into the surface layer using the above solvent method, one can treat the surface of the device with a plasma polymerization method such that a thin polymeric layer is deposited onto the device surface. Examples of such methods include parylene coating of devices, and the use of various monomers such hydrocyclosiloxane monomers, acrylic acid, acrylate monomers, methacrylic acid or methacrylate monomers. One can then use the dip coating or spray coating methods described above to incorporate the therapeutic agent into the coated surface of the implant.

For therapeutic agents that have some degree of water solubility, the retention of these compounds on a device are relatively short-term. For therapeutic agents that contain ionic groups, it is possible to ionically complex these agents to oppositely charged compounds that have a hydrophobic component. For example therapeutic agents containing amine groups can be complexed with compounds such as sodium dodecyl sulfate (SDS). Compounds containing carboxylic groups can be complexed with tridodecymethyammonium chloride (TDMAC). Mitoxantrone, for example, has two secondary amine groups and comes as a chloride salt. This compound can be added to sodium dodecyl sulfate in order to form a complex. This complex can be dissolved in an organic solvent which can then be dip coated or spray coated. Doxorubicin has an amine group and could thus also be complexed with SDS. This complex could then be applied to the device by dip coating or spray coating methods. Methotrexate, for example contains 2 carboxylic acid groups and could thus be complexed with TDMAC and then coated onto the medical implant.

For therapeutic agents that have the ability to form ionic complexes or hydrogen bonds, the release of these agents from the device can be modified by the use of organic compounds that have the ability to form ionic or hydrogen bonds with the therapeutic agent. As described above, a complex between the ionically charged therapeutic agent and an oppositely charged hydrophobic compound can be prepared prior to application of this complex to the medical implant. In another embodiment, a compound that has the ability to form ionic or hydrogen bond interactions with the therapeutic agent can be incorporated into the implant during the manufacture process, or during the coating process. Alternatively, this compound can be incorporated into a coating polymer that is applied to the implant or during the process of loading the therapeutic agent into or onto the implant. These agents can include fatty acids (e.g., palmitic acid, stearic acid, lauric acid), aliphatic acids, aromatic acids (e.g., benzoic acid, salicylic acid), cylcoaliphatic acids, aliphatic (stearyl alcohol, lauryl alcohol, cetyl alcohol) and aromatic alcohols alco multifunctional alcohols (e.g., citric acid, tartaric acid, pentaerithratol), lipids (e.g., phosphatidyl choline, phosphatidylethanolamine), carbohydrates, sugars, spermine, spermidine, aliphatic and aromatic amines, natural and synthetic amino acids, peptides or proteins. For example, a fatty acid such as palmitic acid can be used to modulate the release of 5-Fluoruracil from the implant.

For therapeutic agents that have the ability to form ionic complexes or hydrogen bonds, the release of these agents from the implant can be modified by the use of polymers that have the ability to form ionic or hydrogen bonds with the therapeutic agent. For example, therapeutic agents containing amine groups can form ionic complexes with sulfonic or carboxylic pendant groups or end-groups of a polymer. Examples of polymers that can be used for this application include, but are not limited to polymers and copolymers that are prepared using acrylic acid, methacrylic acid, sodium styrene sulfonate, styrene sulfonic acid, maleic acid or 2-acrylamido-2-methyl propane sulfonic acid. Polymers that have been modified by sulfonation post-polymerization can also be used in this application. The medical implant, for example, can be coated with, or prepared with, a polymer that comprises nafion, a sulfonated fluoropolymer. This medical device can then be dipped into a solution that comprises the amine-containing therapeutic agent. The amine-containing therapeutic agent can also be applied by a spray coating process. Methotrexate and doxorubicin are examples of therapeutic agents that can be used in this application.

It is known that the presence of bacteria on the implant surface can result in a localized decrease in pH. For polymers that comprise ionic exchange groups, for example, carboxylic groups, these polymers can have a localized increase in release of the therapeutic agent in response to the localized decrease in pH as a result of the presence of the bacteria. For therapeutic agents that contain carboxylic acid groups, polymers with pendant end-groups comprising primary, secondary, tertiary or quaternary amines can be used to modulate the release of the therapeutic agent.

Therapeutic agents with available functional groups can be covalently attached to the medical implant surface using several chemical methods. If the polymeric material used to manufacture the implant has available surface functional groups then these can be used for covalent attachment of the agent. For example, if the implant surface contains carboxylic acid groups, these groups can be converted to activated carboxylic acid groups (e.g acid chlorides, succinimidyl derivatives, 4-nitrophenyl ester derivatives etc). These activated carboxylic acid groups can then be reacted with amine functional groups that are present on the therapeutic agent (e.g., methotrexate, mitoxantrone).

For surfaces that do not contain appropriate functional groups, these groups can be introduced to the polymer surface via a plasma treatment regime. For example, carboxylic acid groups can be introduced via a plasma treatment process process (e.g., the use of $O_2$ and/or $CO_2$ as a component in the feed gas mixture). The carboxylic acid groups can also be introduced using acrylic acid or methacrylic acid in the gas stream. These carboxylic acid groups can then be converted to activated carboxylic acid groups (e.g., acid chlorides, succinimidyl derivatives, 4-nitrophenyl ester derivatives, etc.) that can subsequently be reacted with amine functional groups that are present on the therapeutic agent.

In addition to direct covalent bonding to the implant surface, the therapeutic agents with available functional groups can be covalently attached to the medical implant via a linker. These linkers can be degradable or non-degradable. Linkers that are hydrolytically or enzymatically cleaved are preferred. These linkers can comprise azo, ester, amide, thioester, anhydride, or phosphoester bonds.

To further modulate the release of the therapeutic agent from the medical implant, portions of or the entire medical implant may be further coated with a polymer. The polymer coating can comprise the polymers described above. The polymer coating can be applied by a dip coating process, a spray coating process or a plasma deposition process. This coating can, if desired, be further crosslinked using thermal, chemical, or radiation (e.g., visible light, ultraviolet light, e-beam, gamma radiation, x-ray radiation) techniques in order to further modulate the release of the therapeutic agent from the medical implant.

This polymer coating can further contain agents that can increase the flexibility (e.g., plasticizer—glycerol, triethyl citrate), lubricity (e.g., hyaluronic acid), biocompatibility or hemocompatability (e.g., heparin) of the coating.

The methods above describe methods for incorporation of a therapeutic agent into or onto a medical implant. Additional antibacterial or antifungal agents can also be incorporated into or onto the medical implant. These antibacterial or antifungal agents can be incorporated into or onto the medical implant prior to, simultaneously or after the incorporation of the therapeutic agents, described above, into or onto the medical implant. Agents that can be used include, but are not limited to silver compounds (e.g., silver chloride, silver nitrate, silver oxide), silver ions, silver particles, iodine, povidone/iodine, chlorhexidine, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin, azaserine, candicidin(s), chlorphenesin, dermostatin(s), filipin, fungichromin, mepartricin, nystatin, oligomycin(s), ciproflaxacin, norfloxacin, ofloxacin, pefloxacin, enoxacin, rosoxacin, amifloxacin, fleroxacin, temafloaxcin, lomefloxacin, perimycin A or tubercidin, and the like.

IV. Clinical Applications

In order to further the understanding of the invention, discussed in more detail below are various clinical applications for the compositions, methods and devices provided herein.

Briefly, as noted above, within one aspect of the invention methods are provided for preventing, reducing, and/or inhibiting an infection associated with a medical device or implant, comprising the step of introducing into a patient a medical implant which releases a chemotherapeutic agent, wherein the chemotherapeutic agent reduces, inhibits, or prevents the growth or transmission of foreign organisms (e.g., bacteria, fungi, or viruses). As used herein, agents that reduce, inhibit, or prevent the growth or transmission of foreign organisms in a patient means that the growth or transmission of a foreign organism is reduced, inhibited, or prevented in a statistically significant manner in at least one clinical outcome, or by any measure routinely used by persons of ordinary skill in the art as a diagnostic criterion in determining the same. In a preferred embodiment, the medical implant has been covered or coated with an anthracycline (e.g., doxorubicin and mitoxantrone), fluoropyrimidine (e.g., 5-FU), folic acid antagonist (e.g., methotrexate), podophylotoxin (e.g., etoposide), camptothecin, hydroxyurea, and/or a platinum complex (e.g., cisplatin).

Particularly preferred agents which are utilized within the context of the present invention should have an MIC of less than or equal to any one of $10^{-4}$M, $10^{-5}$M, $10^{-6}$M, or, $10^{-7}$M. Furthermore, particularly preferred agents are suitable for use at concentrations less than that 10%, 5%, or even 1% of the concentration typically used in chemotherapeutic applications (Goodman and Gilman's The Pharmacological Basis of Therapeutics. Editors J. G. Hardman, L. L. Limbird. Consulting editor A. Goodman Gilman Tenth Edition. McGraw-Hill Medical publishing division. 10th edition, 2001, 2148 pp.). Finally, the devices should preferably be provided sterile, and suitable for use in humans.

A. Vascular Catheter-Associated Infections

More than 30 million patients receive infusion therapy annually in the United States. In fact, 30% of all hospitalized patients have at least one vascular catheter in place during their stay in hospital. A variety of medical devices are used for infusion therapy including, but not restricted to, peripheral intravenous catheters, central venous catheters, total parenteral nutrition catheters, peripherally inserted central venous catheters (PIC lines), totally implanted intravascular access devices, flow-directed balloon-tipped pulmonary artery catheters, arterial lines, and long-term central venous access catheters (Hickman lines, Broviac catheters).

Unfortunately, vascular access catheters are prone to infection by a variety of bacteria and are a common cause of bloodstream infection. Of the 100,000 bloodstream infections in US hospitals each year, many are related to the presence of an intravascular device. For example, 55,000 cases of bloodstream infections are caused by central venous catheters, while a significant percentage of the remaining cases are related to peripheral intravenous catheters and arterial lines.

Bacteremia related to the presence of intravascular devices is not a trivial clinical concern: 50% of all patients developing this type of infection will die as a result (over 23,000 deaths per year) and in those who survive, their hospitalization will be prolonged by an average of 24 days. Complications related to bloodstream infections include cellulites, the formation of abscesses, septic thrombophlebitis, and infective endocarditis. Therefore, there is a tremendous clinical need to reduce the morbidity and mortality associated with intravascular catheter infections.

The most common point of entry for the infection-causing bacteria is tracking along the device from the insertion site in the skin. Skin flora spread along the outside of the device to ultimately gain access to the bloodstream. Other possible sources of infection include a contaminated infusate, contamination of the catheter hub-infusion tubing junction, and hospital personnel. The incidence of infection increases the longer the catheter remains in place and any device remaining in situ for more than 72 hours is particularly susceptible. The most common infectious agents include common skin flora such as coagulase-negative staphylococci (*S. epidermidis, S. saprophyticus*) and *Staphylococcus aureus* (particularly MRSA—methicillin-resistant *S. aureus*) which account for ⅔ of all infections. Coagulase-negative staphylococci (CNS) is the most commonly isolated organism from the blood of hospitalized patients. CNS infections tend to be indolent; often occurring after a long latent period between contamination (i.e. exposure of the medical device to CNS bacteria from the skin during implantation) and the onset of clinical illness. Unfortunately, most clinically significant CNS infections are caused by bacterial strains that are resistant to multiple antibiotics, making them particularly difficult to treat. Other organisms known to cause vascular access catheter-related infections include Enterococci (e.g. *E. coli*, VRE—vancomycin-resistant enterococcci), Gram-negative aerobic bacilli, *Pseudomonas aeruginosa, Klebsiella* spp., *Serratia marcescens, Burkholderia cepacia, Citrobacter freundii, Corynebacteria* spp. and *Candida* species.

Most cases of vascular access catheter-related infection require removal of the catheter and treatment with systemic antibiotics (although few antibiotics are effective), with vancomycin being the drug of choice. As mentioned previously, mortality associated with vascular access catheter-related infection is high, while the morbidity and cost associated with treating survivors is also extremely significant.

It is therefore extremely important to develop vascular access catheters capable of reducing the incidence of bloodstream infections. Since it is impossible to predict in advance which catheters will become infected, any catheter expected to be in place longer than a couple of days would benefit from a therapeutic coating capable of reducing the incidence of bacterial colonization of the device. An ideal therapeutic coating would have one or more of the following characteristics: (a) the ability to kill, prevent, or inhibit colonization of a wide array of potential infectious agents including most or all of the species listed above; (b) the ability to kill, prevent, or inhibit colonization of bacteria (such as CNS and VRE) that are resistant to multiple antibiotics; (c) utilize a therapeutic agent unlikely to be used in the treatment of a bloodstream infection should one develop (i.e., one would not want to coat the device with a broad-acting antibiotic, for if a strain of bacteria resistant to the antibiotic were to develop on the device it would jeopardize systemic treatment of the patient since the infecting agent would be resistant to a potentially useful therapeutic).

Several classes of anticancer agents are particularly suitable for incorporation into coatings for vascular catheters, namely, anthracyclines (e.g., doxorubicin and mitoxantrone), fluoropyrimidines (e.g., 5-FU), folic acid antagonists (e.g., methotrexate), and podophylotoxins (e.g., etoposide). These agents have a high degree of antibacterial activity against CNS (*S. epidermidis*) and *Staphylococcus aureus*—the most common causes of vascular catheter infections. Particularly preferred agents are doxorubicin, mitoxantrone, 5-fluorouracil and analogues and derivatives thereof which also have activity against *Escheridia coli* and *Pseudomonas aeruginosa*. It is important to note that not all anticancer agents are suitable for the practice of the present invention as several agents, including 2-mercaptopurine, 6-mercaptopurine, hydroxyurea, cytarabine, cisplatinum, tubercidin, paclitaxel, and camptothecin did not have antibacterial activity against the organisms known to cause vascular access catheter-related infections.

1. Central Venous Catheters

For the purposes of this invention, the term "Central Venous Catheters" should be understood to include any catheter or line that is used to deliver fluids to the large (central) veins of the body (e.g., jugular, pulmonary, femoral, iliac, inferior vena cava, superior vena cava, axillary etc.). Examples of such catheters include central venous catheters, total parenteral nutrition catheters, peripherally inserted central venous catheters, flow-directed balloon-tipped pulmonary artery catheters, long-term central venous access catheters (such as Hickman lines and Broviac catheters). Representative examples of such catheters are described in U.S. Pat. Nos. 3,995,623, 4,072,146 4,096,860, 4,099,528, 4,134,402, 4,180,068, 4,385,631, 4,406,656, 4,568,329, 4,960,409, 5,176,661, 5,916,208.

As described previously, 55,000 cases of bloodstream infections are caused by central venous catheters every year in the United States resulting in 23,000 deaths. The risk of infection increases the longer the catheter remains in place, particularly if it is used beyond 72 hours. Severe complications of central venous catheter infection also include infective endocarditis and suppurative phlebitis of the great veins. If the device becomes infected, it must be replaced at a new site (over-the-wire exchange is not acceptable) which puts the patient at further risk to develop mechanical complications of insertion such as bleeding, pneumothorax and hemothorax. In addition, systemic antibiotic therapy is also required. An effective therapy would reduce the incidence of device infection, reduce the incidence of bloodstream infection, reduce the mortality rate, reduce the incidence of complications (such as endocarditis or suppurative phlebitis), prolong the effectiveness of the central venous catheter and/or reduce the need to replace the catheter. This would result in lower mortality and morbidity for patients with central venous catheters in place.

In a preferred embodiment, doxorubicin, mitoxantrone, 5-fluorouracil and/or etoposide are formulated into a coating applied to the surface of the vascular catheter. The drug(s) can be applied to the central venous catheter system in several manners: (a) as a coating applied to the exterior surface of the intravascular portion of the catheter and/or the segment of the catheter that traverses the skin; (b) as a coating applied to the interior and exterior surface of the intravascular portion of the catheter and/or the segment of the catheter that traverses the skin; (c) incorporated into the polymers which comprise the intravascular portion of the catheter; (d) incorporated into, or applied to the surface of, a subcutaneous "cuff" around the catheter; (e) in solution in the infusate; (f) incorporated into, or applied as a coating to, the catheter hub, junctions and/or infusion tubing; and (g) any combination of the aforementioned.

Drug-coating of, or drug incorporation into, the central venous catheter will allow bacteriocidal drug levels to be achieved locally on the catheter surface, thus reducing the incidence of bacterial colonization of the vascular catheter (and subsequent development of blood borne infection), while producing negligible systemic exposure to the drugs. Although for some agents polymeric carriers are not required for attachment of the drug to the catheter surface, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™

[CT Biomaterials]), acrylic or methacrylic copolymers (e.g., poly(ethylene-co-acrylic acid), cellulose-derived polymers (e.g. nitrocellulose, Cellulose Acetate Butyrate, Cellulose acetate propionate), acrylate and methacrylate copolymers (e.g., poly(ethylene-co-vinyl acetate)) as well as blends thereof.

As central venous catheters are made in a variety of configurations and sizes, the exact dose administered will vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the central venous catheter, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the device, or applied without a polymer carrier, the total dose of doxorubicin applied to the central venous catheter (and the other components of the infusion system) should not exceed 25 mg (range of 0.1 µg to 25 mg). In a particularly preferred embodiment, the total amount of drug applied to the central venous catheter (and the other components of the infusion system) should be in the range of 1 µg to 5 mg. The dose per unit area of the device (i.e. the amount of drug as a function of the surface area of the portion of the device to which drug is applied and/or incorporated) should fall within the range of 0.01 µg-100 µg per $mm^2$ of surface area. In a particularly preferred embodiment, doxorubicin should be applied to the device surface at a dose of 0.1 $µg/mm^2$-10 $µg/mm^2$. As different polymer and non-polymer coatings will release doxorubicin at differing rates, the above dosing parameters should be utilized in combination with the release rate of the drug from the device surface such that a minimum concentration of $10^{-7}$-$10^{-4}$ M of doxorubicin is maintained on the device surface. It is necessary to insure that drug concentrations on the device surface exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the device such that anti-infective activity is maintained for a period ranging from several hours to several months. In a particularly preferred embodiment the drug is released in effective concentrations for a period ranging from 1-30 days. It should be readily evident given the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the device, or applied without a carrier polymer, the total dose of mitoxantrone applied to the central venous catheter (and the other components of the infusion system) should not exceed 5 mg (range of 0.01 µg to 5 mg). In a particularly preferred embodiment, the total amount of drug applied to the central venous catheter (and the other components of the infusion system) should be in the range of 0.1 µg to 1 mg. The dose per unit area of the device (i.e. the amount of drug as a function of the surface area of the portion of the device to which drug is applied and/or incorporated) should fall within the range of 0.01 µg-20 µg per $mm^2$ of surface area. In a particularly preferred embodiment, mitoxantrone should be applied to the device surface at a dose of 0.05 $µg/mm^2$-3 $µg/mm^2$. As different polymer and non-polymer coatings will release mitoxantrone at differing rates, the above dosing parameters should be utilized in combination with the release rate of the drug from the device surface such that a minimum concentration of $10^{-5}$-$10^{-6}$ M of mitoxantrone is maintained on the device surface. It is necessary to insure that drug concentrations on the device surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the surface of the device such that anti-infective activity is maintained for a period ranging from several hours to several months. In a particularly preferred embodiment the drug is released in effective concentrations for a period ranging from 1-30 days. It should be readily evident given the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the device, or applied without a carrier polymer, the total dose of 5-fluorouracil applied to the central venous catheter (and the other components of the infusion system) should not exceed 250 mg (range of 1.0 µg to 250 mg). In a particularly preferred embodiment, the total amount of drug applied to the central venous catheter (and the other components of the infusion system) should be in the range of 10 µg to 25 mg. The dose per unit area of the device (i.e. the amount of drug as a function of the surface area of the portion of the device to which drug is applied and/or incorporated) should fall within the range of 0.1 µg-1 mg per $mm^2$ of surface area. In a particularly preferred embodiment, 5-fluorouracil should be applied to the device surface at a dose of 1.0 $µg/mm^2$-50 $µg/mm^2$. As different polymer and non-polymer coatings will release 5-fluorouracil at differing rates, the above dosing parameters should be utilized in combination with the release rate of the drug from the device surface such that a minimum concentration of $10^{-4}$-$10^{-7}$ M of 5-fluorouracil is maintained on the device surface. It is necessary to insure that drug concentrations on the device surface exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the surface of the device such that anti-infective activity is maintained for a period ranging from several hours to several months. In a particularly preferred embodiment the drug is released in effective concentrations for a period ranging from 1-30 days. It should be readily evident given the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the device, or applied without a carrier polymer, the total dose of etoposide applied to the central venous catheter (and the other components of the infusion system) should not exceed 25 mg (range of 0.1 µg to 25 mg). In a particularly preferred embodiment, the total amount of drug applied to the central venous catheter (and the other components of the infusion system) should be in the range of 1 µg to 5 mg. The dose per unit area of the device (i.e. the amount of drug as a function of the surface area of the portion of the device to which drug is applied and/or incorporated) should fall within the range of 0.01 µg-100 µg per $mm^2$ of surface area. In a particularly preferred embodiment, etoposide should be applied to the device surface at a dose of 0.1 µg/$mm^2$-10 µg/$mm^2$. As different polymer and non-polymer coatings will release etoposide at differing rates, the above dosing parameters should be utilized in combination with the release rate of the drug from the device surface such that a concentration of $10^{-5}$-$10^{-6}$ M of etoposide is maintained on the device surface. It is necessary to insure that drug concentrations on the device surface exceed concentrations of etoposide known to be lethal to a variety of bacteria and fungi (i.e., are in excess of $10^{-5}$ M; although for some embodiments lower drug levels will be sufficient). In a preferred embodiment, etoposide is released from the surface of the device such that anti-infective activity is maintained for a period ranging from several hours to several months. In a particularly preferred embodiment the drug is released in effective concentrations for a period ranging from 1-30 days. It should be readily evident based upon the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the central venous catheter coating. Similarly an anthracycline (e.g., doxorubicin or mitoxantrone), fluoropyrimidine (e.g., 5-fluorouracil), folic acid antagonist (e.g., methotrexate) and/or podophylotoxin (e.g., etoposide) can be combined with traditional antibiotic and/or antifungal agents to enhance efficacy. Since thrombogenicity of the catheter is associated with an increased risk of infection, combinations of anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with antithrombotic and/or antiplatelet agents (for example, heparin, dextran sulphate, danaparoid, lepirudin, hirudin, AMP, adenosine, 2-chloroadenosine, aspirin, phenylbutazone, indomethacin, meclofenamate, hydrochloroquine, dipyridamole, iloprost, ticlopidine, clopidogrel, abcixamab, eptifibatide, tirofiban, streptokinase, and/or tissue plasminogen activator) to enhance efficacy.

2. Peripheral Intravenous Catheters

For the purposes of this invention, the term "Peripheral Venous Catheters" should be understood to include any catheter or line that is used to deliver fluids to the smaller (peripheral) superficial veins of the body.

Peripheral venous catheters have a much lower rate of infection than do central venous catheters, particularly if they are in place for less than 72 hours. One exception is peripheral catheters inserted into the femoral vein (so called "femoral lines") which have a significantly higher rate of infection. The organisms that cause infections in a peripheral venous catheter are identical to those described above (for central venous catheters).

In a preferred embodiment, doxorubicin, mitoxantrone, 5-fluorouracil and/or etoposide are formulated into a coating applied to the surface of the peripheral vascular catheter. The drug(s) can be applied to the peripheral venous catheter system in several manners: (a) as a coating applied to the exterior and/or interior surface of the intravascular portion of the catheter and/or the segment of the catheter that traverses the skin; (b) incorporated into the polymers which comprise the intravascular portion of the catheter; (c) incorporated into, or applied to the surface of, a subcutaneous "cuff" around the catheter; (e) in solution in the infusate; (f) incorporated into, or applied as a coating to, the catheter hub, junctions and/or infusion tubing; and (g) any combination of the aforementioned.

The formulation and dosing guidelines for this embodiment are identical to those described for central venous catheters.

3. Arterial Lines and Transducers

Arterial lines are used to draw arterial blood gasses, obtain accurate blood pressure readings and to deliver fluids. They are placed in a peripheral artery (typically the radial artery) and often remain in place for several days. Arterial lines have a very high rate of infection (12-20% of arterial lines become infected) and the causative organisms are identical to those described above (for central venous catheters).

In a preferred embodiment, doxorubicin, mitoxantrone, 5-fluorouracil and/or etoposide are formulated into a coating applied to the arterial line in several manners: (a) as a coating applied to the exterior and/or interior surface of the intravascular portion of the catheter and/or the segment of the catheter that traverses the skin; (b) incorporated into the polymers which comprise the intravascular portion of the catheter; (c) incorporated into, or applied to the surface of, a subcutaneous "cuff" around the catheter; (e) in solution in the infusate; (f) incorporated into, or applied as a coating to, the catheter hub, junctions and/or infusion tubing; and (g) any combination of the aforementioned.

The formulation and dosing guidelines for this embodiment are identical to those described for central venous catheters.

B. Prosthetic Heart Valve Endocarditis (PVE)

Prosthetic heart valves, mechanical and bioprosthetic, are at a significant risk for developing an infection. In fact, 3-6% of patients develop valvular infection within 5 years of valve replacement surgery and prosthetic valve endocarditis accounts for up to 15% of all cases of endocarditis. The risk of developing an infection is not uniform—the risk is greatest in the first year following surgery with a peak incidence between the second and third month postoperatively. Mechanical valves in particular are susceptible to infection in the 3 months following surgery and the microbiology is suggestive of nosocomial infection. Therefore, a drug coating designed to prevent colonization and infection of the valves in the months following surgery could be of great benefit in the prevention of this important medical problem. The incidence of prosthetic valve endocarditis has not changed in the last 40 years despite significant advances in surgical and sterilization technique.

Representative examples of prosthetic heart valves include those described in U.S. Pat. Nos. 3,656,185, 4,106,129, 4,892,540, 5,528,023, 5,772,694, 6,096,075, 6,176,877, 6,358,278, and 6,371,983

Early after valve implantation, the prosthetic valve sewing ring and annulus are not yet endothelialized. The accumulation of platelets and thrombus at the site provide an excellent location for the adherence and colonization of microorganisms. Bacteria can be seeded during the surgical procedure itself or as a result of bacteremia arising in the early postoperative period (usually contamination from i.v. catheters, catheters to determine cardiac output, mediastinal tubes, chest tubes or wound infections). Common causes of PVE include Coagulase Negative Staphylococci (*Staphylococcus epidermidis;* 30%), *Staphylococcus aureus* (23%), Gram Negative Enterococci (Enterobacteriaceae, *Pseudomonas arugenosa;* 14%), Fungi (*Candida albicans, Aspergillis:* 12%), and *Corynebacterium diptheriae*. PVE of biopros-thetic valves is largely confined to the leaflets (and rarely the annulus), whereas the annulus is involved in the majority of cases of PVE in mechanical valves (82%).

Unfortunately, eradication of the infecting organism with antimicrobial therapy alone is often difficult or impossible. As a result, many patients who develop this complication require repeat open-heart surgery to replace the infected valve resulting in significant morbidity and mortality. Even if the infection is successfully treated medically, damage to the leaflets in bioprosthetic valves reduces the lifespan of the valve. Particularly problematic are patients who develop an infection caused by *Staphylococcus aureus*, as they have a 50-85% mortality rate and overall reoperation rate of 50-65%. Infections caused by *Staphylococcus epidermidis* are also difficult to treat as the majority are caused by organisms resistant to all currently available beta-lactam antibiotics. Other complications of prosthetic valve endocarditis include valve malfunction (stenosis, regurgitation), abscess formation, embolic complications (such as stroke, CNS hemorrhage, cerebritis), conduction abnormalities, and death (55-75% of patients who develop an infection in the first 2 months after surgery).

An effective therapeutic valve coating would reduce the incidence of prosthetic valve endocarditis, reduce the mortality rate, reduce the incidence of complications, prolong the effectiveness of the prosthetic valve and/or reduce the need to replace the valve. This would result in lower mortality and morbidity for patients with prosthetic heart valves.

In a preferred embodiment, doxorubicin, mitoxantrone, 5-fluorouracil and/or etoposide are formulated into a coating applied to the surface of the bioprosthetic or mechanical valve. The drug(s) can be applied to the prosthetic valve in several manners: (a) as a coating applied to the surface of the annular ring (particularly mechanical valves); (b) as a coating applied to the surface of the valve leaflets (particularly bioprosthetic valves); (c) incorporated into the polymers which comprise the annular ring; and/or (d) any combination of the aforementioned.

Drug-coating of, or drug incorporation into prosthetic heart valves will allow bacteriocidal drug levels to be achieved locally on the valvular surface, thus reducing the incidence of bacterial colonization and subsequent development of PVE, while producing negligible systemic exposure to the drugs. Although for some agents polymeric carriers are not required for attachment of the drug to the valve annular ring and/or leaflets, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g., nitrocellulose, Cellulose Acetate Butyrate, Cellulose acetate propionate), acrylate and methacrylate copolymers (e.g., poly(ethylene-co-vinyl acetate)), as well as blends thereof.

As prosthetic heart valves are made in a variety of configurations and sizes, the exact dose administered will vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the prosthetic heart valve, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the prosthetic heart valve, or applied without a carrier polymer, the total dose of doxorubicin applied to the prosthetic heart valve should not exceed 25 mg (range of 0.1 µg to 25 mg). In a particularly preferred embodiment, the total amount of drug applied to the prosthetic heart valve should be in the range of 1 µg to 5 mg. The dose per unit area of the valve (i.e., the amount of drug as a function of the surface area of the portion of the valve to which drug is applied and/or incorporated) should fall within the range of 0.01 µg-100 µg per mm$^2$ of surface area. In a particularly preferred embodiment, doxorubicin should be applied to the valve surface at a dose of 0.1 µg/mm$^2$-10 µg/mm$^2$. As different polymer and non-polymer coatings will release doxorubicin at differing rates, the above dosing parameters should be utilized in combination with the release rate of the drug from the valve surface such that a minimum concentration of $10^{-7}$-$10^{-4}$ M of doxorubicin is maintained on the surface. It is necessary to insure that drug concentrations on the valve surface exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the valve such that anti-infective activity is maintained for a period ranging from several hours to several months. In a particularly preferred embodiment the drug is released in effective concentrations for a period ranging from 1-6 months. It should be readily evident based upon the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the prosthetic heart valve, or applied without a carrier polymer, the total dose of mitoxantrone applied to the prosthetic heart valve should not exceed 5 mg (range of 0.01 µg to 5 mg). In a particularly preferred embodiment, the total amount of drug applied to the prosthetic heart valve should be in the range of 0.1 µg to 1 mg. The dose per unit area of the valve (i.e. the amount of drug as a function of the surface area of the portion of the valve to which drug is applied and/or incorporated) should fall within the range of 0.01 µg-20 µg per mm$^2$ of surface area. In a particularly preferred embodiment, mitoxantrone should be applied to the valve surface at a dose of 0.05 µg/mm$^2$-3 µg/mm$^2$. As different polymer and non-polymer coatings will release mitoxantrone at differing rates, the above dosing parameters should be utilized in combination with the release rate of the drug from the valve surface such that a minimum concentration of $10^{-5}$-$10^{-6}$ M of mitoxantrone is maintained on the valve surface. It is necessary to insure that drug concentrations on the valve surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the surface of the valve such that anti-infective activity is maintained for a period ranging from several hours to several months. In a particularly preferred embodiment the drug is released in effective concentrations for a period ranging from 1-6 months. It should be readily evident based upon the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the prosthetic heart valve, or applied without a carrier polymer, the total dose of 5-fluorouracil applied to the prosthetic heart valve should not exceed 250 mg (range of 1.0 µg to 250 mg). In a particularly preferred embodiment, the total amount of drug applied to the prosthetic heart valve should be in the range of 10 µg to 25 mg. The dose per unit area of the valve (i.e. the amount of drug as a function of the surface area of the portion of the valve to which drug is applied and/or incorporated) should fall within the range of 0.1 µg-1 mg per mm$^2$ of surface area. In a particularly preferred embodiment, 5-fluorouracil should be applied to the valve surface at a dose of 1.0 µg/mm$^2$-50 µg/mm$^2$. As different polymer and non-polymer coatings will release 5-fluorouracil at differing rates, the above dosing parameters should be utilized in combination with the release rate of the drug from the valve surface such that a minimum concentration of $10^{-4}$-$10^{-7}$ M of 5-fluorouracil is maintained on the valve surface. It is necessary to insure that drug concentrations on the prosthetic heart valve surface exceed concentrations of 5-fluorouracil known to be lethal to numerous species of bacteria and fungi (i.e., are in excess of $10^4$ M; although for some embodiments lower drug levels will be sufficient). In a preferred embodiment, 5-fluorouracil is released from the surface of the valve such that anti-infective activity is maintained for a period ranging from several hours to several months. In a particularly preferred embodiment the drug is released in effective concentrations for a period ranging from 1-6 months. It should be readily evident based upon the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g., a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the prosthetic heart valve, or applied without a carrier polymer, the total dose of etoposide applied to the prosthetic heart valve should not exceed 25 mg (range of 0.1 µg to 25 mg). In a particularly preferred embodiment, the total amount of drug applied to the prosthetic heart valve should be in the range of 1 µg to 5 mg. The dose per unit area of the valve (i.e., the amount of drug as a function of the surface area of the portion of the valve to which drug is applied and/or incorporated) should fall within the range of 0.01 µg-100 µg per mm$^2$ of surface area. In a particularly preferred embodiment, etoposide should be applied to the prosthetic heart valve surface at a dose of 0.1 µg/mm$^2$-10 µg/mm$^2$. As different polymer and non-polymer coatings will release etoposide at differing rates, the above dosing parameters should be utilized in combination with the release rate of the drug from the valve surface such that a concentration of $10^{-5}$-$10^{-6}$ M of etoposide is maintained on the valve surface. It is necessary to insure that drug concentrations on the valve surface exceed concentrations of etoposide known to be lethal to a variety of bacteria and fungi (i.e., are in excess of $10^{-5}$ M; although for some embodiments lower drug levels will be sufficient). In a preferred embodiment, etoposide is released from the surface of the valve such that anti-infective activity is maintained for a period ranging from several hours to several months. In a particularly preferred embodiment the drug is released in effective concentrations for a period ranging from 1-6 months. It should be readily evident based upon the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be utilized to enhance the antibacterial activity of the prosthetic heart valve coating. Similarly anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with traditional antibiotic and/or antifungal agents to enhance efficacy. Since thrombogenicity of the prosthetic heart valve is associated with an increased risk of infection, anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with antithrombotic and/or antiplatelet agents (for example, heparin, dextran sulphate, danaparoid, lepirudin, hirudin, AMP, adenosine, 2-chloroadenosine, aspirin, phenylbutazone, indomethacin, meclofenamate, hydrochloroquine, dipyridamole, iloprost, ticlopidine, clopidogrel, abcixamab, eptifibatide, tirofiban, streptokinase, and/or tissue plasminogen activator) to enhance efficacy.

C. Cardiac Pacemaker Infections

Overall, slightly greater than 5% of cardiac pacemakers become infected following implantation. Cardiac pacemakers are subject to infection in two general manners: (a) infections involving the pulse generator pocket and/or subcutaneous portion of the lead, and (b) infections involving the transvenous intravascular electrode and/or the generator unit. Representative examples of patents which describe pacemakers and pacemaker leads include U.S. Pat. Nos. 4,662,382, 4,782,836, 4,856,521, 4,860,751, 5,101,824, 5,261,419, 5,284,491, 6,055,454, 6,370,434, and 6,370,434.

The most common type of pacemaker infection involves the subcutaneous generator unit or lead wires in the period shortly after placement. This type of infection is thought to be the result of contamination of the surgical site by skin flora at the time of placement. *Staphylococcus epidermidis* (65-75% of cases), *Stapylococcus aureus*, Streptococci, *Corynebacterium*, *Proprionibacterium acnes*, Enterobacteriaceae and *Candida* species are frequent causes of this type of infection. Treatment of the infection at this point is relatively straightforward, the infected portion of the device is removed, the patient is treated with antibiotics and a new pacemaker is inserted at a different site. Unfortunately, infections of the generator pocket can subsequently spread to the epicardial electrodes causing more severe complications such pericarditis, mediastinitis and bacteremia.

Infection of the intravascular portion of the tranvenous electrode poses a more significant clinical problem. This infection is thought to be caused by infection of the subcutaneous portion of the pacing apparatus that tracks along the device into the intravascular and intracardiac portions of the device. This infection tends to present at a later time (1-6 months post-procedure) and can result in sepsis, endocarditis, pneumonia, bronchitis, pulmonary embolism, cardiac vegetations and even death. Coagulase Negative Staphylococci (56% of infections), *Staphylococcus aureus* (27%), Enterobacteriaceae (6%), *Pseudomonas arugenosa* (3%) and *Candida albicans* (2%) are the most common cause of this serious form of pacemaker infection. Treatment of this form of infection is more complex. The generator and electrodes must be removed (often surgically), antibiotics are required for prolonged periods and an entire new pacemaker system must be inserted. Mortality rates associated with this condition can be quite high—41% if treated with antibiotics alone, 20% if treated with electrode removal and antibiotics.

An effective cardiac pacemaker coating would reduce the incidence of subcutaneous infection and subsequent tracking of infection to the pericardial and endocardial surfaces of the heart. Clinically, this would result in a reduction in the overall rate of infection and reduce the incidence of more severe complications such as sepsis, endocarditis, pneumonia, bronchitis, pulmonary embolism, cardiac vegetations and even death. An effective coating could also prolong the effectiveness of the pacemaker and decrease the number of pacemakers requiring replacement, resulting in lower mortality and morbidity for patients with these implants.

In a preferred embodiment, an anthracycline (e.g., doxorubicin and mitoxantrone), fluoropyrimidine (e.g., 5-FU), folic acid antagonist (e.g., methotrexate), and/or podophylotoxin (e.g., etoposide) is formulated into a coating applied to the surface of the components of the cardiac pacemaker. The drug(s) can be applied to the pacemaker in several manners: (a) as a coating applied to the surface of the generator unit; (b) as a coating applied to the surface of the subcutaneous portion of the lead wires; (c) incorporated into, or applied to the surface of, a subcutaneous "cuff" around the subcutaneous insertion site; (d) as a coating applied to the surface of the epicardial electrodes; (e) as a coating applied to the surface of the transvenous electrode; and/or (f) any combination of the aforementioned.

Drug-coating of, or drug incorporation into cardiac pacemakers will allow bacteriocidal drug levels to be achieved locally on the pacemaker surface, thus reducing the incidence of bacterial colonization and subsequent development of infectious complications, while producing negligible systemic exposure to the drugs. Although for some agents polymeric carriers are not required for attachment of the drug to the generator unit, leads and electrodes, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As cardiac pacemakers are made in a variety of configurations and sizes, the exact dose administered will vary with device size, surface area, design and portions of the pacemaker coated. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the cardiac pacemaker, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the pacemaker components, or applied without a carrier polymer, the total dose of doxorubicin applied to the pacemaker should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the pacemaker to which drug is applied and/or incorporated) should fall within the range of 0.01 µg-100 µg per mm$^2$ of surface area. In a particularly preferred embodiment, doxorubicin should be applied to the pacemaker surface at a dose of 0.1 µg/mm$^2$-10 µg/mm$^2$. As different polymer and non-polymer coatings will release doxorubicin at differing rates, the above dosing parameters should be utilized in combination with the release rate of the drug from the pacemaker surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the pacemaker such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the pacemaker, or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the pacemaker to which drug is applied and/or incorporated) should fall within the range of 0.01 µg-20 µg per mm$^2$ of surface area. In a particularly preferred embodiment, mitoxantrone should be applied to the pacemaker surface at a dose of 0.05 µg/mm$^2$-3 µg/mm$^2$. As different polymer and non-polymer coatings will release mitoxantrone at differing rates, the above dosing parameters should be utilized in combination with the release rate of the drug from the pacemaker surface such that a minimum concentration of $10^{-5}$-$10^{-6}$ M of mitoxantrone is maintained. It is necessary to insure that drug concentrations on the pacemaker surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the surface of the pacemaker such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the pacemaker, or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e. the amount of drug as a function of the surface area of the portion of the pacemaker to which drug is applied and/or incorporated) should fall within the range of 0.1 µg-1 mg per mm$^2$ of surface area. In a particularly preferred embodiment, 5-fluorouracil should be applied to the pacemaker surface at a dose of 1.0 µg/mm$^2$-50 µg/mm$^2$. As different polymer and non-polymer coatings will release 5-fluorouracil at differing rates, the above dosing parameters should be utilized in combination with the release rate of the drug from the pacemaker surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the pacemaker surface such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the cardiac pacemaker, or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the pacemaker to which drug is applied and/or incorporated) should fall within the range of 0.01 µg-100 µg per mm$^2$ of surface area. In a particularly preferred embodiment, etoposide should be applied to the pacemaker surface at a dose of 0.1 µg/mm$^2$-10 µg/mm$^2$. As different polymer and non-polymer coatings will release etoposide at differing rates, the above dosing parameters should be utilized in combination with the release rate of the drug from the pacemaker surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the pacemaker such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be utilized to enhance the antibacterial activity of the pacemaker coating. Similarly anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with traditional antibiotic and/or antifungal agents to enhance efficacy. Since thrombogenicity of the intravascular portion of the transvenous electrode is associated with an increased risk of infection, anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with antithrombotic and/or antiplatelet agents (for example heparin, dextran sulphate, danaparoid, lepirudin, hirudin, AMP, adenosine, 2-chloroadenosine, aspirin, phenylbutazone, indomethacin, meclofenamate, hydrochloroquine, dipyridamole, iloprost, ticlopidine, clopidogrel, abcixamab, eptifibatide, tirofiban, streptokinase, and/or tissue plasminogen activator) to enhance efficacy.

D. Infections of Implantable Cardioverter-Defibrillators (ICD)

Overall, approximately 5-10% of implantable cardioverter-defibrillators become infected following implantation (the rate is highest if surgical placement is required). Like cardiac pacemakers, implantable defibrillators are subject to infection in two general manners: (a) infections involving the subcutaneous portion of the device (subcutaneous electrodes and pulse generator unit, and (b) infections involving the intrathoracic components (rate sensing electrode, SVC coil electrode and epicardial electrodes). Representative examples of ICD's and associated components are described in U.S. Pat. Nos. 3,614,954, 3,614,955, 4,375,817, 5,314,430, 5,405,363, 5,607,385, 5,697,953, 5,776,165, 6,067,471, 6,169,923, and 6,152,955.

Most infections present period shortly after placement and are thought to be the result of contamination of the surgical site by skin flora. *Staphylococcus epidermidis, Stapylococcus aureus*, Streptococci, *Corynebacterium, Proprionibacterium acnes*, Enterobacteriaceae and *Candida* species are frequent causes of this type of infection. Unfortunately, treatment frequently involves removal of the entire system and prolonged antibiotic therapy.

An effective ICD coating would reduce the incidence of infection-related side effects such subcutaneous infection, sepsis and pericarditis. An effective coating could also prolong the effectiveness of the ICD and decrease the number of patients requiring replacement, resulting in lower mortality and morbidity associated with these implants.

In a preferred embodiment, doxorubicin, mitoxantrone, 5-fluorouracil and/or etoposide are formulated into a coating applied to the surface of the components of the ICD. The drug(s) can be applied in several manners: (a) as a coating applied to the surface of the pulse generator unit; (b) as a coating applied to the surface of the subcutaneous portion of the lead wires; (c) incorporated into, or applied to the surface of, a subcutaneous "cuff" around the subcutaneous insertion site; (d) as a coating applied to the surface of the SVC coil electrode; (e) as a coating applied to the surface of the epicardial electrode; and/or (f) any combination of the aforementioned.

Drug-coating of, or drug incorporation into prosthetic heart valves will allow bacteriocidal drug levels to be achieved locally on the ICD surface, thus reducing the incidence of bacterial colonization and subsequent development of infectious complications, while producing negligible systemic exposure to the drugs. Although for some agents polymeric carriers are not required for attachment of the drug to the generator unit, leads and electrodes, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As implantable cardioverter-defibrillators have many design features similar to those found in cardiac pacemakers, the dosing guidelines for doxorubicin, mitoxantrone, 5-fluorouracil and etoposide in coating ICDs are identical to those described above for cardiac pacemakers.

E. Vascular Graft Infections

Infection rates for synthetic vascular grafts range from 1-5% and are highest in grafts that traverse the inguinal region (such as aorto-femoral grafts and femoral-popliteal grafts). Although infection can result from extension of an infection from an adjacent contaminated tissue or hematogenous seeding, the most common cause of infection is intraoperative contamination. In fact, more than half of all cases present within the first 3 months after surgery. The most common causes of infection include *Staphylococcus aureus* (25-35% of cases), Enterobacteriaceae, *Pseudomonas aeruginosa*, and Coagulase Negative Staphylococci.

Complications arising from vascular graft infection include sepsis, subcutaneous infection, false aneurysm formation, graft thrombosis, haemorrhage, septic or thrombotic emboli and graft thrombosis. Treatment requires removal of the graft in virtually all cases combined with systemic antibiotics. Often the surgery must be performed in a staged manner (complete resection of the infected graft, debridement of adjacent infected tissues, development of a healthy arterial stump, reperfusion through an uninfected pathway) further adding to the morbidity and mortality associated with this condition. For example, if an aortic graft becomes infected there is a 37% mortality rate and a 21% rate of leg amputation in survivors; for infrainguinal grafts the rates are 18% and 40% respectively.

Representative examples of vascular grafts are described in U.S. Pat. Nos. 3,096,560, 3,805,301, 3,945,052, 4,140,126, 4,323,525, 4,355,426, 4,475,972, 4,530,113, 4,550,447, 4,562,596, 4,601,718, 4,647,416, 4,878,908, 5,024,671, 5,104,399, 5,116,360, 5,151,105, 5,197,977, 5,282,824, 5,405,379, 5,609,624, 5,693,088, and 5,910,168.

An effective vascular graft coating would reduce the incidence of complications such as sepsis, haemorrhage, thrombosis, embolism, amputation and even death. An effective coating would also decrease the number of vascular grafts requiring replacement, resulting in lower mortality and morbidity for patients with these implants.

In a preferred embodiment, an anthracycline (e.g., doxorubicin and mitoxantrone), fluoropyrimidine (e.g., 5-FU), folic acid antagonist (e.g., methotrexate), and/or podophylotoxin (e.g., etoposide) is formulated into a coating applied to the surface of the components of the vascular graft. The drug(s) can be applied in several manners: (a) as a coating applied to the external surface of the graft; (b) as a coating applied to the internal (luminal) surface of the graft; and/or (c) as a coating applied to all or parts of both surfaces.

Drug-coating of, or drug incorporation into vascular grafts will allow bacteriocidal drug levels to be achieved locally on the graft surface, thus reducing the incidence of bacterial colonization and subsequent development of infectious complications, while producing negligible systemic exposure to the drugs. Although for some agents polymeric carriers are not required for attachment of the drug, several polymeric carriers are particularly suitable for use in this embodiment. Of particular interest are polymeric carriers such as polyurethanes (e.g., ChronoFlex AL 85A [CT Biomaterials], HydroMed640™[CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) collagen as well as blends thereof.

As vascular grafts are made in a variety of configurations and sizes, the exact dose administered will vary with device size, surface area, design and portions of the graft coated. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the vascular graft, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the vascular graft components (such as Dacron or Teflon), or applied without a carrier polymer, the total dose of doxorubicin applied should not exceed 25 mg (range of 0.1 μg to 25 mg). In a particularly preferred embodiment, the total amount of drug applied should be in the range of 1 μg to 5 mg. The dose per unit area (i.e. the amount of drug as a function of the surface area of the portion of the vascular graft to which drug is applied and/or incorporated) should fall within the range of 0.01 μg-100 μg per $mm^2$ of surface area. In a particularly preferred embodiment, doxorubicin should be applied to the vascular graft surface at a dose of 0.1 μg/$mm^2$-10 μg/$mm^2$. As different polymer and non-polymer coatings will release doxorubicin at differing rates, the above dosing parameters should be utilized in combination with the release rate of the drug from the vascular graft surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the vascular graft such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the vascular graft (such as Dacron or Teflon), or applied without a carrier polymer, the total dose of mitoxantrone applied should not exceed 5 mg (range of 0.01 μg to 5 mg). In a particularly preferred embodiment, the total amount of drug applied should be in the range of 0.1 μg to 1 mg. The dose per unit area (i.e. the amount of drug as a function of the surface area of the portion of the vascular graft to which drug is applied and/or incorporated) should fall within the range of 0.01 μg-20 μg per $mm^2$ of surface area. In a particularly preferred embodiment, mitoxantrone should be applied to the vascular graft surface at a dose of 0.05 μg/$mm^2$-3 μg/$mm^2$. As different polymer and non-polymer coatings will release mitoxantrone at differing rates, the above dosing parameters should be utilized in combination with the release rate of the drug from the vascular graft surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the vascular graft surface such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the vascular graft (such as Dacron or Teflon), or applied without a carrier polymer, the total dose of 5-fluorouracil applied should not exceed 250 mg (range of 1.0 μg to 250 mg). In a particularly preferred embodiment, the total amount of drug applied should be in the range of 10 μg to 25 mg. The dose per unit area (i.e. the amount of drug as a function of the surface area of the portion of the vascular graft to which drug is applied and/or incorporated) should fall within the range of 0.1 μg-1 mg per $mm^2$ of surface area. In a particularly preferred embodiment, 5-fluorouracil should be applied to the vascular graft surface at a dose of 1.0 μg/$mm^2$-50 μg/$mm^2$. As different polymer and non-polymer coatings will release 5-fluorouracil at differing rates, the above dosing parameters should be utilized in combination with the release rate of the drug from the vascular graft surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the vascular graft surface such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the vascular graft (such as Dacron or Teflon), or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the vascular graft to which drug is applied and/or incorporated) should fall within the range of 0.01 µg-100 µg per $mm^2$ of surface area. In a particularly preferred embodiment, etoposide should be applied to the vascular graft surface at a dose of 0.1 µg/$mm^2$-10 µg/$mm^2$. As different polymer and non-polymer coatings will release etoposide at differing rates, the above dosing parameters should be utilized in combination with the release rate of the drug from the vascular graft surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the vascular graft such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate and podophylotoxins (e.g., etoposide) can be utilized to enhance the antibacterial activity of the vascular graft coating. Similarly anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with traditional antibiotic and/or antifungal agents to enhance efficacy. Since thrombogenicity of the vascular graft is associated with an increased risk of infection, anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with antithrombotic and/or antiplatelet agents (for example heparin, dextran sulphate, danaparoid, lepirudin, hirudin, AMP, adenosine, 2-chloroadenosine, aspirin, phenylbutazone, indomethacin, meclofenamate, hydrochloroquine, dipyridamole, iloprost, ticlopidine, clopidogrel, abcixamab, eptifibatide, tirofiban, streptokinase, and/or tissue plasminogen activator) to enhance efficacy.

F. Infections Associated with Ear, Nose and Throat Implants

Bacterial infections involving the ear, nose and throat are common occurrences in both children and adults. For the management of chronic obstruction secondary to persistent infection, the use of implanted medical tubes is a frequent form of treatment. Specifically, chronic otitis media is often treated with the surgical implantation of tympanostomy tubes and chronic sinusitis is frequently treated with surgical drainage and the placement of a sinus stent.

Tympanostomy Tubes

Acute otitis media is the most common bacterial infection, the most frequent indication for surgical therapy, the leading cause of hearing loss and a common cause of impaired language development in children. The cost of treating this condition in children under the age of five is estimated at $5 billion annually in the United States alone. In fact, 85% of all children will have at least one episode of otitis media and 600,000 will require surgical therapy annually. The prevalence of otitis media is increasing and for severe cases surgical therapy is more cost effective than conservative management.

Acute otitis media (bacterial infection of the middle ear) is characterized by Eustachian tube dysfunction leading to failure of the middle ear clearance mechanism. The most common causes of otitis media are *Streptococcus pneumoniae* (30%), *Haemophilus influenza* (20%), *Branhamella catarrhalis* (12%), *Streptococcus pyogenes* (3%), and *Staphylococcus aureus* (1.5%). The end result is the accumulation of bacteria, white blood cells and fluid which, in the absence of an ability to drain through the Eustachian tube, results in increased pressure in the middle ear. For many cases antibiotic therapy is sufficient treatment and the condition resolves. However, for a significant number of patients the condition becomes frequently recurrent or does not resolve completely. In recurrent otitis media or chronic otitis media with effusion, there is a continuous build-up of fluid and bacteria that creates a pressure gradient across the tympanic membrane causing pain and impaired hearing. Fenestration of the tympanic membrane (typically with placement of a tympanostomy tube) relieves the pressure gradient and facilitates drainage of the middle ear (through the outer ear instead of through the Eustachian tube—a form of "Eustachian tube bypass").

Surgical placement of tympanostomy tubes is the most widely used treatment for chronic otitis media because, although not curative, it improves hearing (which in turn improves language development) and reduces the incidence of acute otitis media. Tympanostomy tube placement is one of the most common surgical procedures in the United States with 1.3 million surgical placements per year. Nearly all younger children and a large percentage of older children require general anaesthesia for placement. Since general anaesthesia has a higher incidence of significant side effects in children (and represents the single greatest risk and cost associated with the procedure), it is desirable to limit the number of anaesthetics that the child is exposed to. Common complications of tympanostomy tube insertion include chronic otorrhea (often due to infection by *S. pneumoniae, H. influenza, Pseudomonas aerugenosa, S. aureus*, or *Candida*), foreign body reaction with the formation of granulation tissue and infection, plugging (usually obstructed by granulation tissue, bacteria and/or clot), tympanic membrane perforation, myringosclerosis, tympanic membrane atrophy (retraction, atelectasis), and cholesteatoma.

An effective tympanostomy tube coating would allow easy insertion, remain in place for as long as is required, be easily removed in the office without anaesthesia, resist infection and prevent the formation of granulation tissue in the tube (which can not only lead to obstruction, but also "tack down" the tube such that surgical removal of the tube under anaesthetic becomes necessary). An effective tympanostomy tube would also reduce the incidence of complications such as chronic otorrhea (often due to infection by *S. pneumoniae, H. influ-*

*enza, Pseudomonas aerugenosa, S. aureus,* or *Candida*); maintain patency (prevent obstruction by granulation tissue, bacteria and/or clot); and/or reduce tympanic membrane perforation, myringosclerosis, tympanic membrane atrophy and cholesteatoma. Therefore, development of a tube which does not become obstructed by granulation tissue, does not scar in place and is less prone to infection (thereby reducing the need to remove/replace the tube) would be a significant medical advancement.

In a preferred embodiment, doxorubicin, mitoxantrone, 5-fluorouracil and/or etoposide are formulated into a coating applied to the surface of the tympanostomy tube. The drug(s) can be applied in several manners: (a) as a coating applied to the external surface of the tympanostomy tube; (b) as a coating applied to the internal (luminal) surface of the tympanostomy tube; (c) as a coating applied to all or parts of both surfaces; and/or (d) incorporated into the polymers which comprise the tympanostomy tube.

Drug-coating of, or drug incorporation into, the tympanostomy tube will allow bacteriocidal drug levels to be achieved locally on the tube surface, thus reducing the incidence of bacterial colonization (and subsequent development of middle ear infection), while producing negligible systemic exposure to the drugs. Although for some agents polymeric carriers are not required for attachment of the drug to the tympanostomy tube surface, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

There are two general designs of tympanostomy tubes: grommet-shaped tubes, which tend to stay in place for less than 1 year but have a low incidence of permanent perforation of the tympanic membrane (1%), and T-tubes, which stay in place for several years but have a higher rate of permanent perforation (5%). As tympanostomy tubes are made in a variety of configurations and sizes, the exact dose administered will vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the tympanostomy tube, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the tympanostomy tube components, or applied without a carrier polymer, the total dose of doxorubicin applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the tympanostomy tube to which drug is applied and/or incorporated) should fall within the range of 0.01 µg-100 µg per $mm^2$ of surface area. In a particularly preferred embodiment, doxorubicin should be applied to the tympanostomy tube surface at a dose of 0.1 µg/$mm^2$-10 µg/$mm^2$. As different polymer and non-polymer coatings will release doxorubicin at differing rates, the above dosing parameters should be utilized in combination with the release rate of the drug from the tympanostomy tube surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the tympanostomy tube such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the tympanostomy tube, or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the tympanostomy tube to which drug is applied and/or incorporated) should fall within the range of 0.01 µg-20 µg per $mm^2$ of surface area. In a particularly preferred embodiment, mitoxantrone should be applied to the tympanostomy tube surface at a dose of 0.05 µg/$mm^2$-3 µg/$mm^2$. As different polymer and non-polymer coatings will release mitoxantrone at differing rates, the above dosing parameters should be utilized in combination with the release rate of the drug from the tympanostomy tube surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the tympanostomy tube surface such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the tympanostomy tube, or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e. the amount of drug as a function of the surface area of the portion of the tympanostomy tube to which drug is applied and/or incorporated) should fall within the range of 0.1 µg-1 mg per $mm^2$ of surface area. In a particularly preferred embodiment, 5-fluorouracil should be applied to the tympanostomy tube surface at a dose of 1.0 µg/$mm^2$-50 µg/$mm^2$. As different polymer and non-polymer coatings will release 5-fluorouracil at differing rates, the above dosing parameters should be utilized in combination with the release rate of the drug from the tympanostomy tube surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the tympanostomy tube surface such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the tympanostomy tube, or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the tympanostomy tube to which drug is applied and/or incorporated) should fall within the range of 0.01 µg-100 µg per $mm^2$ of surface area. In a particularly preferred embodiment, etoposide should be applied to the tympanostomy tube surface at a dose of 0.1 µg/$mm^2$-10 µg/$mm^2$. As different polymer and non-polymer coatings will release etoposide at differing rates, the above dosing parameters should be utilized in combination with the release rate of the drug from the tympanostomy tube surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the tympanostomy tube such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the tympanostomy tube coating. Similarly anthracyclines (e.g., doxorubicin or mitoxantrone), fluoropyrimidines (e.g., 5-fluorouracil), folic acid antagonists (e.g., methotrexate) and/or podophylotoxins (e.g., etoposide) can be combined with traditional antibiotic and/or antifungal agents to enhance efficacy.

Sinus Stents

The sinuses are four pairs of hollow regions contained in the bones of the skull named after the bones in which they are located (ethmoid, maxillary, frontal and sphenoid). All are lined by respiratory mucosa which is directly attached to the bone. Following an inflammatory insult such as an upper respiratory tract infection or allergic rhinitis, a purulent form of sinusitis can develop. Occasionally secretions can be retained in the sinus due to altered ciliary function or obstruction of the opening (ostea) that drains the sinus. Incomplete drainage makes the sinus prone to infection typically with *Haemophilus influenza, Streptococcus pneumoniae, Moraxella catarrhalis, Veillonella, Peptococcus, Corynebacterium acnes* and certain species of fungi.

When initial treatment such as antibiotics, intranasal steroid sprays and decongestants are ineffective, it may become necessary to perform surgical drainage of the infected sinus. Surgical therapy often involves debridement of the ostea to remove anatomic obstructions and removal of parts of the mucosa. Occasionally a stent (a cylindrical tube which physically holds the lumen of the ostea open) is left in the osta to ensure drainage is maintained even in the presence of post-operative swelling. Stents, typically made of stainless steel or plastic, remain in place for several days or several weeks before being removed.

Unfortunately, the stents can become infected or overgrown by granulation tissue that renders them ineffective. An effective sinus stent coating would allow easy insertion, remain in place for as long as is required, be easily removed in the office without anaesthesia, resist infection and prevent the formation of granulation tissue in the stent (which can not only lead to obstruction, but also "tack down" the stent such that surgical removal becomes necessary). Therefore, development of a sinus stent which does not become obstructed by granulation tissue, does not scar in place and is less prone to infection would be beneficial.

In a preferred embodiment, doxorubicin, mitoxantrone, 5-fluorouracil and/or etoposide are formulated into a coating applied to the surface of the sinus stent. The drug(s) can be applied in several manners: (a) as a coating applied to the external surface of the sinus stent; (b) as a coating applied to the internal (luminal) surface of the sinus stent; (c) as a coating applied to all or parts of both surfaces; and/or (d) incorporated into the polymers which comprise the sinus stent.

Drug-coating of, or drug incorporation into, the sinus stent will allow bacteriocidal drug levels to be achieved locally on the tube surface, thus reducing the incidence of bacterial colonization (and subsequent development of sinusitis), while producing negligible systemic exposure to the drugs.

Although for some agents polymeric carriers are not required for attachment of the drug to the sinus stent surface, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As sinus stents are prone to the same complications and infections from the same bacteria, the dosing guidelines for doxorubicin, mitoxantrone, 5-fluorouracil and etoposide in coating sinus stents are identical to those described above for tympanostomy tubes.

G. Infections Associated with Urological Implants

Implanted medical devices are used in the urinary tract with greater frequency than in any other body system and have some of the highest rates of infection. In fact, the great majority of urinary devices become infected if they remain in place for a prolonged period of time and are the most common cause of nosocomial infection.

Urinary (Foley) Catheters

Four-to-five million bladder catheters are inserted into hospitalized patients every year in the United States. The duration of catheterization is the important risk factor for patients developing a clinically significant infection—the rate of infection increases 5-10% per day that the patient is catheterized. Although simple cystitis can be treated with a short course of antibiotics (with or without removal of the catheter), serious complications are frequent and can be extremely serious. The infection can ascend to the kidneys causing acute pyelonephritis which can result in scarring and long term kidney damage. Perhaps of greatest concern is the 1-2% risk of developing gram negative sepsis (the risk is 3-times higher in catheterized patients and accounts for 30% of all cases) which can be extremely difficult to treat and can result in septic shock and death (up to 50% of patients). Therefore, there exists a significant medical need to produce improved urinary catheters capable of reducing the incidence of urinary tract infection in catheterized patients.

The most common cause of infection is bacteria typically found in the bowel or perineum that are able to track up the catheter to gain access to the normally sterile bladder. Bacteria can be carried into the bladder as the catheter is inserted, gain entry via the sheath of exudates that surrounds the catheter, and/or travel intraluminally inside the catheter tubing. Several species of bacteria are able to adhere to the catheter and form a biofilm that provides a protected site for growth. With short-term catheterization, single organism infections are most common and are typically due to *Escherichia coli*, Enterococci, *Pseudomonas aeruginosa, Klebsiella, Proteus, Enterobacter, Staphylococcus epidermidis, Staphylococcus aureus* and *Staphylococcus saprophyticus*. Patients who are catheterized for long periods of time are prone to polymicrobial infections caused by all of the organisms previously mentioned as well as *Providencia stuartii, Morganella morganii* and *Candida*. Antibiotic use either systemically or locally has been largely proven to be ineffective as it tends to result only in the selection of drug-resistant bacteria.

An effective urinary catheter coating would allow easy insertion into the bladder, resist infection and prevent the formation of biofilm in the catheter. An effective coating would prevent or reduce the incidence of urinary tract infection, pyelonephritis, and/or sepsis. In a preferred embodiment, doxorubicin, mitoxantrone, 5-fluorouracil and/or etoposide are formulated into a coating applied to the surface of the urinary catheter. The drug(s) can be applied in several manners: (a) as a coating applied to the external surface of the urinary catheter; (b) as a coating applied to the internal (luminal) surface of the urinary catheter; (c) as a coating applied to all or parts of both surfaces; and/or (d) incorporated into the polymers which comprise the urinary catheter.

Drug-coating of, or drug incorporation into, the urinary catheter will allow bacteriocidal drug levels to be achieved locally on the catheter surface, thus reducing the incidence of bacterial colonization (and subsequent development of urinary tract infection and bacteremia), while producing negligible systemic exposure to the drugs. Although for some agents polymeric carriers are not required for attachment of the drug to the urinary catheter surface, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As urinary catheters (e.g. Foley catheters, suprapubic catheters) are made in a variety of configurations and sizes, the exact dose administered will vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the urinary catheter, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the urinary catheter components, or applied without a carrier polymer, the total dose of doxorubicin applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the urinary catheter to which drug is applied and/or incorporated) should fall within the range of 0.01 µg-100 µg per mm$^2$ of surface area. In a particularly preferred embodiment, doxorubicin should be applied to the urinary catheter surface at a dose of 0.1 µg/mm$^2$-10 µg/mm$^2$. As different polymer and non-polymer coatings will release doxorubicin at differing rates, the above dosing parameters should be utilized in combination with the release rate of the drug from the urinary catheter surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the urinary catheter such that anti-infective activity is maintained for a period ranging from several hours to several months. In a particularly preferred embodiment the drug is released in effective concentrations for a period ranging from 1 hour-1 month. It should be readily evident given the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the urinary catheter, or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the urinary catheter to which drug is applied and/or incorporated) should fall within the range of 0.01 µg-20 µg per mm$^2$ of surface area. In a particularly preferred embodiment, mitoxantrone should be applied to the urinary catheter surface at a dose of 0.05 µg/mm$^2$-3 µg/mm$^2$. As different polymer and non-polymer coatings will release mitoxantrone at differing rates, the above dosing parameters should be utilized in combination with the release rate of the drug from the urinary catheter surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the urinary catheter surface such that anti-infective activity is maintained for a period ranging from several hours to several months. In a particularly preferred embodiment the drug is released in effective concentrations for a period ranging from 1 hour-1 month. It should be readily evident given the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the urinary catheter, or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e. the amount of drug as a function of the surface area of the portion of the urinary catheter to which drug is applied and/or incorporated) should fall within the range of 0.1 µg-1 mg per mm$^2$ of surface area. In a particularly preferred embodiment, 5-fluorouracil should be applied to the urinary catheter surface at a dose of 1.0 µg/mm$^2$-50 µg/mm$^2$. As different polymer and non-polymer coatings will release 5-fluorouracil at differing rates, the above dosing parameters should be utilized in combination with the release rate of the drug from the urinary catheter surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the urinary catheter surface such that anti-infective activity is maintained for a period ranging from several hours to several months. In a particularly preferred embodiment the drug is released in effective concentrations for a period ranging from 1 hour-1 month. It should be readily evident given the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the urinary catheter, or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the urinary catheter to which drug is applied and/or incorporated) should fall within the range of 0.01 µg-100 µg per mm$^2$ of surface area. In a particularly preferred embodiment, etoposide should be applied to the urinary catheter surface at a dose of 0.1 µg/mm$^2$-10 µg/mm$^2$. As different polymer and non-polymer coatings will release etoposide at differing rates, the above dosing parameters should be utilized in combination with the release rate of the drug from the urinary catheter surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the urinary catheter such that anti-infective activity is maintained for a period ranging from several hours to several months. In a particularly preferred embodiment the drug is released in effective concentrations for a period ranging from 1 hour-1 month. It should be readily evident given the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the urinary catheter coating. Similarly anthracyclines (e.g., doxorubicin or mitoxantrone), fluoropyrimidines (e.g., 5-fluorouracil), folic acid antagonists (e.g., methotrexate) and podophylotoxins (e.g., etoposide) can be combined with traditional antibiotic and/or antifungal agents to enhance efficacy.

Ureteral Stents

Ureteral stents are hollow tubes with holes along the sides and coils at either end to prevent migration. Ureteral stents are used to relieve obstructions (caused by stones or malignancy), to facilitate the passage of stones, or to allow healing of ureteral anastomoses or leaks following surgery or trauma. They are placed endoscopically via the bladder or percutaneously via the kidney. A microbial biofilm forms on up to 90% of ureteral stents and 30% develop significant bacteruria with the incidence increasing the longer the stent is in place. *Pseudomonas aeruginosa* is the most common pathogen, but Enterococci, *Staphylococcus aureus* and *Candida* also cause infection. Effective treatment frequently requires stent removal in addition to antibiotic therapy.

Unfortunately, ureteral stents can become infected or encrusted with urinary salts that render them ineffective. An effective ureteral stent coating would allow easy insertion, remain in place for as long as is required, be easily removed, resist infection and prevent the formation of urinary salts. Therefore, development of a ureteral stent which does not become obstructed by granulation tissue, does not scar in place and is less prone to infection would be beneficial.

In a preferred embodiment, doxorubicin, mitoxantrone, 5-fluorouracil and/or etoposide are formulated into a coating applied to the surface of the ureteral stent. The drug(s) can be applied in several manners: (a) as a coating applied to the external surface of the ureteral stent; (b) as a coating applied to the internal (luminal) surface of the ureteral stent; (c) as a coating applied to all or parts of both surfaces; and/or (d) incorporated into the polymers which comprise the ureteral stent.

Drug-coating of, or drug incorporation into, the ureteral stent will allow bacteriocidal drug levels to be achieved locally on the stent surface, thus reducing the incidence of bacterial colonization (and subsequent development of pyelonephritis and/or bacteremia), while producing negligible systemic exposure to the drugs. Although for some agents polymeric carriers are not required for attachment of the drug to the ureteral stent surface, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As ureteral stents are prone to the same complications and infections from the same bacteria, the dosing guidelines for doxorubicin, mitoxantrone, 5-fluorouracil and etoposide in coating ureteral stents are identical to those described above for urinary catheters. However, unlike the formulations described for urinary catheters, drug release should occur over a 2 to 24 week period.

Urethral Stents

Urethral stents are used for the treatment of recurrent urethral strictures, detruso-external sphincter dyssynergia and bladder outlet obstruction due to benign prostatic hypertrophy. The stents are typically self-expanding and composed of metal superalloy, titanium, stainless steel or polyurethane. Infections are most often due to Coagulase Negative Staphylococci, *Pseudomonas aeruginosa*, Enterococci, *Staphylococcus aureus, Serratia* and *Candida*. Treatment of infected stents frequently requires systemic antibiotic therapy and removal of the device.

An effective urethral stent coating would allow easy insertion, remain in place for as long as is required, be easily removed, resist infection and prevent the formation of urinary salts. Therefore, development of a urethral stent which does not become obstructed by granulation tissue, does not scar in place and is less prone to infection would be beneficial.

In a preferred embodiment, doxorubicin, mitoxantrone, 5-fluorouracil and/or etoposide are formulated into a coating applied to the surface of the urethral stent. The drug(s) can be applied in several manners: (a) as a coating applied to the external surface of the urethral stent; (b) as a coating applied to the internal (luminal) surface of the urethral stent; (c) as a coating applied to all or parts of both surfaces; and/or (d) incorporated into the polymers which comprise the urethral stent.

Drug-coating of, or drug incorporation into, the urethral stent will allow bacteriocidal drug levels to be achieved locally on the stent surface, thus reducing the incidence of bacterial colonization (and subsequent development of pyelonephritis and/or bacteremia), while producing negligible systemic exposure to the drugs. Although for some agents polymeric carriers are not required for attachment of the drug to the ureteral stent surface, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As urethral stents are prone to the same complications and infections from the same bacteria, the dosing guidelines for doxorubicin, mitoxantrone, 5-fluorouracil and etoposide in coating ureteral stents are identical to those described above for urinary catheters. However, unlike the formulations described for urinary catheters, drug release should occur over a 2 to 24 week period.

Prosthetic Bladder Sphincters

Prosthetic bladder sphincters are used to treat incontinence and generally consist of a periurethral implant. The placement of prosthetic bladder sphincters can be complicated by infection (usually in the first 6 months after surgery) with Coagulase Negative Staphylococci (including *Staphylococcus epidermidis*), *Staphylococcus aureus, Pseudomonas aeruginosa*, Enterococci, *Serratia* and *Candida*. Infection is characterized by fever, erythema, induration and purulent drainage from the operative site. The usual route of infection is through the incision at the time of surgery and up to 3% of prosthetic bladder sphincters become infected despite the best sterile surgical technique. To help combat this, intraoperative irrigation with antibiotic solutions is often employed.

Treatment of infections of prosthetic bladder sphincters requires complete removal of the device and antibiotic therapy; replacement of the device must often be delayed for 3-6 months after the infection has cleared. An effective prosthetic bladder sphincter coating would resist infection and reduce the incidence of re-intervention.

In a preferred embodiment, doxorubicin, mitoxantrone, 5-fluorouracil and/or etoposide are formulated into a coating applied to the surface of the prosthetic bladder sphincter. The drug(s) can be applied in several manners: (a) as a coating applied to the external surface of the prosthetic bladder sphincter; and/or (b) incorporated into the polymers which comprise the prosthetic bladder sphincter.

Drug-coating of, or drug incorporation into, the prosthetic bladder sphincter will allow bacteriocidal drug levels to be achieved locally, thus reducing the incidence of bacterial colonization (and subsequent development of urethritis and/or wound infection), while producing negligible systemic exposure to the drugs. Although for some agents polymeric carriers are not required for attachment of the drug to the prosthetic bladder sphincter surface, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As prosthetic bladder sphincters are prone to infections caused by the same bacteria as occur with urinary catheters, the dosing guidelines for doxorubicin, mitoxantrone, 5-fluorouracil and etoposide in coating prosthetic bladder sphincters are identical to those described above for urinary catheters. However, unlike the formulations described for urinary catheters, drug release should occur over a 2 to 24 week period.

Penile Implants

Penile implants are used to treat erectile dysfunction and are generally flexible rods, hinged rods or inflatable devices with a pump. The placement of penile implants can be complicated by infection (usually in the first 6 months after surgery) with Coagulase Negative Staphylococci (including *Staphylococcus epidermidis*), *Staphylococcus aureus*, *Pseudomonas aeruginosa*, Enterococci, *Serratia* and *Candida*. The type of device or route of insertion does not affect the incidence of infection. Infection is characterized by fever, erythema, induration and purulent drainage from the operative site. The usual route of infection is through the incision at the time of surgery and up to 3% of penile implants become infected despite the best sterile surgical technique. To help combat this, intraoperative irrigation with antibiotic solutions is often employed.

Treatment of infections of penile implants requires complete removal of the device and antibiotic therapy; replacement of the device must often be delayed for 3-6 months after the infection has cleared. An effective penile implant coating would resist infection and reduce the incidence of re-intervention.

In a preferred embodiment, doxorubicin, mitoxantrone, 5-fluorouracil and/or etoposide are formulated into a coating applied to the surface of the penile implant. The drug(s) can be applied in several manners: (a) as a coating applied to the external surface of the penile implant; and/or (b) incorporated into the polymers which comprise the penile implant.

Drug-coating of, or drug incorporation into, the penile implant will allow bacteriocidal drug levels to be achieved locally, thus reducing the incidence of bacterial colonization (and subsequent development of local infection and device failure), while producing negligible systemic exposure to the drugs. Although for some agents polymeric carriers are not required for attachment of the drug to the penile implant surface, several polymeric carriers are particularly suitable for use in this embodiment.

As penile implants are prone to infections caused by the same bacteria as occur with urinary catheters, the dosing guidelines for doxorubicin, mitoxantrone, 5-fluorouracil and etoposide in coating penile implants are identical to those described above for urinary catheters. However, unlike the formulations described for urinary catheters, drug release should occur over a 2 to 24 week period.

H. Infections Associated with Endotracheal and Tracheostomy Tubes

Endotracheal tubes and tracheostomy tubes are used to maintain the airway when ventilatory assistance is required. Endotracheal tubes tend to be used to establish an airway in the acute setting, while tracheostomy tubes are used when prolonged ventilation is required or when there is a fixed obstruction in the upper airway. In hospitalized patients, nosocomial pneumonia occurs 300,000 times per year and is the second most common cause of hospital-acquired infection (after urinary tract infection) and the most common infection in ICU patients. In the intensive care unit, nosocomial pneumonia is a frequent cause death with fatality rates over 50%. Survivors spend on average 2 weeks longer in hospital and the annual cost of treatment is close to $2 billion.

Bacterial pneumonia is the most common cause of excess morbidity and mortality in patients who require intubation. In patients who are intubated electively (i.e. for elective surgery), less than 1% will develop a nosocomial pneumonia. However, patients who are severely ill with ARDS (Adult Respiratory Distress Syndrome) have a greater than 50% chance of developing a nosocomial pneumonia. It is thought that new organisms colonize the oropharynx in intubated patients, are swallowed to contaminate the stomach, are aspirated to inoculate the lower airway and eventually contaminate the endotracheal tube. Bacteria adhere to the tube, form a biolayer and multiply serving as a source for bacteria that can aerosolize and be carried distally into the lungs. Chronic tracheostomy tubes also frequently become colonized with pathogenic bacteria known to cause pneumonia. The most common causes of pneumonia in ventilated patients are *Staphylococcus aureus* (17%), *Pseudomonas aeruginosa* (18%), *Klebsiella pneumoniae* (9%), *Enterobacter* (9%) and *Haemophilus influenza* (5%). Treatment requires aggressive therapy with antibiotics.

An effective endotracheal tube or tracheostomy tube coating would resist infection and prevent the formation of biofilm in the tube. An effective coating would prevent or reduce the incidence of pneumonia, sepsis and death. In a preferred embodiment, doxorubicin, mitoxantrone, 5-fluorouracil and/or etoposide are formulated into a coating applied to the surface of the endotracheal tube or tracheostomy tube. Due to its activity against *Klebsiella pneumoniae*, methotrexate can also be useful for this embodiment. As cisplatin and hydroxyurea have some activity against *Pseudomonas aeruginosa*, they can also be of some utility in the practice of this embodiment. The drug(s) can be applied in several manners: (a) as a coating applied to the external surface of the endotracheal tube or tracheostomy tube; (b) as a coating applied to the internal (luminal) surface of the endotracheal tube or tracheostomy tube; (c) as a coating applied to all or parts of both surfaces; and/or (d) incorporated into the polymers which comprise the endotracheal tube or tracheostomy tube.

Drug-coating of, or drug incorporation into, the endotracheal tube or tracheostomy tube will allow bacteriocidal drug levels to be achieved locally on the catheter surface, thus reducing the incidence of bacterial colonization (and subsequent development of pneumonia and sepsis), while producing negligible systemic exposure to the drugs. Although for some agents polymeric carriers are not required for attachment of the drug to the endotracheal tube or tracheostomy tube surface, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As endotracheal tube and tracheostomy tubes are made in a variety of configurations and sizes, the exact dose administered will vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the endotracheal tube or tracheostomy tube, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the endotracheal tube or tracheostomy tube components, or applied without a carrier polymer, the total dose of doxorubicin applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the endotracheal tube or tracheostomy tube to which drug is applied and/or incorporated) should fall within the range of 0.01 µg-100 µg per mm$^2$ of surface area. In a particularly preferred embodiment, doxorubicin should be applied to the endotracheal tube or tracheostomy tube surface at a dose of 0.1 µg/mm$^2$-10 µg/mm$^2$. As different polymer and non-polymer coatings will release doxorubicin at differing rates, the above dosing parameters should be utilized in combination with the release rate of the drug from the endotracheal tube or tracheostomy tube surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the endotracheal tube or tracheostomy tube such that anti-infective activity is maintained for a period ranging from several hours to several months. In a particularly preferred embodiment the drug is released in effective concentrations from the endotracheal tube for a period ranging from 1 hour to 1 month, while release from a tracheostomy tube would range from 1 day to 3 months. It should be readily evident given the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the endotracheal tube or tracheostomy tube, or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the endotracheal tube or tracheostomy tube to which drug is applied and/or incorporated) should fall within the range of 0.01 µg-20 µg per mm$^2$ of surface area. In a particularly preferred embodiment, mitoxantrone should be applied to the endotracheal tube or tracheostomy tube surface at a dose of 0.05 µg/mm$^2$-3 µg/mm$^2$. As different polymer and non-polymer coatings will release mitoxantrone at differing rates, the above dosing parameters should be utilized in combination with the release rate of the drug from the endotracheal tube or tracheostomy tube surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the endotracheal tube or tracheostomy tube surface such that anti-infective activity is maintained for a period ranging from several hours to several months. In a particularly preferred embodiment, the drug is released in effective concentrations from the endotracheal tube for a period ranging from 1 hour to 1 month, while release from a tracheostomy tube would range from 1 day to 3 months. It should be readily evident given the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the endotracheal tube or tracheostomy tube, or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e. the amount of drug as a function of the surface area of the portion of the endotracheal tube or tracheostomy tube to which drug is applied and/or incorporated) should fall within the range of 0.1 µg-1 mg per mm$^2$ of surface area. In a particularly preferred embodiment, 5-fluorouracil should be applied to the endotracheal tube or tracheostomy tube surface at a dose of 1.0 µg/mm$^2$-50 µg/mm$^2$. As different polymer and non-polymer coatings will release 5-fluorouracil at differing rates, the above dosing parameters should be utilized in combination with the release rate of the drug from the endotracheal tube or tracheostomy tube surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e. are in excess of $10^{-4}$ M; although for some embodiments lower drug levels will be sufficient). In a preferred embodiment, 5-fluorouracil is released from the endotracheal tube or tracheostomy tube surface such that anti-infective activity is maintained for a period ranging from several hours to several months. In a particularly preferred embodiment, the drug is released in effective concentrations from the endotracheal tube for a period ranging from 1 hour to 1 month, while release from a tracheostomy tube would range from 1 day to 3 months. It should be readily evident given the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the endotracheal tube or tracheostomy tube, or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the endotracheal tube or tracheostomy tube to which drug is applied and/or incorporated) should fall within the range of 0.01 µg-100 µg per $mm^2$ of surface area. In a particularly preferred embodiment, etoposide should be applied to the endotracheal tube or tracheostomy tube surface at a dose of 0.1 $µg/mm^2$-10 $µg/mm^2$. As different polymer and non-polymer coatings will release etoposide at differing rates, the above dosing parameters should be utilized in combination with the release rate of the drug from the endotracheal tube or tracheostomy tube surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the endotracheal tube or tracheostomy tube such that anti-infective activity is maintained for a period ranging from several hours to several months. In a particularly preferred, embodiment the drug is released in effective concentrations from the endotracheal tube for a period ranging from 1 hour to 1 month, while release from a tracheostomy tube would range from 1 day to 3 months. It should be readily evident given the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the endotracheal tube or tracheostomy tube coating. Similarly anthracyclines (e.g., doxorubicin or mitoxantrone), fluoropyrimidines (e.g., 5-fluorouracil), folic acid antagonists (e.g., methotrexate) and/or podophylotoxins (e.g., etoposide) can be combined with traditional antibiotic and/or antifungal agents to enhance efficacy.

I. Infections Associated with Dialysis Catheters

In 1997, there were over 300,000 patients in the United States with end-stage renal disease. Of these, 63% were treated with hemodialysis, 9% with peritoneal dialysis and 38% with renal transplantation. Hemodialysis requires reliable access to the vascular system typically as a surgically created arteriovenous fistula (AVF; 18%), via a synthetic bridge graft (usually a PTFE arteriovenous interposition graft in the forearm or leg; 50%) or a central venous catheter (32%). Peritoneal dialysis requires regular exchange of dialysate through the peritoneum via a double-cuffed and tunneled peritoneal dialysis catheter. Regardless of the form of dialysis employed, infection is the second leading cause of death in renal failure patients (15.5% of all deaths) after heart disease. A significant number of those infections are secondary to the dialysis procedure itself.

Hemodialysis Access Grafts

Kidney failure patients have a dysfunctional immune response that makes them particularly susceptible to infection. Infections of hemodialysis access grafts are characterized as either being early (within month; thought to be a complication of surgery) and late (after 1 month; thought to be related to access care). Over a 2 year period, approximately 2% of AVF's become infected while 11-16% of PTFE grafts will become infected on at least one occasion. Although infection can result from extension of an infection from an adjacent contaminated tissue or hematogenous seeding, the most common cause of infection is intraoperative contamination. The most common causes of infection include *Staphylococcus aureus*, Enterobacteriaceae, *Pseudomonas aerugenosa*, and Coagulase Negative Staphylococci.

Complications arising from hemodialysis access graft infection include sepsis, subcutaneous infection, false aneurysm formation, endocarditis, osteomyelitis, septic arthritis, haemorrhage, septic or thrombotic emboli, graft thrombosis and septic death (2-4% of all infections). Treatment often requires removal of part or all of the graft combined with systemic antibiotics.

In a preferred embodiment, doxorubicin, mitoxantrone, 5-fluorouracil and/or etoposide are formulated into a coating applied to the surface of the components of the synthetic hemodialysis access graft. The drug(s) can be applied in several manners: (a) as a coating applied to the external surface of the graft; (b) as a coating applied to the internal (luminal) surface of the graft; and/or (c) as a coating applied to all or parts of both surfaces. For an AVF, the drug would be formulated into a surgical implant placed around the outside of the fistula at the time of surgery.

Drug-coating of, or drug incorporation into hemodialysis access grafts will allow bacteriocidal drug levels to be achieved locally on the graft surface, thus reducing the incidence of bacterial colonization and subsequent development of infectious complications, while producing negligible systemic exposure to the drugs. Although for some agents polymeric carriers are not required for attachment of the drug, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)), collagen, PLG as well as blends thereof.

An effective hemodialysis access graft coating would reduce the incidence of complications such as sepsis, haemorrhage, thrombosis, embolism, endocarditis, osteomyelitis and even death. An effective coating would also decrease the number of hemodialysis access grafts requiring replacement, resulting in lower mortality and morbidity for patients with these implants.

As hemodialysis access grafts are made in a variety of configurations and sizes, the exact dose administered will vary with device size, surface area, design and portions of the graft coated. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the hemodialysis access graft, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the hemodialysis access graft components (such as Dacron or Teflon), or applied without a carrier polymer, the total dose of doxorubicin applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the hemodialysis access graft to which drug is applied and/or incorporated) should fall within the range of 0.01 µg-100 µg per mm$^2$ of surface area. In a particularly preferred embodiment, doxorubicin should be applied to the hemodialysis access graft surface at a dose of 0.1 µg/mm$^2$-10 µg/mm$^2$. As different polymer and non-polymer coatings will release doxorubicin at differing rates, the above dosing parameters should be utilized in combination with the release rate of the drug from the hemodialysis access graft surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the hemodialysis access graft such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the hemodialysis access graft (such as Dacron or Teflon), or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the hemodialysis access graft to which drug is applied and/or incorporated) should fall within the range of 0.01 µg-20 µg per mm$^2$ of surface area. In a particularly preferred embodiment, mitoxantrone should be applied to the hemodialysis access graft surface at a dose of 0.05 µg/mm$^2$-3 µg/mm$^2$. As different polymer and non-polymer coatings will release mitoxantrone at differing rates, the above dosing parameters should be utilized in combination with the release rate of the drug from the hemodialysis access graft surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the hemodialysis access graft surface such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the hemodialysis access graft (such as Dacron or Teflon), or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e. the amount of drug as a function of the surface area of the portion of the hemodialysis access graft to which drug is applied and/or incorporated) should fall within the range of 0.1 µg-1 mg per mm$^2$ of surface area. In a particularly preferred embodiment, 5-fluorouracil should be applied to the hemodialysis access graft surface at a dose of 1.0 µg/mm$^2$-50 µg/mm$^2$. As different polymer and non-polymer coatings will release 5-fluorouracil at differing rates, the above dosing parameters should be utilized in combination with the release rate of the drug from the hemodialysis access graft surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the hemodialysis access graft surface such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the hemodialysis access graft (such as Dacron or Teflon), or applied without a carrier polymer, the total dose of etoposide applied should not exceed 25 mg (range of 0.1 μg to 25 mg). In a particularly preferred embodiment, the total amount of drug applied should be in the range of 1 μg to 5 mg. The dose per unit area (i.e. the amount of drug as a function of the surface area of the portion of the hemodialysis access graft to which drug is applied and/or incorporated) should fall within the range of 0.01 μg-100 μg per $mm^2$ of surface area. In a particularly preferred embodiment, etoposide should be applied to the hemodialysis access graft surface at a dose of 0.1 $μg/mm^2$-10 $μg/mm^2$. As different polymer and non-polymer coatings will release etoposide at differing rates, the above dosing parameters should be utilized in combination with the release rate of the drug from the hemodialysis access graft surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the hemodialysis access graft such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the hemodialysis access graft coating. Similarly anthracyclines (e.g., doxorubicin or mitoxantrone), fluoropyrimidines (e.g., 5-fluorouracil), folic acid antagonists (e.g., methotrexate) and/or podophylotoxins (e.g., etoposide) can be combined with traditional antibiotic and/or antifungal agents to enhance efficacy. Since thrombogenicity of the hemodialysis access graft is associated with an increased risk of infection, anthracyclines (e.g., doxorubicin or mitoxantrone), fluoropyrimidines (e.g., 5-fluorouracil), folic acid antagonists (e.g., methotrexate) and/or podophylotoxins (e.g., etoposide) can be combined with antithrombotic and/or antiplatelet agents (for example heparin, dextran sulphate, danaparoid, lepirudin, hirudin, AMP, adenosine, 2-chloroadenosine, aspirin, phenylbutazone, indomethacin, meclofenamate, hydrochloroquine, dipyridamole, iloprost, ticlopidine, clopidogrel, abciximab, eptifibatide, tirofiban, streptokinase, and/or tissue plasminogen activator) to enhance efficacy.

Central Venous Catheters

A variety of central venous catheters are available for use in hemodialysis including, but not restricted to, catheters which are totally implanted such as the Lifesite (Vasca Inc., Tewksbury, Mass.) and the Dialock (Biolink Corp., Middleboro, Mass.). Central venous catheters are prone to infection and embodiments for that purpose are described above.

Peritoneal Dialysis Catheters

Peritoneal dialysis catheters are typically double-cuffed and tunnelled catheters that provide access to the peritoneum. The most common peritoneal dialysis catheter designs are the Tenckhoff catheter, the Swan Neck Missouri catheter and the Toronto Western catheter. In peritoneal dialysis, the peritoneum acts as a semipermeable membrane across which solutes can be exchanged down a concentration gradient.

Peritoneal dialysis infections are typically classified as either peritonitis or exit-site/tunnel infections (i.e. catheter infections). Exit-site/tunnel infections are characterized by redness, induration or purulent discharge from the exit site or subcutaneous portions of the catheter. Peritonitis is more a severe infection that causes abdominal pain, nausea, fever and systemic evidence of infection. Unfortunately, the peritoneal dialysis catheter likely plays a role in both types of infection. In exit-site/tunnel infections, the catheter itself becomes infected. In peritonitis, the infection is frequently the result of bacteria tracking from the skin through the catheter lumen or migrating on the outer surface (pericatheter route) of the catheter into the peritoneum. Peritoneal catheter-related infections are typically caused by *Staphylococcus aureus*, Coagulase Negative Staphylococci, *Escherichia coli*, Viridans group streptococci, Enterobacteriacae, *Corynebacterium, Branhamella, Actinobacter, Serratia, Proteus, Pseudomonas aeruginosa* and Fungi.

Treatment of peritonitis involves rapid in-and-out exchanges of dialysate, systemic antibiotics (intravenous and/or intraperitoneal administration) and often requires removal of the catheter. Complications include hospitalization, the need to switch to another form of dialysis (30%) and mortality (2%; higher if the infection is due to Enterococci, *S. aureus* or polymicrobial).

In a preferred embodiment, doxorubicin, mitoxantrone, 5-fluorouracil and/or etoposide are formulated into a coating applied to the surface of the components of the synthetic peritoneal dialysis graft. The drug(s) can be applied in several manners: (a) as a coating applied to the external surface of the graft; (b) as a coating applied to the internal (luminal) surface of the graft; (c) as a coating applied to the superficial cuff; (d) as a coating applied to the deep cuff; (e) incorporated into the polymers that comprise the graft; and/or (f) as a coating applied to a combination of these surfaces.

Drug-coating of, or drug incorporation into peritoneal dialysis grafts will allow bacteriocidal drug levels to be achieved locally on the graft surface, thus reducing the incidence of bacterial colonization and subsequent development of infectious complications, while producing negligible systemic exposure to the drugs. Although for some agents polymeric carriers are not required for attachment of the drug, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

An effective peritoneal dialysis graft coating would reduce the incidence of complications such as hospitalization, peritonoitis, sepsis, and even death. An effective coating would also decrease the number of peritoneal dialysis grafts requiring replacement, resulting in lower mortality and morbidity for patients with these implants.

As peritoneal dialysis grafts are made in a variety of configurations and sizes, the exact dose administered will vary with device size, surface area, design and portions of the graft coated. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the peritoneal dialysis graft, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the peritoneal dialysis graft components (such as Dacron or Teflon), or applied without a carrier polymer, the total dose of doxorubicin applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the peritoneal dialysis graft to which drug is applied and/or incorporated) should fall within the range of 0.01 µg-100 µg per $mm^2$ of surface area. In a particularly preferred embodiment, doxorubicin should be applied to the peritoneal dialysis graft surface at a dose of 0.1 $\mu g/mm^2$-10 $\mu g/mm^2$. As different polymer and non-polymer coatings will release doxorubicin at differing rates, the above dosing parameters should be utilized in combination with the release rate of the drug from the peritoneal dialysis graft surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the peritoneal dialysis graft such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the peritoneal dialysis graft (such as Dacron or Teflon), or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the peritoneal dialysis graft to which drug is applied and/or incorporated) should fall within the range of 0.01 µg-20 µg per $mm^2$ of surface area. In a particularly preferred embodiment, mitoxantrone should be applied to the peritoneal dialysis graft surface at a dose of 0.05 $\mu g/mm^2$-3 $\mu g/mm^2$. As different polymer and non-polymer coatings will release mitoxantrone at differing rates, the above dosing parameters should be utilized in combination with the release rate of the drug from the peritoneal dialysis graft surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the peritoneal dialysis graft surface such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the peritoneal dialysis graft (such as Dacron or Teflon), or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e. the amount of drug as a function of the surface area of the portion of the peritoneal dialysis graft to which drug is applied and/or incorporated) should fall within the range of 0.1 µg-1 mg per $mm^2$ of surface area. In a particularly preferred embodiment, 5-fluorouracil should be applied to the peritoneal dialysis graft surface at a dose of 1.0 $\mu g/mm^2$-50 $\mu g/mm^2$. As different polymer and non-polymer coatings will release 5-fluorouracil at differing rates, the above dosing parameters should be utilized in combination with the release rate of the drug from the peritoneal dialysis graft surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the peritoneal dialysis graft surface such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the peritoneal dialysis graft (such as Dacron or Teflon), or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the peritoneal dialysis graft to which drug is applied and/or incorporated) should fall within the range of 0.01 µg-100 µg per $mm^2$ of surface area. In a particularly preferred embodiment, etoposide should be applied to the peritoneal dialysis graft surface at a dose of 0.1 µg/$mm^2$-10 µg/$mm^2$. As different polymer and non-polymer coatings will release etoposide at differing rates, the above dosing parameters should be utilized in combination with the release rate of the drug from the peritoneal dialysis graft surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the peritoneal dialysis graft such that anti-infective activity is maintained for a period ranging from several hours to several months. In a particularly preferred embodiment the drug is released in effective concentrations for a period ranging from 1 week-6 months. It should be readily evident given the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the peritoneal dialysis graft coating. Similarly anthracyclines (e.g., doxorubicin or mitoxantrone), fluoropyrimidines (e.g., 5-fluorouracil), folic acid antagonists (e.g., methotrexate) and/or podophylotoxins (e.g., etoposide) can be combined with traditional antibiotic and/or antifungal agents to enhance efficacy.

J. Infections of Central Nervous System (CNS) Shunts

Hydrocephalus, or accumulation of cerebrospinal fluid (CSF) in the brain, is a frequently encountered neurosurgical condition arising from congenital malformations, infection, hemorrhage, or malignancy. The incompressible fluid exerts pressure on the brain leading to brain damage or even death if untreated. CNS shunts are conduits placed in the ventricles of the brain to divert the flow of CSF from the brain to other body compartments and relieve the fluid pressure. Ventricular CSF is diverted via a prosthetic shunt to a number of drainage locations including the pleura (ventriculopleural shunt), jugular vein, vena cava (VA shunt), gallbladder and peritoneum (VP shunt; most common).

Unfortunately, CSF shunts are relatively prone to developing infection, although the incidence has declined from 25% twenty years ago to 10% at present as a result of improved surgical technique. Approximately 25% of all shunt complications are due to the development of infection of the shunt and these can lead to significant clinical problems such as ventriculitis, ventricular compartmentalization, meningitis, subdural empyema, nephritis (with VA shunts), seizures, cortical mantle thinning, mental retardation or death. Most infections present with fever, nausea, vomiting, malaise, or signs of increased intracranial pressure such as headache or altered consciousness. The most common organisms causing CNS shunt infections are Coagulase Negative Staphylococci (67%; *Staphylococcus epidermidis* is the most frequently isolated organism), *Staphylococcus aureus* (10-20%), viridans streptococci, *Streptococcus pyogenes, Enterococcus, Corynebacterium, Escherichia coli, Klebsiella, Proteus* and *Pseudomonas aeruginosa*. It is thought that the majority of infections are due to inoculation of the organism during surgery, or during manipulation of the shunt in the postoperative period. As a result, most infections present clinically in the first few weeks following surgery.

Since many of the infections are caused by *S. epidermidis*, it is not uncommon to find that the catheter becomes coated with a bacterial-produced "slime" that protects the organism from the immune system and makes eradication of the infection difficult. Therefore, the treatments of most infections require shunt removal (and often placement of a temporary external ventricular shunt to relieve hydrocephalus) in addition to systemic and/or intraventricular antibiotic therapy. Poor therapeutic results tend to occur if the shunt is left in place during treatment. Antibiotic therapy is complicated by the fact that many antibiotics do not cross the blood-brain barrier effectively.

An effective CNS shunt coating would reduce the incidence of complications such as ventriculitis, ventricular compartmentalization, meningitis, subdural empyema, nephritis (with VA shunts), seizures, cortical mantle thinning, mental retardation or death. An effective coating would also decrease the number of CNS shunts requiring replacement, resulting in lower mortality and morbidity for patients with these implants.

In a preferred embodiment, an anthracycline (e.g., doxorubicin and mitoxantrone), fluoropyrimidine (e.g., 5-FU), folic acid antagonist (e.g., methotrexate), and/or podophylotoxin (e.g., etoposide) is formulated into a coating applied to the surface of the components of the CNS shunt. The drug(s) can be applied in several manners: (a) as a coating applied to the external surface of the shunt; (b) as a coating applied to the internal (luminal) surface of the shunt; and/or (c) as a coating applied to all or parts of both surfaces.

Drug-coating of, or drug incorporation into CNS shunts will allow bacteriocidal drug levels to be achieved locally on the shunt surface, thus reducing the incidence of bacterial colonization and subsequent development of infectious complications, while producing negligible systemic exposure to the drugs. Although for some agents polymeric carriers are not required for attachment of the drug, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As CNS shunts are made in a variety of configurations and sizes, the exact dose administered will vary with device size, surface area, design and portions of the shunt coated. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the CNS shunt, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the CNS shunt components (such as Dacron or Teflon), or applied without a carrier polymer, the total dose of doxorubicin applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the CNS shunt to which drug is applied and/or incorporated) should fall within the range of 0.01 µg-100 µg per $mm^2$ of surface area. In a particularly preferred embodiment, doxorubicin should be applied to the CNS shunt surface at a dose of 0.1 µg/$mm^2$-10 µg/$mm^2$. As different polymer and non-polymer coatings will release doxorubicin at differing rates, the above dosing parameters should be utilized in combination with the release rate of the drug from the CNS shunt surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the CNS shunt such that anti-infective activity is maintained for a period ranging from several hours to several months. In a particularly preferred embodiment the drug is released in effective concentrations for a period ranging from 1-12 weeks. It should be readily evident given the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the CNS shunt (such as Dacron or Teflon), or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the CNS shunt to which drug is applied and/or incorporated) should fall within the range of 0.01 µg-20 µg per $mm^2$ of surface area. In a particularly preferred embodiment, mitoxantrone should be applied to the CNS shunt surface at a dose of 0.05 µg/$mm^2$-3 µg/$mm^2$. As different polymer and non-polymer coatings will release mitoxantrone at differing rates, the above dosing parameters should be utilized in combination with the release rate of the drug from the CNS shunt surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the CNS shunt surface such that anti-infective activity is maintained for a period ranging from several hours to several months. In a particularly preferred embodiment the drug is released in effective concentrations for a period ranging from 1-12 weeks. It should be readily evident based upon the discussion provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the CNS shunt (such as Dacron or Teflon), or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e. the amount of drug as a function of the surface area of the portion of the CNS shunt to which drug is applied and/or incorporated) should fall within the range of 0.1 µg-1 mg per $mm^2$ of surface area. In a particularly preferred embodiment, 5-fluorouracil should be applied to the CNS shunt surface at a dose of 1.0 µg/$mm^2$-50 µg/$mm^2$. As different polymer and non-polymer coatings will release 5-fluorouracil at differing rates, the above dosing parameters should be utilized in combination with the release rate of the drug from the CNS shunt surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the CNS shunt surface such that anti-infective activity is maintained for a period ranging from several hours to several months. In a particularly preferred embodiment the drug is released in effective concentrations for a period ranging from 1-12 weeks. It should be readily evident based upon the discussion provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the CNS shunt (such as Dacron or Teflon), or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the CNS shunt to which drug is applied and/or incorporated) should fall within the range of 0.01 µg-100 µg per $mm^2$ of surface area. In a particularly preferred embodiment, etoposide should be applied to the CNS shunt surface at a dose of 0.1 µg/mm$^2$-10 µg/mm$^2$. As different polymer and non-polymer coatings will release etoposide at differing rates, the above dosing parameters should be utilized in combination with the release rate of the drug from the CNS shunt surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the CNS shunt such that anti-infective activity is maintained for a period ranging from several hours to several months. In a particularly preferred embodiment the drug is released in effective concentrations for a period ranging from 1-12 weeks. It should be readily evident based upon the discussion provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the CNS shunt coating. Similarly anthracyclines (e.g., doxorubicin or mitoxantrone), fluoropyrimidines (e.g., 5-fluorouracil), folic acid antagonists (e.g., methotrexate) and/or podophylotoxins (e.g., etoposide) can be combined with traditional antibiotic and/or antifungal agents to enhance efficacy.

(g) External Ventricular Drainage (EVD) Device and Intracranial Pressure (ICP) Monitoring Devices EVD and ICP monitoring devices are also used in the management of hydrocephalus. The therapeutic agents, doses, coatings and release kinetics for the development of drug-coated EVD's and drug-coated ICP monitoring devices are identical to those described for CNS shunts.

K. Infections of Orthopedic Implants

Implanted orthopedic devices such as prosthetic joints such as hip, knee, elbow, shoulder, wrist, metacarpal, and metatarsal prosthetics are subject to complications as a result of infection of the implant. Orthopedic implant infection has a variety of sequela including pain, immobility, failure of the prosthetic itself, loss/removal the of prosthetic, reoperation, loss of the affected limb or even death. The cost of treating each infection exceeds the cost of the primary joint arthroplasty itself by 3 or 4-fold (in excess of $50,000/case). Other orthopedic implant hardware such as internal and external fixation devices, plates and screws are also subject to such infection and infection-related complications. The present treatment includes multiple operations to remove infected prosthetics, with its own inherent risks, combined with antibiotic use.

The rate of orthopedic prosthetic infection is highest in the first month post operatively then declines continuously there after. As an example, the combined incidence of rate of prosthetic joint infection for 2 years is approximately 5.9% per 1,000 joints; the rate then drops to 2.3% per 1,000 joints from year 2 to 10. The rate of infection also varies depending on the joint. Knee prosthetics are infected twice as frequently as hips. Shoulder prosthetic infections range from 0.5% to 3%, elbows up to 12%, wrists 1.5% to 5.0% and ankles 1.4% to 2.4%.

There are three main mechanisms of infection. The most common is colonization of the implant (prosthetic, fixation plate, screws—any implantable orthopedic device) at the time of implant, either directly or through airborne contamination of the wound. The second method is spread from an adjacent focus of infection, such as wound infection, abscess or sinus tract. The third is hematogenous seeding during a systemic bacteremia, likely accounting for approximately 7% of all implant infections.

Risk factors are multiple. The host may be compromised as a result of a systemic condition, an illness, a local condition, or as a result of medications that decrease the host defence capability. There is also a predisposition to infections if the patient has had prior surgery, perioperative wound compilations, or rheumatoid arthritis. Repeat surgical procedures increase the likelihood of infection as there is a reported 8-fold elevated risk of infection as compared to the primary prosthetic replacement procedure. The presence of a deep infection increases the risk of prosthetic infection 6-fold. Various diseases also increase the risk of infection. For example, rheumatoid arthritis patients have a higher risk of infection possibly as a result of medications that compromising their immunocompetency, while psoriatic patients have a higher rate possibly mediated by a compromised skin barrier that allows entry of microbes.

The implant itself, and the cements that secure it in place, can cause a local immunocompromised condition that is poorly understood. Different implant materials have their own inherent rate of infection. For example, a metal-to-metal hinged prosthetic knee has 20-times the risk of infection of a metal-to-plastic knee.

An implanted device is most susceptible to infection early on. Rabbit models have shown that only a few *Staphylococcus aureus* inoculated at the time of implant are required to cause an infection, but bacteremic (hematogenous) seeding at 3 weeks postoperatively is substantially more difficult and requires significantly more bacteria. This emphasizes the importance of an antimicrobial strategy initiated early at the time of implantation.

Sixty five percent of all prosthetic joint infections are caused by gram positive cocci, (*Staphylococcus aureus*, Coagulase Negative Staphylococci, Beta-Hemolytic *Streptococcus*, Viridans Group Streptococci) and enterococci. Often multiple strains of *staphylococcus* can be present in a single prosthetic infection. Other organisms include aerobic gram negative bacilli, Enterobacteriacea, *Pseudomonas aeruginosa* and Anaerobes (such as *Peptostreptococcus* and *Bacteroides* species). Polymicrobial infections account for 12% of infections.

The diagnosis of an infected implant is difficult due to the highly variable presentation; fever, general malaise, swelling, erythema, joint pain, loosening of the implant, or even acute septicemia. Fulminate presentations are typically caused by more virulent organisms such as *Stapylococcus arureus* and pyogneic beta-hemolytic streptococci. Chronic indolent courses are more typical of coagulase-negative staphylococci.

Management of an infected orthopedic implant usually requires prolonged use of antibiotics and surgery to remove the infected device. Surgery requires debridement of the infected tissue, soft tissue, bone, cement, and removal of the infected implant. After a period of prolonged antibiotic use (weeks, months and sometimes a year to ensure microbial eradication), it is possible to implant a replacement prosthesis. Some authors advocate the use of antibiotic impregnated cement, but cite concerns regarding the risk of developing antibiotic resistance; especially methecillin resistance. If bone loss is extensive, an arthrodesis is often performed and amputation is necessary in some cases. Even when an infection is eradicated, the patient can be left severely compromised physically, have significant pain and carry a high risk of re-infection.

It is therefore extremely clinically important to develop orthopedic implants capable of resisting or reducing the rate of infection. An effective orthopedic implant coating would reduce the incidence of joint and hardware infection; lower the incidence of prosthetic failure, sepsis, amputation and even death; and also decrease the number of orthopedic implants requiring replacement, resulting in lower morbidity for patients with these implants.

In a preferred embodiment, doxorubicin, mitoxantrone, 5-fluorouracil and/or etoposide are formulated into a coating applied to the surface of the components of the orthopedic implant. The drug(s) can be applied in several manners: (a) as a coating applied to the external intraosseous surface of the prosthesis; (b) as a coating applied to the external (articular) surface of the prosthesis; (c) as a coating applied to all or parts of both surfaces; (d) as a coating applied to the surface of the orthopedic hardware (plates, screws, etc); (e) incorporated into the polymers which comprise the prosthetic joints (e.g. articular surfaces and other surface coatings) and hardware (e.g. polylactic acid screws and plates); and/or (f) incorporated into the components of the cements used to secure the orthopedic implants in place.

Drug-coating of, or drug incorporation into orthopedic implant will allow bacteriocidal drug levels to be achieved locally on the implant surface, thus reducing the incidence of bacterial colonization and subsequent development of infectious complications, while producing negligible systemic exposure to the drugs. Although for some agents polymeric carriers are not required for attachment of the drug, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

The drugs of interest can also be incorporated into calcium phosphate or hydroxyapatite coatings on the medical devices.

As orthopedic implants are made in a variety of configurations and sizes, the exact dose administered will vary with implant size, surface area, design and portions of the implant coated. However, certain principles can be applied in the application of this art. Drug dose can be calculated as a function of dose per unit area (of the portion of the implant being coated), total drug dose administered can be measured and appropriate surface concentrations of active drug can be determined. Regardless of the method of application of the drug to the orthopedic implant, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the orthopedic implant components, or applied without a carrier polymer, the total dose of doxorubicin applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the orthopedic implant to which drug is applied and/or incorporated) should fall within the range of 0.01 µg-100 µg per $mm^2$ of surface area. In a particularly preferred embodiment, doxorubicin should be applied to the orthopedic implant surface at a dose of 0.1 µg/$mm^2$-10 µg/$mm^2$. As different polymer and non-polymer coatings will release doxorubicin at differing rates, the above dosing parameters should be utilized in combination with the release rate of the drug from the orthopedic implant surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$M; although for some embodiments lower concentrations are sufficient). In a preferred embodiment, doxorubicin is released from the surface of the orthopedic implant such that anti-infective activity is maintained for a period ranging from several hours to several months. As described previously, the risk of infectious contamination of the implant is greatest over the first 3 days. Therefore, in a particularly preferred embodiment, the majority (or all) of the drug is released over the first 72 hours to prevent infection while allowing normal healing to occur thereafter. It should be readily evident based upon the discussion provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g., a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the orthopedic implant, or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the orthopedic implant to which drug is applied and/or incorporated) should fall within the range of 0.01 µg-20 µg per $mm^2$ of surface area. In a particularly preferred embodiment, mitoxantrone should be applied to the orthopedic implant surface at a dose of 0.05 µg/$mm^2$-3 µg/$mm^2$. As different polymer and non-polymer coatings will release mitoxantrone at differing rates, the above dosing parameters should be utilized in combination with the release rate of the drug from the orthopedic implant surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the orthopedic implant surface such that anti-infective activity is maintained for a period ranging from several hours to several months. As described previously, the risk of infectious contamination of the implant is greatest over the first 3 days. Therefore, in one embodiment, the majority (or all) of the drug is released over the first 72 hours to prevent infection while allowing normal healing to occur thereafter. It should be readily evident based upon the discussion provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the orthopedic implant, or applied without a carrier polymer, the total dose of 5-fluorouracil applied should not exceed 250 mg (range of 1.0 μg to 250 mg). In a particularly preferred embodiment, the total amount of drug applied should be in the range of 10 μg to 25 mg. The dose per unit area (i.e. the amount of drug as a function of the surface area of the portion of the orthopedic implant to which drug is applied and/or incorporated) should fall within the range of 0.1 μg-1 mg per $mm^2$ of surface area. In a particularly preferred embodiment, 5-fluorouracil should be applied to the orthopedic implant surface at a dose of 1.0 μg/$mm^2$-50 μg/$mm^2$. As different polymer and non-polymer coatings will release 5-fluorouracil at differing rates, the above dosing parameters should be utilized in combination with the release rate of the drug from the orthopedic implant surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the orthopedic implant surface such that anti-infective activity is maintained for a period ranging from several hours to several months. As described previously, the risk of infectious contamination of the implant is greatest over the first 3 days. Therefore, in a particularly preferred embodiment, the majority (or all) of the drug is released over the first 72 hours to prevent infection while allowing normal healing to occur thereafter. It should be readily evident based upon the discussion provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the orthopedic implant, or applied without a carrier polymer, the total dose of etoposide applied should not exceed 25 mg (range of 0.1 μg to 25 mg). In a particularly preferred embodiment, the total amount of drug applied should be in the range of 1 μg to 5 mg. The dose per unit area (i.e. the amount of drug as a function of the surface area of the portion of the orthopedic implant to which drug is applied and/or incorporated) should fall within the range of 0.01 μg-100 μg per $mm^2$ of surface area. In a particularly preferred embodiment, etoposide should be applied to the orthopedic implant surface at a dose of 0.1 μg/$mm^2$-10 μg/$mm^2$. As different polymer and non-polymer coatings will release etoposide at differing rates, the above dosing parameters should be utilized in combination with the release rate of the drug from the orthopedic implant surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the orthopedic implant such that anti-infective activity is maintained for a period ranging from several hours to several months. As described previously, the risk of infectious contamination of the implant is greatest over the first 3 days. Therefore, in a particularly preferred embodiment, the majority (or all) of the drug is released over the first 72 hours to prevent infection while allowing normal healing to occur thereafter. It should be readily evident based upon the discussion provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the orthopedic implant coating. Similarly anthracyclines (e.g., doxorubicin or mitoxantrone), fluoropyrimidines (e.g., 5-fluorouracil), folic acid antagonists (e.g., methotrexate) and/or podophylotoxins (e.g., etoposide) can be combined with traditional antibiotic and/or antifungal agents to enhance efficacy.

L. Infections Associated with Other Medical Devices and Implants

Implants are commonly used in the practice of medicine and surgery for a wide variety of purposes. These include implants such as drainage tubes, biliary T-tubes, clips, sutures, meshes, barriers (for the prevention of adhesions), anastomotic devices, conduits, irrigation fluids, packing agents, stents, staples, inferior vena cava filters, embolization agents, pumps (for the delivery of therapeutics), hemostatic implants (sponges), tissue fillers, cosmetic implants (breast implants, facial implants, prostheses), bone grafts, skin grafts, intrauterine devices (IUD), ligatures, titanium implants (particularly in dentistry), chest tubes, nasogastric tubes, percutaneous feeding tubes, colostomy devices, bone wax, and Penrose drains, hair plugs, ear rings, nose rings, and other piercing-associated implants, as well as anaesthetic solutions to name a few. Any foreign body when placed into the body is at risk for developing an infection—particularly in the period immediately following implantation.

The drug-coating, dosing, surface concentrations and release kinetics of these implants is identical to the embodiment described above for orthopedic implants. In addition, doxorubicin, mitoxantrone, 5-fluorouracil and/or etoposide can be added to solutions used in medicine (storage solutions, irrigation fluids, saline, mannitol, glucose solutions, lipids, nutritional fluids, and anaesthetic solutions) to prevent infection transmitted via infected solutions/fluids used in patient management.

M. Infections Associated with Ocular Implants

The principle infections of medical device implants in the eye are endophthalmitis associated with intraocular lens implantation for cataract surgery and corneal infections secondary to contact lens use.

Infections of Intraocular Lenses

The number of intraocular lenses implanted in the United States has grown exponentially over the last decade. Currently, over 1 million intraocular lenses are implanted annually, with the vast majority (90%) being placed in the posterior chamber of the eye. Endophthalmitis is the most common infectious complication of intraocular lens placement and occurs in approximately 0.3% of surgeries (3,000 cases per year). The vast majority are due to surgical contamination and have an onset within 48 hours of the procedure.

The most common causes of endophthalmitis are Coagulase Negative Staphylococci (principally *Staphylococcus epidermidis*), *Staphylococcus aureus*, Enterococci, and *Proteus mirabilis*. Symptoms of the condition include blurred vision, ocular pain, headache, photophobia, and corneal edema. The treatment of endophthalmitis associated with cataract surgery includes vitrectomy and treatment with systemic and/or intravitreal antibiotic therapy. Although most cases do not require removal of the lens, in complicated cases, visual acuity can be permanently affected and/or the lens must be removed and replaced at a later date. An effective intraocular lens coating would reduce the incidence of endophthalmitis and also decrease the number of intraocular lens requiring replacement, resulting in lower morbidity for patients with these implants.

In a preferred embodiment, doxorubicin, mitoxantrone, 5-fluorouracil and/or etoposide are formulated into a coating applied to the surface of the components of the intraocular lens. The drug(s) can be applied in several manners: (a) as a coating applied to the external surface of the lens; (b) as a coating applied to the internal (luminal) surface of the lens; (c) as a coating applied to all or parts of both surfaces of the lens; and/or (d) incorporated into the polymers which comprise the lens.

Drug-coating of, or drug incorporation into intraocular lenses will allow bacteriocidal drug levels to be achieved locally on the lens surface, thus reducing the incidence of bacterial colonization and subsequent development of infectious complications, while producing negligible systemic exposure to the drugs. Although for some agents polymeric carriers are not required for attachment of the drug, several polymeric carriers are particularly suitable for use in this embodiment. Of particular interest are polymeric carriers such as polyurethanes (e.g., ChronoFlex AL 85A [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof.

As intraocular lenses are made in a variety of configurations and sizes, the exact dose administered will vary with lens size, surface area, design and portions of the lens coated. However, certain principles can be applied in the application of this art. Drug dose can be calculated as a function of dose per unit area (of the portion of the lens being coated), total drug dose administered can be measured and appropriate surface concentrations of active drug can be determined. Regardless of the method of application of the drug to the intraocular lens, the preferred anticancer agents, used alone or in combination, should be administered under the following dosing guidelines:

(a) Anthracyclines. Utilizing the anthracycline doxorubicin as an example, whether applied as a polymer coating, incorporated into the polymers which make up the intraocular lens components, or applied without a carrier polymer, the total dose of doxorubicin applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the intraocular lens to which drug is applied and/or incorporated) should fall within the range of 0.01 µg-100 µg per $mm^2$ of surface area. In a particularly preferred embodiment, doxorubicin should be applied to the intraocular lens surface at a dose of 0.1 µg/$mm^2$-10 µg/$mm^2$. As different polymer and non-polymer coatings will release doxorubicin at differing rates, the above dosing parameters should be utilized in combination with the release rate of the drug from the intraocular lens surface such that a minimum concentration of $10^{-7}$-$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the intraocular lens such that anti-infective activity is maintained for a period ranging from several hours to several months. In a particularly preferred embodiment the drug is released in effective concentrations for a period ranging from 1-12 weeks. It should be readily evident based upon the discussion provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g. a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the intraocular lens, or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e. the amount of drug as a function of the surface area of the portion of the intraocular lens to which drug is applied and/or incorporated) should fall within the range of 0.01 µg-20 µg per $mm^2$ of surface area. In a particularly preferred embodiment, mitoxantrone should be applied to the intraocular lens surface at a dose of 0.05 µg/$mm^2$-3 µg/$mm^2$. As different polymer and non-polymer coatings will release mitoxantrone at differing rates, the above dosing parameters should be utilized in combination with the release rate of the drug from the intraocular lens surface such that a minimum concentration of $10^{-5}$-$10^{-6}$ M of mitoxantrone is maintained. It is necessary to insure that drug concentrations on the surface exceed concentrations of mitoxantrone known to be lethal to multiple species of bacteria and fungi (i.e. are in excess of $10^{-5}$ M; although for some embodiments lower drug levels will be sufficient). In a preferred embodiment, mitoxantrone is released from the intraocular lens surface such that anti-infective activity is maintained for a period ranging from several hours to several months. In a particularly preferred embodiment the drug is released in effective concentrations for a period ranging from 1-12 weeks. It should be readily evident based upon the discussion provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g. a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the intraocular lens, or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e. the amount of drug as a function of the surface area of the portion of the intraocular lens to which drug is applied and/or incorporated) should fall within the range of 0.1 µg-1 mg per mm$^2$ of surface area. In a particularly preferred embodiment, 5-fluorouracil should be applied to the intraocular lens surface at a dose of 1.0 µg/mm$^2$-50 µg/mm$^2$. As different polymer and non-polymer coatings will release 5-fluorouracil at differing rates, the above dosing parameters should be utilized in combination with the release rate of the drug from the intraocular lens surface such that a minimum concentration of $10^{-4}$-$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the intraocular lens surface such that anti-infective activity is maintained for a period ranging from several hours to several months. In a particularly preferred embodiment the drug is released in effective concentrations for a period ranging from 1-12 weeks. It should be readily evident based upon the discussion provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the intraocular lens, or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e. the amount of drug as a function of the surface area of the portion of the intraocular lens to which drug is applied and/or incorporated) should fall within the range of 0.01 µg-100 µg per mm$^2$ of surface area. In a particularly preferred embodiment, etoposide should be applied to the intraocular lens surface at a dose of 0.1 µg/mm$^2$-10 µg/mm$^2$. As different polymer and non-polymer coatings will release etoposide at differing rates, the above dosing parameters should be utilized in combination with the release rate of the drug from the intraocular lens surface such that a concentration of $10^{-5}$-$10^{-6}$ M of etoposide is maintained. It is necessary to insure that surface drug concentrations exceed concentrations of etoposide known to be lethal to a variety of bacteria and fungi (i.e. are in excess of $10^{-5}$ M; although for some embodiments lower drug levels will be sufficient). In a preferred embodiment, etoposide is released from the surface of the intraocular lens such that anti-infective activity is maintained for a period ranging from several hours to several months. In a particularly preferred embodiment the drug is released in effective concentrations for a period ranging from 1-12 weeks. It should be readily evident based upon the discussion provided herein that analogues and derivatives of etoposide (as described previously) with similar functional activity can be utilized for the purposes of this invention; the above dosing parameters are then adjusted according to the relative potency of the analogue or derivative as compared to the parent compound (e.g. a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate) and podophylotoxins (e.g., etoposide) can be utilized to enhance the antibacterial activity of the intraocular lens coating. Similarly anthracyclines (e.g., doxorubicin or mitoxantrone), fluoropyrimidines (e.g., 5-fluorouracil), folic acid antagonists (e.g., methotrexate) and/or podophylotoxins (e.g., etoposide) can be combined with traditional antibiotic and/or antifungal agents to enhance efficacy.

Corneal Infections Secondary to Contact Lens Use

Contact lenses are primarily used for the correction of refractive errors, but are also used after cataract surgery (Aphakie lenses) and "bandage" lenses are used following corneal trauma. Over 24 million people wear contact lenses and many of them will suffer from ulcerative keratitis resulting from contact lens-associated infection. These infections are typically bacterial in nature, are secondary to corneal damage/defects, and are caused primarily by Gram Positive Cocci and *Pseudomonas aeruginosa*.

The drug-coating of contact lenses is identical to the embodiment described above for intraocular lenses. In addition, doxorubicin, mitoxantrone, 5-fluorouracil and/or etoposide can be added to contact lens storage solution to prevent infection transmitted via infected cleaning/storage solutions.

It should be readily evident to one of skill in the art that any of the previously mentioned agents, or derivatives and analogues thereof, can be utilized to create variation of the above compositions without deviating from the spirit and scope of the invention.

EXAMPLES

Example 1

MIC Determination by Microtitre Broth Dilution Method

A. MIC assay of various gram negative and positive bacteria MIC assays were conducted essentially as described by Amsterdam, D. 1996. Susceptibility testing of antimicrobials in liquid media, p. 52-111. In Loman, V., ed. Antibiotics in laboratory medicine, 4th ed. Williams and Wilkins, Baltimore, Md. Briefly, a variety of compounds were tested for antibacterial activity against isolates of *P. aeruginosa, K. pneumoniae, E. coli, S. epidermidis* and *S. aureus* in the MIC (minimum inhibitory concentration assay under aerobic conditions using 96 well polystyrene microtitre plates (Falcon 1177), and Mueller Hinton broth at 37° C. incubated for 24 h. (MHB was used for most testing except C721 (*S. pyogenes*), which used Todd Hewitt broth, and *Haemophilus influenzae*, which used *Haemophilus* test medium (HTM)) Tests were conducted in triplicate. The results are provided below in Table 1.

TABLE 1

Minimum Inhibitory Concentrations of Therapeutic Agents Against Various Gram Negative and Positive Bacteria

| | Bactrial Strain | | | | | |
|---|---|---|---|---|---|---|
| Drug | *P. aeruginosa* PAE/K799 H187 Wt Gram − | *K. pneumoniae* ATCC13883 C238 wt Gram − | *E. coil* UB1005 C498 wt Gram − | *S. aureus* ATCC25923 C622 wt Gram + | *S. epidermidis* C621 wt Gram + | *S. pyogenes* C721 wt Gram + |
| doxorubicin | $10^{-5}$ | $10^{-6}$ | $10^{-4}$ | $10^{-5}$ | $10^{-6}$ | $10^{-7}$ |
| mitoxantrone | $10^{-5}$ | $10^{-6}$ | $10^{-5}$ | $10^{-5}$ | $10^{-5}$ | $10^{-6}$ |
| 5-fluorouracil | $10^{-5}$ | $10^{-6}$ | $10^{-6}$ | $10^{-7}$ | $10^{-7}$ | $10^{-4}$ |
| methotrexate | N | $10^{-6}$ | N | $10^{-5}$ | N | $10^{-6}$ |
| etoposide | N | $10^{-5}$ | N | $10^{-5}$ | $10^{-6}$ | $10^{-5}$ |
| camptothecin | N | N | N | N | $10^{-4}$ | N |
| hydroxyurea | $10^{-4}$ | N | N | N | N | $10^{-4}$ |
| cisplatin | $10^{-4}$ | N | N | N | N | N |
| tubercidin | N | N | N | N | N | N |
| 2-mercaptopurine | N | N | N | N | N | N |
| 6-mercaptopurine | N | N | N | N | N | N |
| Cytarabine | N | N | N | N | N | N |

Activities are in Molar concentrations
Wt = wild type
N = No activity

B. MIC of Antibiotic-Resistant Bacteria

Various concentrations of the following compounds, mitoxantrone, cisplatin, tubercidin, methotrexate, 5-fluorouracil, etoposide, 2-mercaptopurine, doxorubicin, 6-mercaptopurine, camptothecin, hydroxyurea and cytarabine were tested for antibacterial activity against clinical isolates of a methicillin resistant *S. aureus* and a vancomycin resistant *pediococcus* clinical isolate in an MIC assay as described above. Compounds which showed inhibition of growth (MIC value of <1.0×10-3) included: mitoxantrone (both strains), methotrexate (vancomycin resistant *pediococcus*), 5-fluorouracil (both strains), etoposide (both strains), and 2-mercaptopurine (vancomycin resistant *pediococcus*).

Example 2

Catheter—Dip Coating—Non-Degradable Polymer

A coating solution is prepared by dissolving 20 g ChronoFlex Al 85A (CT Biomaterials) in 100 mL DMAC:THF (40:60) at 50° C. with stirring. Once dissolved, the polymer solution is cooled to room temperature. 20 mg mitoxantrone is added to 2 mL of the polyurethane solution. The solution is stirred until a homogenious mixture is obtained. Polyurethane 7 French tubing is dipped into the polymer/drug solution and then withdrawn. The coated tube is air dried (80° C.). The sample is then dried under vacuum to further reduce the residual solvent in the coating.

Example 3

Catheter—Dip Coating—Degradable Polymer

A coating solution is prepared by dissolving 2 g PLG (50:50) in 10 mL dichloromethane:methanol (70:30). Once dissolved, 20 mg mitoxantrone is added to the polymer solution. Once the solution is a homogeneous solution, polyurethane 7 French tubing is dipped into the solution and then withdrawn. The coated tube is air dried. The sample is then dried under vacuum to further reduce the residual solvent in the coating.

Example 4

Catheter—Dip Coating—Drug Only 1 mL methanol is added to 20 mg mitoxantrone. Polyurethane 7 French tubing is dipped into the solution and then withdrawn. The coated tube is air dried. The sample is then dried under vacuum to further reduce the residual solvent in the coating.

Example 5

Catheter—Dip Coating—Drug Impregnation 0.6 mL methanol is added to 20 mg mitoxantrone. 1.4 mL DMAC is added slowly. Polyurethane 7 French tubing is dipped into the solution. After various periods of time (2 min, 5 min, 10 min, 20 min, 30 min) the tube was withdrawn. The coated tube is air dried (80° C.). The sample is then dried under vacuum to further reduce the residual solvent in the coating.

Example 6

Tympanostomy Tubes—Dip Coating—Non-Degradable Polymer

A coating solution is prepared by dissolving 20 g ChronoFlex Al 85A (CT Biomaterials) in 100 mL DMAC:THF (50:50) at 50° C. with stirring. Once dissolved, the polymer solution is cooled to room temperature. 20 mg mitoxantrone is added to 2 mL of the polyurethane solution. The solution is stirred until a homogenious mixture is obtained. A stainless steel tympanostomy tube is dipped into the polymer/drug solution and then withdrawn. The coated tube is air dried (80° C.). The sample is then dried under vacuum to further reduce the residual solvent in the coating.

Example 7

Catheter—Dip Coating—Non-Degradable Polymer

A coating solution is prepared by dissolving 20 g ChronoFlex Al 85A (CT Biomaterials) in 100 mL THF at 50° C. with stirring. Once dissolved, the polymer solution is cooled to room temperature. 20 mg etoposide is added to 2 mL of the polyurethane solution. The solution is stirred until a homogenious mixture is obtained. Polyurethane 7 French tubing is dipped into the polymer/drug solution and then withdrawn. The coated tube is air dried (80 C). The sample is then dried under vacuum to further reduce the residual solvent in the coating.

Example 8

Catheter—Dip Coating—Degradable Polymer

A coating solution is prepared by dissolving 2 g PLG (50:50) in 10 mL dichloromethane:methanol (70:30). Once dissolved, 20 mg etoposide is added to the polymer solution. Once the solution is a homogeneous solution, polyurethane 7 French tubing is dipped into the solution and then withdrawn. The coated tube is air dried. The sample is then dried under vacuum to further reduce the residual solvent in the coating.

Example 9

Catheter—Dip Coating—Drug Only 1 mL THF is added to 20 mg etoposide. Polyurethane 7 French tubing is dipped into the solution and then withdrawn. The coated tube is air dried. The sample is then dried under vacuum to further reduce the residual solvent in the coating.

Example 10

Catheter—Dip Coating—Drug Impregnation 0.6 mL methanol is added to 1.4 mL DMAC which contains 20 mg etoposide. Polyurethane 7 French tubing is dipped into the solution. After various periods of time (2 min, 5 min, 10 min, 20 min, 30 min) the tube was withdrawn. The coated tube is air dried (80° C.). The sample is then dried under vacuum to further reduce the residual solvent in the coating.

Example 11

Tympanostomy Tubes—Dip Coating—Non-Degradable Polymer

A coating solution is prepared by dissolving 20 g ChronoFlex Al 85A (CT Biomaterials) in 100 mL DMAC:THF (50:50) at 50° C. with stirring. Once dissolved, the polymer solution is cooled to room temperature. 20 mg etoposide is added to 2 mL of the polyurethane solution. The solution is stirred until a homogenious mixture is obtained. A stainless steel tympanostomy tube is dipped into the polymer/drug solution and then withdrawn. The coated tube is air dried (80° C.). The sample is then dried under vacuum to further reduce the residual solvent in the coating.

Example 12

Covalent Attachment of Doxorubicin to a Polymer Coated Device

A piece of polyurethane 7 French tubing, with and without an oxygen plasma pretreatment step, is dipped into a solution of 5% (w/w) poly(ethylene-co acrylic acid) in THF. The sample was dried at 45° C. for 3 hours. The coated tubing was then dipped into a water:methanol (30:70) solution that contained 1-(3-dimethylaminopropyl)-3-ethylcarbodiimide (EDC) and 20 mg/mL Doxorubicin. After various times (15 min, 30 min, 60 min 120 min) the tubing is removed from the solution and dried at 60° C. for 2 hours followed by vacuum drying for 24 hours.

Example 13

Covalent Attachment of Doxorubicin to a Device Surface

A piece of polyurethane 7 French tubing that has undergone a oxygen plasma pretreatment step is dipped into a water:methanol (30:70) solution that contained 1-(3-dimethylaminopropyl)-3-ethylcarbodiimide (EDC) and 20 mg/mL Doxorubicin. After various times (15 min, 30 min, 60 min 120 min) the tubing is removed from the solution and dried at 60° C. for 2 hours followed by vacuum drying for 24 hours.

Example 14

Impregnation of 5-Fluorouracil into Polyurethane Catheter

A solution was prepared by dissolving 100 mg of 5-Fluorouracil into 20 ml anhydrous methanol. Polyurethane catheter tubing was immersed in this solution for 16 hours. The catheter tubing was vacuum dried at 50° C. for 16 hours.

Example 15

Impregnation of Mitoxantrone into Polyurethane Catheter

A solution was prepared by dissolving 20 mg of Mitoxantrone-2HCl into 20 ml anhydrous methanol. Polyurethane catheter tubing was immersed in this solution for 16 hours. The catheter tubing was vacuum dried at 50° C. for 16 hours.

Example 16

Impregnation of Doxorubicin into Polyurethane Catheter

A solution was prepared by dissolving 20 mg of Doxorubicin-HCl into 20 ml anhydrous methanol. Polyurethane catheter tubing was immersed in this solution for 16 hours. The catheter tubing was vacuum dried at 50° C. for 16 hours.

Example 17

Polyurethane Dip Coating with 5-Fluorouracil

A solution was prepared by dissolving 125 mg 5-Fluorouracil and 2.5 g of Chronoflex AL85A (CT Biomaterials) in 50 ml of THF at 55° C. The solution was cooled to room temperature. Polyurethane catheters were weighted at one end and dipped in solution and then removed immediately. This process was repeated three times with 1 minute drying time interval between each dipping process. The catheter tubing was vacuum dried at 50° C. for 16 hours.

Example 18

Polyurethane Dip Coating with 5-Fluorouracil and Palmitic Acid

A solution was prepared by dissolving 125 mg 5-Fluorouracil, 62.5 mg of palmitic acid, and 2.437 g of Chronoflex AL85A (CT Biomaterials) in 50 ml of THF at 55° C. The solution was cooled to room temperature. Polyurethane catheters were weighted at one end and dipped in solution and then removed immediately. This process was repeated three times with a 1 minute drying time interval between each dipping process. The catheter tubing was vacuum dried at 50° C. for 16 hours.

Example 19

Catheter Dip Coating with Nafion and Mitoxantrone

Catheters are weighted at one end and dipped into 5% Nafion solution (Dupont) and then removed immediately. This process was repeated three times with a 1 minute drying time interval between each dipping process. The catheter tubing was dried at room temperature for 2 hours. A solution was prepared with 1 mg of mitoxantrone-2HCl in 40 ml of deionized water. The catheter tubing was immersed in the solution for 5 minutes, and then was washed with deionized water and dried at room temperature.

Example 20

Catheter Dip Coating with Nafion and Doxorubicin

Catheters are weighted at one end and dipped into 5% Nafion solution (Dupont) and then removed immediately. This process was repeated three times with a 1 minute drying time interval between each dipping process. The catheter tubing was dried at room temperature for 2 hours. A solution was prepared with 1 mg of doxorubicin-HCl in 40 ml of deionized water. The catheter tubing was immersed in the solution for 5 minutes, and then was washed with deionized water and dried at room temperature.

Example 21

Preparation of Release Buffer

The release buffer was prepared by adding 8.22 g sodium chloride, 0.32 g sodium phosphate monobasic (monohydrate) and 2.60 g sodium phosphate dibasic (anhydrous) to a beaker. 1 L HPLC grade water was added and the solution was stirred until all the salts were dissolved. If required, the pH of the solution was adjusted to pH 7.4±0.2 using either 0.1 N NaOH or 0.1 N phosphoric acid.

Example 22

Release Study to Determine Release Profile of the Therapeutic Agent from a Catheter A sample of the therapeutic agent-loaded catheter was placed in a 15 mL culture tube. 15 mL release buffer (Example 21) was added to the culture tube. The tube was sealed with a Teflon lined screw cap and was placed on a rotating wheel in a 37° C. oven. At various time point, the buffer is withdrawn from the culture tube and is replaced with fresh buffer. The withdrawn buffer is then analysed for the amount of therapeutic agent contained in this buffer solution.

Example 23

HPLC Analysis of Therapeutic Agents in Release Buffer

The following chromatographic conditions were used to quantify the amount of the therapeutic agent in the release medium:

| Therapeutic Agent | Column | Mobile Phase | Flow Rate (mL/min) | Run Time (min) | Injection Volume (uL) | Detection Wavelength (nm) |
|---|---|---|---|---|---|---|
| 5-Fluorouracil | YMC ODS-AQ 150 × 4.6 mm, 5 um | PBS, pH 6.8 | 1 | 8 | 100 | 268 |
| Doxorubicin | ACE 5 (V02-742) 150 × 4 mm | 20% CAN, 26% Methanol, 54% PBS (pH 3.6) | 1 | 10 | 10 | 254 |
| Mitoxantrone | ACE 5 C18, 150 × 4 mm, 5 um | Phosphate buffer (pH 2.3) | 1 | 4 | 10 | 658 |

Example 24

Effect of Palmitic Acid on the Release Profile of 5-Fluorouracil from a Polyurethane Film A 25% (w/v) Chronoflex AL 85A (CT Biomaterials) solution was prepared in THF. 50 mg 5-fluorouracil was weighed into each of 4 glass scintillation vials. Various amount of palmitic acid were added to each vial. 20 mL of the polyurethane solution was added to each scintillation vial. The samples were rotated at 37° C. until the solids had all dissolved. Samples were then cast as films using a casting knife on a piece of release liner. Samples were air dried and then dried overnight under vacuum. A portion of these samples were used to perform release studies (Example 22). FIG. 1 show the effect of palmitic acid on the release profile of 5-fluorouracil.

Example 25

Radial Diffusion Assay for Testing Drug Impregnated Catheters Against Various Strains of Bacteria An overnight bacterial culture was diluted 1 to 5 to a final volume of 5 mls fresh Mueller Hinton broth. Then 100 μl of the diluted bacterial culture were spread onto Mueller Hinton agar plates. A test material (e.g., catheter tubing), with or without drug, was placed on the center of the plate. For example, catheters are typically 1 cm long and about 3 mm in diameter (which may be made of polyurethane, silicon or other suitable material) and are loaded with drug either through dip-coating or through use of a drug-impregnated coating. The plates were incubated at 37° C. for 16-18 hours. The zone of clearing around a test material was then measured (e.g., the distance from the catheter to where bacterial growth is inhibited), which indicated the degree of bacterial growth prevention. Various bacterial strains that may be tested include, but are not limited to, the following: *E. coli* C498 UB1005, *P. aeruginosa* H187, *S. aureus* C622 ATCC 25923, and *S. epidermidis* C621.

One cm polyurethane catheters coated with 5-fluorouracil at several concentrations (2.5 mg/mL and 5.0 mg/mL) were examined for their effect against *S. aureus*. The zone of inhibition around the catheters coated in a solution of 2.5 mg/mL 5-Fluorouracil and placed on Mueller Hinton agar plates as described above was 35×39 mm, and for the catheters coated in a solution of 5.0 mg/mL 5-Fluorouracil was 30×37 mm. Catheters without drug showed no zone of inhibition. These results demonstrate the efficacy of 5-fluorouracil coated on a catheter at inhibiting the growth of *S. aureus*.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An infection-resistant medical implant, comprising a medical device and a fluoropyrimidine at 0.01 μg to 1 mg per $mm^2$ of surface of the portion of medical device covered or coated, wherein the medical device release the fluoropyrimidine, wherein the medical device is covered or coated in whole or in part with fluoropyrimidine in an amount effective to reduce or inhibit the likelihood of infection associated with the implantation of the medical implant in a patient, and wherein the medical implant does not release the fluoropyrimidine in an amount effective for treating cancer.

2. The medical implant of claim 1 wherein the fluoropyrimidine is 5-fluorouracil.

3. The medical implant of claim 1 wherein the medical device is covered or coated in whole or in part with a composition that comprises the fluoropyrimidine and a polymer.

4. The medical implant of claim 3 wherein the polymer is a biodegradable polymer.

5. The medical implant of claim 3 wherein the polymer is a non-biodegradable polymer.

6. The medical implant of claim 3 wherein the polymer is a polyurethane.

7. The medical implant of claim 3 wherein the polymer is a poly(lactide-co-glycolide).

8. The medical implant of claim 1, wherein the fluoropyrimidine is floxuridine.

9. The medical implant of claim 1, wherein the medical device is suture.

* * * * *

UNITED STATES PATENT AND TRADEMARK OFFICE
CERTIFICATE OF CORRECTION

| | |
|---|---|
| PATENT NO. | : 8,425,927 B2 |
| APPLICATION NO. | : 12/939565 |
| DATED | : April 23, 2013 |
| INVENTOR(S) | : William L. Hunter et al. |

It is certified that error appears in the above-identified patent and that said Letters Patent is hereby corrected as shown below:

Title Page 3, Item (56):
"Anai, H. et al, "Sensitivity test for 5-Fluorouracil and Its Analogues, 1-(2-Tetrahydrofury 1)-5-Fluorouracil, Uracil/1-(2-Tetrahydrofuryl)-5-Fluorouracil (4:1) and 1-Hexylcaramoyl-5-Fluorouracil, Using the Subrenal Capsule Assay," Ongcology 45:144-147, 1988." should read, --Anai, H. et al, "Sensitivity test for 5-Fluorouracil and Its Analogues, 1-(2-Tetrahydrofuryl)-5-Fluorouracil, Uracil/1-(2-Tetrahydrofuryl)-5-Fluorouracil (4:1) and 1-Hexylcarbamoyl-5-Fluorouracil, Using the Subrenal Capsule Assay," Ongcology 45:144-147, 1988.--.

Title Page 4, Item (56):
"Fan, Barry M., "Preventing Vascular Catheter-Related Infections: Current Controversies," Healthcare Epidemiology CID 33:1733-1738, Nov. 15, 2001." should read, --Farr, Barry M., "Preventing Vascular Catheter-Related Infections: Current Controversies," Healthcare Epidemiology CID 33:1733-1738, Nov. 15, 2001.--.

Title Page 5, Item (56):
"Martin et al., "In vitro Susceptibility of 245 Yeast Isolates to Amphotericin B, 5-Fluorocytosine, Ketoconazole, Fluconazole and Itraconazole," Chemotherapy, 38:335-339, 1992." should read, --Martin et al., "In vitro Susceptibility of 245 Yeast Isolates to Amphotericin B, 5-Fluorocytosine, Ketoconazole, Fluconazole and Itraconazole," Chemotherapy, 38:335-339, 1992.--.

Title Page 6, Item (56):
"Ren, Dacheng et al., "Brief report. Inhibition of biofilm formation and swarming of Escherichia coli by (5Z)-4-bromo-5-(bromomethylene)-3-butyl-2(5H)-furanone," Environmental Microbiology 3(11):731-736, 2001." should read, --Ren, Dacheng et al., "Brief report: Inhibition of biofilm formation and swarming of Escherichia coli by (5Z)-4-bromo-5-(bromomethylene)-3-butyl-2(5H)-furanone," Environmental Microbiology 3(11):731-736, 2001.--.

Title Page 6, Item (56):
"Rival et al., "Antifungal activity in vitro of some imidazo[1,2-α]pyrimidine derivatives," Eur J. Med. Chem., 26(1):13-18, 1991." should read, --Rival et al., "Antifungal activity in vitro of some imidazo[1,2-a]pyrimidine derivatives," Eur J. Med. Chem., 26(1):13-18, 1991.--.

In the Claims:

Signed and Sealed this
Twenty-fourth Day of September, 2013

Teresa Stanek Rea
*Deputy Director of the United States Patent and Trademark Office*

Column 96, Lines 10-19:

"1. An infection-resistant medical implant, comprising a medical device and a fluoropyrimidine at 0.01 µg to 1 mg per $mm^2$ of surface of the portion of medical device covered or coated, wherein the medical device release the fluoropyrimidine, wherein the medical device is covered or coated in whole or in part with fluoropyrimidine in an amount effective to reduce or inhibit the likelihood of infection associated with the implantation of the medical implant in a patient, and wherein the medical implant does not release the fluoropyrimidine in an amount effective for treating cancer." should read, --1. An infection-resistant medical implant, comprising a medical device and a fluoropyrimidine, wherein the medical device is covered or coated in whole or in part with fluoropyrimidine at 0.01 µg to 1 mg per $mm^2$ of surface of the portion of medical device covered or coated, wherein the medical device releases the fluoropyrimidine in an amount effective to reduce or inhibit the likelihood of infection associated with the implantation of the medical implant in a patient, and wherein the medical implant does not release the fluoropyrimidine in an amount effective for treating cancer.--.